United States Patent
Marshall et al.

(10) Patent No.: US 12,234,212 B2
(45) Date of Patent: Feb. 25, 2025

(54) PEPTIDE CONJUGATES OF MICROTUBULE-TARGETING AGENTS AS THERAPEUTICS

(71) Applicant: Cybrexa 3, Inc., New Haven, CT (US)

(72) Inventors: Daniel Richard Marshall, New Haven, CT (US); Johanna Marie Csengery, New Fairfield, CT (US); Robert John Maguire, New Haven, CT (US); Robert A. Volkmann, Mystic, CT (US)

(73) Assignee: Cybrexa 3, Inc., New Haven, CT (US)

( * ) Notice: Subject to any disclaimer, the term of this patent is extended or adjusted under 35 U.S.C. 154(b) by 22 days.

(21) Appl. No.: 18/152,987

(22) Filed: Jan. 11, 2023

(65) Prior Publication Data

US 2024/0067616 A1   Feb. 29, 2024

Related U.S. Application Data

(62) Division of application No. 16/924,445, filed on Jul. 9, 2020, now Pat. No. 11,555,019.

(60) Provisional application No. 63/041,324, filed on Jun. 19, 2020, provisional application No. 62/872,638, filed on Jul. 10, 2019.

(51) Int. Cl.
*C07D 265/12* (2006.01)
*A61K 47/64* (2017.01)

(52) U.S. Cl.
CPC ............ *C07D 265/12* (2013.01); *A61K 47/64* (2017.08)

(58) Field of Classification Search
CPC ................................................... C07D 265/12
See application file for complete search history.

(56) References Cited

U.S. PATENT DOCUMENTS

| | | | |
|---|---|---|---|
| 5,658,920 A | 8/1997 | Terasawa et al. | |
| 5,770,605 A | 6/1998 | Terasawa et al. | |
| 5,834,476 A | 11/1998 | Terasawa et al. | |
| 6,100,283 A | 8/2000 | Griffin et al. | |
| 6,172,230 B1 | 1/2001 | Kamihara et al. | |
| 6,291,671 B1 | 9/2001 | Inoue et al. | |
| 6,310,082 B1 | 10/2001 | Griffin et al. | |
| 6,337,400 B1 | 1/2002 | Kamihara et al. | |
| 6,436,912 B1 | 8/2002 | Inoue et al. | |
| 6,495,541 B1 | 12/2002 | Webber et al. | |
| 6,504,029 B1 | 1/2003 | Kamihara et al. | |
| 6,548,494 B1 | 4/2003 | Webber et al. | |
| 6,552,197 B2 | 4/2003 | Kamihara et al. | |
| 6,696,437 B1 | 2/2004 | Lubisch et al. | |
| 6,811,996 B1 | 11/2004 | Inoue et al. | |
| 6,815,435 B2 | 11/2004 | Takahashi et al. | |
| 6,835,807 B1 | 12/2004 | Susaki et al. | |
| 6,838,450 B2 | 1/2005 | Inoue et al. | |
| 6,844,318 B2 | 1/2005 | Copeland et al. | |
| 7,041,818 B2 | 5/2006 | Susaki et al. | |
| 7,151,102 B2 | 12/2006 | Martin et al. | |
| 7,196,085 B2 | 3/2007 | Martin et al. | |
| 7,276,497 B2 | 10/2007 | Chari et al. | |
| 7,301,019 B2 | 11/2007 | Widdison et al. | |
| 7,374,762 B2 | 5/2008 | Amphlett et al. | |
| 7,411,063 B2 | 8/2008 | Widdison et al. | |
| 7,449,464 B2 | 11/2008 | Martin et al. | |
| 7,473,796 B2 | 1/2009 | Chari et al. | |
| 7,494,649 B2 | 2/2009 | Amphlett et al. | |
| 7,501,120 B2 | 3/2009 | Amphlett et al. | |
| 7,514,080 B2 | 4/2009 | Amphlett et al. | |
| 7,531,530 B2 | 5/2009 | Helleday et al. | |
| 7,692,006 B2 | 4/2010 | Menear | |
| 7,771,727 B2 | 8/2010 | Fuselier et al. | |
| 7,781,596 B1 | 8/2010 | Lubisch et al. | |
| 7,811,572 B2 | 10/2010 | Dai et al. | |
| 7,851,432 B2 | 12/2010 | Chari et al. | |
| 7,989,598 B2 | 8/2011 | Steeves et al. | |
| 8,012,485 B2 | 9/2011 | Amphlett et al. | |
| 8,067,613 B2 | 11/2011 | Gandhi | |
| 8,071,623 B2 | 12/2011 | Jones et al. | |
| 8,076,451 B2 | 12/2011 | Reshetnyak et al. | |
| 8,088,387 B2 | 1/2012 | Steeves et al. | |
| 8,137,669 B2 | 3/2012 | Goldmakher et al. | |
| 8,163,888 B2 | 4/2012 | Steeves et al. | |
| 8,198,417 B2 | 6/2012 | Steeves et al. | |
| 8,383,122 B2 | 2/2013 | Dai et al. | |
| 8,388,960 B2 | 3/2013 | Goldmakher et al. | |
| 8,435,528 B2 | 5/2013 | Chari et al. | |
| 8,563,509 B2 | 10/2013 | Chari et al. | |
| 8,603,483 B2 | 12/2013 | Chen et al. | |
| 8,624,003 B2 | 1/2014 | Kellogg et al. | |
| 8,685,920 B2 | 4/2014 | Chari et al. | |
| 8,697,736 B2 | 4/2014 | Penning et al. | |
| 8,703,909 B2 | 4/2014 | Reshetnyak et al. | |

(Continued)

FOREIGN PATENT DOCUMENTS

| AU | 2007247969 | 11/2007 |
|---|---|---|
| CN | 1195985 | 10/1998 |

(Continued)

OTHER PUBLICATIONS

Helft; Clin Cancer Res 2004, 10, 4363-4368. https://doi.org/10.1158/1078-0432.CCR-04-0088 (Year: 2004).*
Kadcyla (ado-trastuzumab emtansine) Prescribing Information, Revised May 2019, 31 pages. (Year: 2019).*
[No Author Listed], "Research progress of PARP inhibitors combined with chemotherapy drugs in the treatment of malignant tumors," Tumor, Dec. 2013, 372-377, 1 page (English abstract).
Adiyala et al., "Development of pyrrolo [2,1-c][1,4] benzodiazepine β-glucoside prodrugs for selective therapy of cancer," Bioorganic Chemistry, Feb. 2018, 76:288-293.
Aiello et al., "Abstract #6249: CBX-12: A low pH targeting alphalex™-exatecan conjugate for the treatment of solid tumors," Abstract, Cancer Research, Aug. 2020, 80(16): 4 pages, URL <https://cancerres.aacrjournals.org/content/80/16_Supplement/6249>.

(Continued)

*Primary Examiner* — Daniel R Carcanague
(74) *Attorney, Agent, or Firm* — Fish & Richardson P.C.

(57) ABSTRACT

The present invention relates to peptide conjugates of microtubule-targeting agents such as maytansinoid derivatives which are useful for the treatment of diseases such as cancer.

22 Claims, 7 Drawing Sheets

Specification includes a Sequence Listing.

(56) References Cited

U.S. PATENT DOCUMENTS

| | | |
|---|---|---|
| 8,754,190 B2 | 6/2014 | Ashley et al. |
| 8,795,673 B2 | 8/2014 | Li et al. |
| 8,841,425 B2 | 9/2014 | Chari et al. |
| 8,859,756 B2 | 10/2014 | Ross et al. |
| 8,933,205 B2 | 1/2015 | Dai et al. |
| 9,090,629 B2 | 7/2015 | Chari et al. |
| 9,150,649 B2 | 10/2015 | Singh et al. |
| 9,289,508 B2 | 3/2016 | Reshetnyak et al. |
| 9,376,500 B2 | 6/2016 | Kellogg et al. |
| 9,428,543 B2 | 8/2016 | Li et al. |
| 9,676,823 B2 | 6/2017 | Reshetnyak et al. |
| 9,771,432 B2 | 9/2017 | Kellogg et al. |
| 9,789,204 B2 | 10/2017 | Dai et al. |
| 9,808,537 B2 | 11/2017 | Masuda et al. |
| 9,814,781 B2 | 11/2017 | Reshetnyak et al. |
| 9,872,924 B2 | 1/2018 | Naito et al. |
| 9,914,748 B2 | 3/2018 | Li et al. |
| 9,919,059 B2 | 3/2018 | Wong et al. |
| 9,999,680 B2 | 6/2018 | Widdison |
| 10,064,855 B2 | 9/2018 | Langecker et al. |
| 10,195,288 B2 | 2/2019 | Masuda et al. |
| 10,383,878 B2 | 8/2019 | Hettmann et al. |
| 10,413,615 B2 | 9/2019 | Hutchins |
| 10,435,432 B2 | 10/2019 | Li et al. |
| 10,695,396 B2 | 6/2020 | Fukuda et al. |
| 10,729,782 B2 | 8/2020 | Naito et al. |
| 10,844,135 B2 | 11/2020 | Chari et al. |
| 10,933,069 B2 | 3/2021 | Marchall et al. |
| 11,555,019 B2 | 1/2023 | Marshall et al. |
| 11,634,508 B2 | 4/2023 | Marshall et al. |
| 2003/0105109 A1 | 6/2003 | Lavielle et al. |
| 2004/0235840 A1 | 11/2004 | Chari et al. |
| 2005/0256030 A1 | 11/2005 | Feng |
| 2008/0233107 A1 | 9/2008 | Reshetnyak et al. |
| 2012/0039990 A1 | 2/2012 | Reshetnyak et al. |
| 2012/0045524 A1 | 2/2012 | Wernet et al. |
| 2012/0266262 A1 | 10/2012 | Ashkenazi et al. |
| 2015/0051153 A1 | 2/2015 | Reshetnyak et al. |
| 2016/0303254 A1 | 10/2016 | Kolakowski et al. |
| 2017/0035906 A1 | 2/2017 | Naito et al. |
| 2017/0112891 A1 | 4/2017 | Dragovich et al. |
| 2017/0145044 A1 | 5/2017 | Hudson et al. |
| 2017/0207277 A1 | 7/2017 | Park |
| 2017/0226220 A1 | 8/2017 | Chari et al. |
| 2017/0267727 A1 | 9/2017 | Thevenin et al. |
| 2017/0267765 A1 | 9/2017 | Tsao |
| 2017/0274093 A1 | 9/2017 | Goldenberg et al. |
| 2018/0043013 A1 | 2/2018 | Chari et al. |
| 2018/0071403 A1 | 3/2018 | Naito et al. |
| 2018/0221500 A1 | 8/2018 | Reshetnyak et al. |
| 2019/0008981 A1 | 1/2019 | Masuda et al. |
| 2019/0010229 A1 | 1/2019 | Amphlett et al. |
| 2019/0030177 A1 | 1/2019 | Dai et al. |
| 2019/0151328 A1 | 5/2019 | Hettmann et al. |
| 2019/0175684 A1 | 6/2019 | Fukuda et al. |
| 2019/0209580 A1 | 7/2019 | Marshall et al. |
| 2020/0237926 A1 | 7/2020 | Reshetnyak et al. |
| 2020/0306243 A1 | 10/2020 | Howard et al. |
| 2021/0009536 A1 | 1/2021 | Marshall et al. |
| 2021/0009719 A1 | 1/2021 | Marshall et al. |
| 2021/0299137 A1 | 9/2021 | Marshall et al. |
| 2023/0416331 A1 | 12/2023 | Maguire et al. |
| 2024/0010755 A1 | 1/2024 | Marshall et al. |
| 2024/0093250 A1 | 3/2024 | Maguire et al. |
| 2024/0226308 A1 | 7/2024 | Paralkar et al. |

FOREIGN PATENT DOCUMENTS

| | | |
|---|---|---|
| CN | 1342161 | 3/2002 |
| CN | 1418112 | 5/2003 |
| CN | 101370497 | 2/2009 |
| CN | 102014956 | 4/2011 |
| CN | 101098854 | 12/2012 |
| CN | 106163559 | 11/2016 |
| CN | 109232719 | 1/2019 |
| CN | 110312549 | 10/2019 |
| EP | 1838715 | 10/2010 |
| EP | 2399609 | 12/2011 |
| EP | 1945647 | 1/2012 |
| EP | 1928503 | 10/2012 |
| EP | 1853322 | 6/2014 |
| EP | 3130608 | 2/2017 |
| EP | 2691155 | 11/2018 |
| EP | 2437790 | 2/2019 |
| JP | H11-510154 | 9/1999 |
| JP | 2002-534523 | 10/2002 |
| JP | 2004-520450 | 7/2004 |
| JP | 2018-535212 | 11/2018 |
| KR | 20160105146 | 9/2016 |
| NC | 2016/0001001 | 8/2016 |
| TW | I249527 | 2/2006 |
| TW | I460175 | 11/2014 |
| WO | WO 9902530 | 1/1999 |
| WO | WO 2000042040 | 7/2000 |
| WO | WO 2001041534 | 6/2001 |
| WO | WO 2002/098883 | 12/2002 |
| WO | WO 2003080047 | 10/2003 |
| WO | WO 2004087713 | 10/2004 |
| WO | WO 2004103272 | 12/2004 |
| WO | WO 2004110498 | 12/2004 |
| WO | WO 2005012305 | 2/2005 |
| WO | WO 2005012524 | 2/2005 |
| WO | WO 2005037992 | 4/2005 |
| WO | WO 2005053662 | 6/2005 |
| WO | WO 2006012527 | 2/2006 |
| WO | WO 2006033003 | 3/2006 |
| WO | WO 2006033006 | 3/2006 |
| WO | WO 2006033007 | 3/2006 |
| WO | WO 2006062779 | 6/2006 |
| WO | WO 2006078809 | 7/2006 |
| WO | WO 2006078816 | 7/2006 |
| WO | WO 2006113623 | 10/2006 |
| WO | WO 2007024536 | 3/2007 |
| WO | WO 2007056550 | 5/2007 |
| WO | WO 2008114114 | 9/2008 |
| WO | WO 2009002993 | 12/2008 |
| WO | WO 2009026177 | 2/2009 |
| WO | WO 2009134952 | 11/2009 |
| WO | WO 2009134976 | 11/2009 |
| WO | WO 2010141566 | 12/2010 |
| WO | WO 2011066418 | 6/2011 |
| WO | WO 2011098971 | 8/2011 |
| WO | WO 2011106639 | 9/2011 |
| WO | WO 2012047354 | 4/2012 |
| WO | WO 2012061590 | 5/2012 |
| WO | WO 2012135517 | 10/2012 |
| WO | WO 2013055987 | 4/2013 |
| WO | WO 2014057687 | 4/2014 |
| WO | WO 2014061277 | 4/2014 |
| WO | WO 2014066002 | 5/2014 |
| WO | WO 2014107024 | 7/2014 |
| WO | WO 2014134483 | 9/2014 |
| WO | WO 2015095755 | 6/2015 |
| WO | WO 2015108986 | 7/2015 |
| WO | WO 2015117002 | 8/2015 |
| WO | WO 2015146132 | 10/2015 |
| WO | WO 2015155976 | 10/2015 |
| WO | WO 2015155998 | 10/2015 |
| WO | WO 2016004043 | 1/2016 |
| WO | WO 2016028689 | 2/2016 |
| WO | WO 2016057398 | 4/2016 |
| WO | WO 2016081584 | 5/2016 |
| WO | WO 2016083433 | 6/2016 |
| WO | WO 2017064675 | 4/2017 |
| WO | WO 2017180834 | 10/2017 |
| WO | WO 2017199042 | 11/2017 |
| WO | WO 2017210608 | 12/2017 |
| WO | WO 2018023098 | 2/2018 |
| WO | WO 2018057912 | 3/2018 |
| WO | WO 2018095422 | 5/2018 |
| WO | WO 2018227132 | 12/2018 |
| WO | WO 2019044946 | 3/2019 |
| WO | WO 2019136298 | 7/2019 |
| WO | WO 2019140271 | 7/2019 |

(56) References Cited

FOREIGN PATENT DOCUMENTS

| WO | WO 2019219891 | 11/2019 |
|---|---|---|
| WO | WO 2019236954 | 12/2019 |
| WO | WO 2020160009 | 8/2020 |
| WO | WO 2021007402 | 1/2021 |
| WO | WO 2021007435 | 1/2021 |
| WO | WO 2022150596 | 7/2022 |

OTHER PUBLICATIONS

Aiello et al., "Abstract #6249: CBX-12: A low pH targeting alphalex™-exatecan conjugate for the treatment of solid tumors," Poster, presented at the AACR Annual Meeting 2020, Philadelphia, PA, Apr. 27-28, 2020 and Jun. 22-24, 2020, 1 page.

Aiello et al., "Abstract #63: Development of tumor-targeted PARP inhibitors for the treatment of solid cancers," Poster, presented at the Dublin, Ireland meeting "Molecular Targets and Cancer Therapeutics," Dublin, Ireland, Nov. 13, 2018, 1 page.

Anderson et al., "Protease-Sensitive Nanomaterials for Cancer Therapeutics and Imaging," Ind. Eng. Chem Res., Apr. 2017, 56(20):5761-5777.

Atzrodt et al., "The Renaissance of H/D Exchange," Angewandte Chemie International Edition, Oct. 2007, 46(41):7744-7765.

Bargh et al., "Cleavable linkers in antibody-drug conjugates," Chem. Soc. Rev., Aug. 2019, 48(16):4361-4374, 15 pages.

Berge et al., "Pharmaceutical Salts," Journal of Pharmaceutical Sciences, Jan. 1977, 66(1):1-19.

Burns et al., "Inhibition of Cancer Cell Proliferation and Breast Tumor Targeting of pHLIP-Monomethyl Auristatin E Conjugates," Mol. Pharmaceutics, Mar. 2015, 9 pages.

Burns et al., "Therapeutic Efficacy of a Family of pHLIP-MMAF Conjugates in Cancer Cells & Mouse Models," Mol. Pharmaceutics, Jan. 2017, 31 pages.

Caculitan et al., "Cathepsin B Is Dispensable for Cellular Processing of Cathepsin B-Cleavable Antibody-Drug Conjugates," Cancer Res., Dec. 2017, 77(24):7027-7037.

Catcott et al., "Microscale screening of antibody libraries as maytansinoid antibody-drug conjugates," mAbs, Jan. 2016, 8(3):513-523.

Catsburg et al., "Adherence to cancer prevention guidelines and risk of breast cancer," International Journal of Cancer, 2014, 135:2444-2452.

Chang et al., "Stapled α-helical peptide drug development: A potent dual inhibitor of MDM2 and MDMX for p53-dependent cancer therapy," Proceedings of the National Academy of Sciences, Sep. 2013, 110(36):E3445-E3454.

Cheng et al., "MicroRNA silencing for cancer therapy targeted to the tumor microenvironment," Nature, Feb. 2015, 518:107-110.

Choi et al., "Protease-Activated Drug Development," Theranostics, Feb. 2012, 2(2):156-178.

CO Office Action in Colombia Appln. No. NC2020/0009665, dated Sep. 26, 2022, 21 pages (with English translation).

Corso et al., "Innovative Linker Strategies for Tumor-Targeted Drug Conjugates," Chem. Eur. J., Nov. 2019, 25(65):14740-14757, 17 pages.

Dahan et al., "Dipeptidyl Peptidase IV as a Potential Target for Selective Prodrug Activation and Chemotherapeutic Action in Cancers," Mol. Pharmaceutics, Nov. 2014, 11(12):4385-4394.

De Marco, "Recombinant polypeptide production in E. coli: towards a rational approach to improve the yields of functional proteins," Microbial Cell Factories, Nov. 2013, 12(1):101, 8 pages.

Diez-Torrubia et al., "Application of the Dipeptidyl Peptidase IV (DPPIV/CD26) Based Prodrug Approach to Different Amine-Containing Drugs," J. Med. Chem. 2010, 53(2):559-572.

Diez-Torrubia et al., "Dipeptidyl Peptidase IV (DPPIV/CD26)-Based Prodrugs of Hydroxy-Containing Drugs," ChemMedChem, Apr. 2012, 7(4):618-628.

Dougherty et al., "Enhancing the Cell Permeability of Stapled Peptides with a Cyclic Cell-Penetrating Peptide," Journal of Medicinal Chemistry, Oct. 2019, 62(22):10098-10107.

Dougherty et al., "Understanding Cell Penetration of Cyclic Peptides," Chemical Reviews, May 2019, 119(17):47 pages.

Ducret, "Lipase-catalyzed enantioselective esterification of ibuprofen in organic solvents under controlled water activity," Enzyme and Microbial Technology, Mar. 1998, 22(4):212-216.

Fan et al, "Going Beyond Common Drug Metabolizing Enzymes: Case Studies of Biotransformation Involving Aldehyde Oxidase, g-Glutamyl Transpeptidase, Cathepsin B, Flavin-Containing Monooxygenase, and ADP-Ribosyltransferase," Drug Metabolism and Disposition, Aug. 2016, 44(8):1253-1261.

Fang, "Development of Synthetic Lethality Anticancer Therapeutics," J. Med. Chem., Jun. 2014, 57:7859-7873.

Garcia-Aparicio et al., "Design and Discovery of a Novel Dipeptidyl-peptidase IV (CD26)-Based Prodrug Approach," J. Med. Chem., Aug. 2006, 49(17):5339-5351.

Gayle et al., "Abstract #6242: Development of alphalex™-toxin low pH targeting conjugates for the treatment of solid tumors," Abstract, Cancer Research, Aug. 2020, 80(16): 3 pages, URL <https://cancerres.aacrjournals.org/content/80/16_Supplement/6242.short>.

Gayle et al., "Abstract #6242: Development of alphalex™-toxin low pH targeting conjugates for the treatment of solid tumors," Poster, presented at the AACR Annual Meeting 2020, Philadelphia, PA, Apr. 27-28, 2020 and Jun. 22-24, 2020, 1 page.

Grinda et al., "A self-immolative dendritic glucuronide prodrug of doxorubicin," Med. Chem. Commun., 2012, 3:68-70.

Guerlavais et al., "Advancements in Stapled Peptide Drug Discovery & Development," Annual Reports in Medicinal Chemistry, Jan. 2014, 49:331-345.

Harris, "Hypoxia—a key regulatory factor in tumour growth," Nat Rev Cancer, Jan. 2002, 2(1):38-47.

Hegan et al., "Inhibition of poly(ADP-ribose) polymerase downregulates BRCA1 and RAD51 in a pathway mediated by E2F4 and p130," PNAS, Feb. 2010, 107(5):2201-2206.

Herceg et al., "Design, synthesis and in vitro evaluation of β-glucuronidase-sensitive prodrug of 5-aminolevulinic acid for photodiagnosis of breast cancer cells," Bioorganic Chemistry, Aug. 2018, 78:372-380.

International Preliminary Report on Patentability in International Appln. No. PCT/US2019/012413, mailed Jul. 16, 2020, 8 pages.

International Preliminary Report on Patentability in International Appln. No. PCT/US2020/041348, mailed Jan. 20, 2022, 8 pages.

International Preliminary Report on Patentability in International Appln. No. PCT/US2020/041411, mailed Jan. 20, 2022, 8 pages.

International Search Report and Written Opinion in International Appln. No. PCT/US2019/012413, dated Mar. 26, 2019, 19 pages.

International Search Report and Written Opinion in International Appln. No. PCT/US2020/041348, dated Oct. 15, 2020, 16 pages.

International Search Report and Written Opinion in International Appln. No. PCT/US2020/041411, mailed Nov. 10, 2020, 17 pages.

International Search Report and Written Opinion in International Appln. No. PCT/US2022/011629, mailed May 9, 2022, 22 pages.

International Search Report and Written Opinion in International Appln. No. PCT/US2022/079973, mailed Mar. 6, 2023, 15 pages.

Joubert et al., "Antibody-Drug Conjugates: The Last Decade," Pharmaceuticals, 2020, 13, 245, 31 pages.

JP Office Action in Japanese Appln. No. 2020-557122, dated Nov. 22, 2022, 9 pages (with English translation).

Kalafatovic et al., "MMP-9 triggered self-assembly of doxorubicin nanofiber depots halts tumor growth," Biomaterials, Aug. 2016, 98:192-202.

Karabadzhak et al., "pHLIP-FIRE, a Cell Insertion-Triggered Fluorescent Probe for Imaging Tumors Demonstrates Targeted Cargo Delivery In Vivo," ACS Chem. Biol., Sep. 2014, 9(11):2545-2553.

Kerekes et al., "Aurora Kinase Inhibitors Based on the Imidazo[1,2-a]pyrazine Core: Fluorine and Deuterium Incorporation Improve Oral Absorption and Exposure," Journal of Medicinal Chemistry, Jan. 2011, 54(1):201-210.

Kim et al., "Matrix metalloproteinase-inspired suicidal treatments of diabetic ulcers with siRNA-decorated nanofibrous meshes," Gene Therapy, Apr. 2013, 20:378-385.

Kleiner-Grote et al., "Secretion of recombinant proteins from E. coli," Engineering in Life Sciences, Aug. 2018, 18(8):532-550.

(56) References Cited

OTHER PUBLICATIONS

Kolakowski et al., "The Methylene Alkoxy Carbamate Self-Immolative Unit: Utilization for the Targeted Delivery of Alcohol-Containing Payloads with Antibody-Drug Conjugates," Angew. Chem. Int. Ed., Jul. 2016, 55(28):7948-7951.
Kostova et al., "The Chemistry Behind ADCs," Pharmaceuticals, May 2021, 14(5), 442, 46 pages.
Kumar et al., "Lipase catalysis in organic solvents: advantages and applications," Biol. Proced. Online, Jan. 2016, 18(2):11 pages.
Kumazawa et al., "Potent and broad antitumor effects of DX-8951f, a water-soluble camptothecin derivative, against various human tumors xenografted in nude mice," Cancer Chemotherapy and Pharmacology, Jul. 1998, 42(3):210-220.
Kurth et al., "A thioxanone-based chiral template: asymmetric induction in the [2,3]-sigmatropic rearrangement of sulfur ylides. Enantioselective preparation of C.beta.-chiral pent-4-enoic acids," J. Org. Chem., Apr. 1990, 55(8):2286-2288.
Lewis Phillips et al., "Targeting HER2-Positive Breast Cancer with Trastuzumab-DM1, an Antibody-Cytotoxic Drug Conjugate," Cancer Research, Nov. 2008, 68(22):9280-9290.
Li et al., "Synthesis and Evaluation of Camptothecin Antibody-Drug Conjugates," ACS Medicinal Chemistry Letters, Sep. 2019, 10(10):1386-1392.
Li et al., "Topoisomerase I in Human Disease Pathogenesis and Treatments," Genomics, Proteomics & Bioinformatics, Jun. 2016, 14(3):166-171.
Lopus, "Antibody-DM1 conjugates as cancer therapeutics," Cancer Letters, Aug. 2011, 307(2):113-118.
Lu et al., "Linkers Having a Crucial Role in Antibody-Drug Conjugates," Int. J. Mol. Sci., Apr. 2016, 17(4):1-22.
Mckertish et al., "Advances and Limitations of Antibody Drug Conjugates for Cancer," Biomedicines, Jul. 2021, 9(8):872, 25 pages.
Merrifield, "Solid Phase Peptide Synthesis. I. The Synthesis of a Tetrapeptide," Journal of the American Chemical Society, Jul. 1963, 85(14):2149-2154.
Miletic et al., "Immobilization of Candida antarctica lipase B on polystyrene nanoparticles," Macromolecular Rapid Communications, Jan. 2010, 31(1):71-74.
Mistry et al., "Clinical Advances of Hypoxia-Activated Prodrugs in Combination With Radiation Therapy," International Journal of Radiation: Oncology Biology Physics, Aug. 2017, 98(5):1183-1196.
Monaco et al., "Catalytic Asymmetric Synthesis of Thiols," Journal of the American Chemical Society, Nov. 2014, 136(49):4 pages.
Moshinikova et al., "Antiproliferative Effect of pHLIP-Amanitin," Biochemistry, Jan. 2013, 52(7):1171-1178.
Nakada et al., "Novel antibody drug conjugates containing exatecan derivative-based cytotoxic payloads," Bioorganic & Medicinal Chemistry Letters, Mar. 2016, 26(6):4 pages.
Nguyen et al., "A Novel Soluble Peptide with pH-Responsive Membrane Insertion," Biochemistry, Oct. 2015, 54(43):6567-6575.
Office Action in Singapore Appln. No. 11202200132S, dated Aug. 15, 2023, 8 pages.
Office Action in Singapore Appln. No. 11202200134V, dated Aug. 14, 2023, 10 pages.
Ogitani et al., "Wide application of a novel topoisomerase I inhibitor-based drug conjugation technology," Bioorganic & Medicinal Chemistry Letters, Oct. 2016, 26(20):5069-5072.
Pacher et al., "Role of Poly(ADP-ribose) polymerase 1 (PARP-1) in Cardiovascular Diseases: The Therapeutic Potential of PARP Inhibitors," Cardiovasc Drug Rev., Oct. 2007; 25(3): 235-260.
PARP Inhibitors for Cancer Therapy, Cancer Drug Discovery and Development, vol. 83, Curtin and Sharma (ed)., 2015, Part V, 475-579.
Pétursson, "Protecting Groups in Carbohydrate Chemistry," Journal of Chemical Education, Nov. 1997, 74(11):1297-1303.
Reagan-Shaw et al., "Dose translation from animal to human studies revisited," The FASEB Journal, Mar. 2008, 22(3):659-661.
Simplicio et al., "Prodrugs for Amines," Molecules, Mar. 2008, 13(3):519-547.
Son et al., "Therapeutic Effect of pHLIPmediated CEACAM6 Gene Silencing in Lung Adenocarcinoma," Scientific Reports, Sep. 2019, 9(1):11607, 11 pages.
Sugimori et al., "Synthesis and Antitumor Activity of Ring A- and F-Modified Hexacyclic Camptothecin Analogues," J. Med. Chem., Jun. 1998, 41(13):2308-2318.
Tahara et al., "The Use of Olaparib (AZD2281) Potentiates SN-38 Cytotoxicity in Colon Cancer Cells by Indirect Inhibition of Rad51-Mediated Repair of DNA Double-Strand Breaks," Molecular Cancer Therapeutics, May 2014, 13(5):1170-1180.
Tangutur, "Microtubule Targeting Agents as Cancer Chemotherapeutics: An Overview of Molecular Hybrids as Stabilizing and Destabilizing Agents," Curr Top Med Chem, Sep. 2017, 17(22):2523-2537.
Tannock et al., "Acid pH in tumors and its potential for therapeutic exploitation," Cancer Res., Aug. 1989, 49(16):4373-4384, 13 pages.
Tesauro et al., "Peptide-Based Drug-Delivery Systems in Biotechnological Applications: Recent Advances and Perspectives," Molecules, Jan. 2019, 24(2):27 pages.
Vasquez-Montes et al., "Divalent Cations and Lipid Composition Modulate Membrane Insertion and Cancer-Targeting Action of pHLIP," Journal of Molecular Biology, Dec. 2019, 431(24):5004-5018.
Vrettos et al., "On the design principles of peptide-drug conjugates for targeted drug delivery to the malignant tumor site," Beilstein J. Org. Chem., Apr. 2018, 14:930-954.
Wang et al., "Development and Characterization of a Novel Peptide-Drug Conjugate with DM1 for Treatment of FGFR2-Positive Tumors," Biomedicines, Jul. 2021, 9(8):849, 14 pages.
Weerakkody et al., "Family of pH (low) insertion peptides for tumor targeting," Proceedings of the National Academy of Sciences, Apr. 2013, 110(15):5834-5839.
White et al., "Discovery of an SSTR2-Targeting Maytansinoid Conjugate (PEN-221) with Potent Activity in Vitro and in Vivo," J. Med. Chem., Mar. 2019, 62(5):2708-2719.
Wickstrom et al., "Melflufen—a peptidase-potentiated alkylating agent in clinical trials," Oncotarget, Sep. 2017, 8(39):66641-66655.
Widdison et al., "Semisynthetic Maytansine Analogues for the Targeted Treatment of Cancer," Journal of Medicinal Chemistry, Jun. 2006, 49(14):4392-4408.
Wyatt et al., "Peptides of pHLIP family for targeted intracellular and extracellular delivery of cargo molecules to tumors," Proceedings of the National Academy of Sciences, Mar. 2018, 115(12):E2811-E2818.
Xu et al., "Design, synthesis and biological evaluation of deuterated nintedanib for improving pharmacokinetic properties," Journal of Labelled Compounds and Radiopharmaceuticals, Jun. 2015, 58(7):308-312.
Yang et al., "Enzyme-mediated hydrolytic activation of prodrugs," Acta Pharamaceutica Sinica B, Oct. 2011, 1(3):143-159.
Yao et al., "MMP-Responsive 'Smart' Drug Delivery and Tumor Targeting," Trends in Pharmacological Sciences, Aug. 2018, 39(8):766-781.
Zdarta et al., "A General Overview of Support Materials for Enzyme Immobilization: Characteristics, Properties, Practical Utility," Catalysts, Feb. 2018, 8(92):1-27.
Zhang et al., "Design of acid-activated cell penetrating peptide for delivery of active molecules into cancer cells," Bioconjugate Chemistry, American Chemical Society, Jul. 2011, 22(7):1410-1415.
Zhang et al., "Linker Immolation Determines Cell Killing Activity of Disulfide-Linked Pyrrolobenzodiazepine Antibody-Drug Conjugates," ACS Medicinal Chemistry Letters, Aug. 2016, 7(11):6 pages.
Zhao et al., "Recombinant production of medium-to large-sized peptides in *Escherichia coli* using a cleavable self-aggregating tag," Microbial Cell Factories, Dec. 2016, 15(1):136, 9 pages.
Zhong et al., "Cathepsin B-cleavable doxorubicin prodrugs for targeted cancer therapy (Review)," International Journal of Oncology, Feb. 2013, 42(2):373-383.
Akaiwa et al., "Antibody-Drug Conjugate Payloads: Study of Auristatin Derivatives." Chem. Pharm. Bull., Mar. 2020, 68(3):201-211.

(56) References Cited

OTHER PUBLICATIONS

Gores et al., "Swelling, reductive stress, and cell death during chemical hypoxia in hepatocytes," Am. J. Physiol., Aug. 1989, 257(2):C347-C354.

Harms et al., "The pKa Values of Acidic and Basic Residues Buried at the Same Internal Location in a Protein Are Governed by Different Factors," J. Mol. Biol., May 2009, 389(1):34-47, 30 pages.

International Preliminary Report on Patentability in International Appln. No. PCT/US2022/071967, mailed on Nov. 9, 2023, 10 pages.

International Preliminary Report on Patentability in International Appln. No. PCT/US2022/079973, mailed May 30, 2024, 8 pages.

International Search Report and Written Opinion in International Appln. No. PCT/US2022/071967, mailed on Jul. 21, 2022, 19 pages.

Legarza et al., "Novel Camptothecin Derivatives," in vivo, Jan. 1, 2005, 19(1):283-92.

Liu et al., "Perspectives on Biologically Active Camptothecin Derivatives," Medicinal Research Reviews, Mar. 2015, 35(4):753-789, 38 pages.

Office Action in Chinese Appln. No. 202080057629.3, dated May 30, 2024, 16 pages (with English translation).

Office Action in Chinese Appln. No. 202080057842.4, dated Jul. 10, 2024, 32 pages (with machine translation).

Search Report in Malaysia Appln. No. PI2020003488, dated Nov. 23, 2023, 7 pages (with English translation).

Search Report in Taiwan Appln. No. 109123269, dated Mar. 6, 2024, 9 pages (with English translation).

Search Report in Taiwan Appln. No. 109123266, dated Mar. 5, 2024, 8 pages (with English translation).

Seeli et al., "Guar gum oleate-graft-poly(methacrylic acid) hydrogel as a colon-specific controlled drug delivery carrier," Carbohydrate Polymers, Feb. 2017, 158:51-57.

Sehn et al., "Polatuzumab Vedotin in Relapsed or Refractory Diffuse Large B-Cell Lymphoma," J. Clin. Oncol., Jan. 2020, 38(2):155-165, 22 pages.

Singhal et al., "Oxygen battle in the gut: Hypoxia and hypoxia-inducible factors in metabolic and inflammatory responses in the intestine," J. Biol. Chem., Jul. 2020, 295(30):10493-10505.

Venditto et al., "Cancer Therapies Utilizing the Camptothecins: A review of the in vivo literature," Molecular pharmaceutics, Apr. 5, 2010, 7(2):307-49.

Zeng et al., "Hypoxia-activated prodrugs and redox-responsive nanocarriers," Int. J. Nanomed., Oct. 2018, 13:6551-6574.

\* cited by examiner

PEPTIDE CONJUGATES OF MICROTUBULE-TARGETING AGENTS AS THERAPEUTICS

CROSS-REFERENCE TO RELATED APPLICATIONS

This application is a continuation of U.S. application Ser. No. 16/924,445, filed Jul. 9, 2020 (now U.S. Pat. No. 11,555,019), which claims the benefit of U.S. Provisional Application Ser. No. 63/041,324 filed Jun. 19, 2020 and U.S. Provisional Application Ser. No. 62/872,638 filed Jul. 10, 2019, which are incorporated herein by reference in their entirety.

FIELD OF THE INVENTION

The present invention relates to peptide conjugates of microtubule-targeting agents such as maytansinoid derivatives which are useful for the treatment of diseases such as cancer.

SEQUENCE LISTING

This application contains a Sequence Listing that has been submitted electronically as an XML file named 43236-0008002_SL_ST26.xml. The XML file, created on Feb. 24, 2023, is 416,890 bytes in size. The material in the XML file is hereby incorporated by reference in its entirety.

BACKGROUND OF THE INVENTION

Cancer is a group of diseases characterized by aberrant control of cell growth. The annual incidence of cancer is estimated to be in excess of 1.6 million in the United States alone. While surgery, radiation, chemotherapy, and hormones are used to treat cancer, it remains the second leading cause of death in the U.S. It is estimated that about 600,000 Americans will die from cancer each year.

Treatment of cancer in humans by systemic administration of pharmaceutical agents often functions by slowing or terminating the uncontrolled replication that is a characteristic of cancer cells. One class of such agents is microtubule-targeting agents. Cell division requires formation of an intact mitotic spindle apparatus, composed of microtubules undergoing random length changes. The random length changes of microtubules is referred to as dynamic instability. Disruption of the dynamic instability of microtubules can lead to the suppression of further cell division. Drugs that target microtubules to suppress dynamic instability are currently used in the clinic as effective anticancer agents for a wide variety of cancers. See Lopus, M, Cancer Lett., 2011, 307(2): 113-118.

The maytansinoids, (e.g., mertansine, DM1, or DM4) are a class of microtubule-targeting agents that have emerged as potential clinical chemotherapeutics. See Lopus, M, Cancer Lett., 2011, 307(2): 113-118; and Widdison, W., J. Med. Chem. 2006, 49:4392-4408 Although DM1 has been shown to be effective in the treatment of several types of cancer, including lymphoma and breast cancer, toxic side effects such as peripheral neuropathy have hindered the clinical development of tubulin-targeting agents such as the maytansinoids. Preferential delivery of maytansinoid compounds, such as DM1, to diseased tissues could avoid these serious side effects. Thus, there is a need for more selective delivery of maytansinoid compounds to diseased tissue.

SUMMARY

The present disclosure provides, inter alia, a compound of Formula (I):

$$R^2\text{-L-}R^1 \quad (I)$$

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure also provides methods of treating a disease or condition (e.g., cancer) by administering to a human or other mammal in need of such treatment a therapeutically effective amount of a compound of the disclosure. In some embodiments, the disease or condition is characterized by acidic or hypoxic diseased tissues.

The present disclosure also provides use of a compound described herein in the manufacture of a medicament for use in therapy. The present disclosure also provides the compounds described herein for use in therapy.

The present disclosure also provides methods for synthesizing the compounds of the disclosure and intermediates useful in these methods.

DETAILED DESCRIPTION

Figure 1:
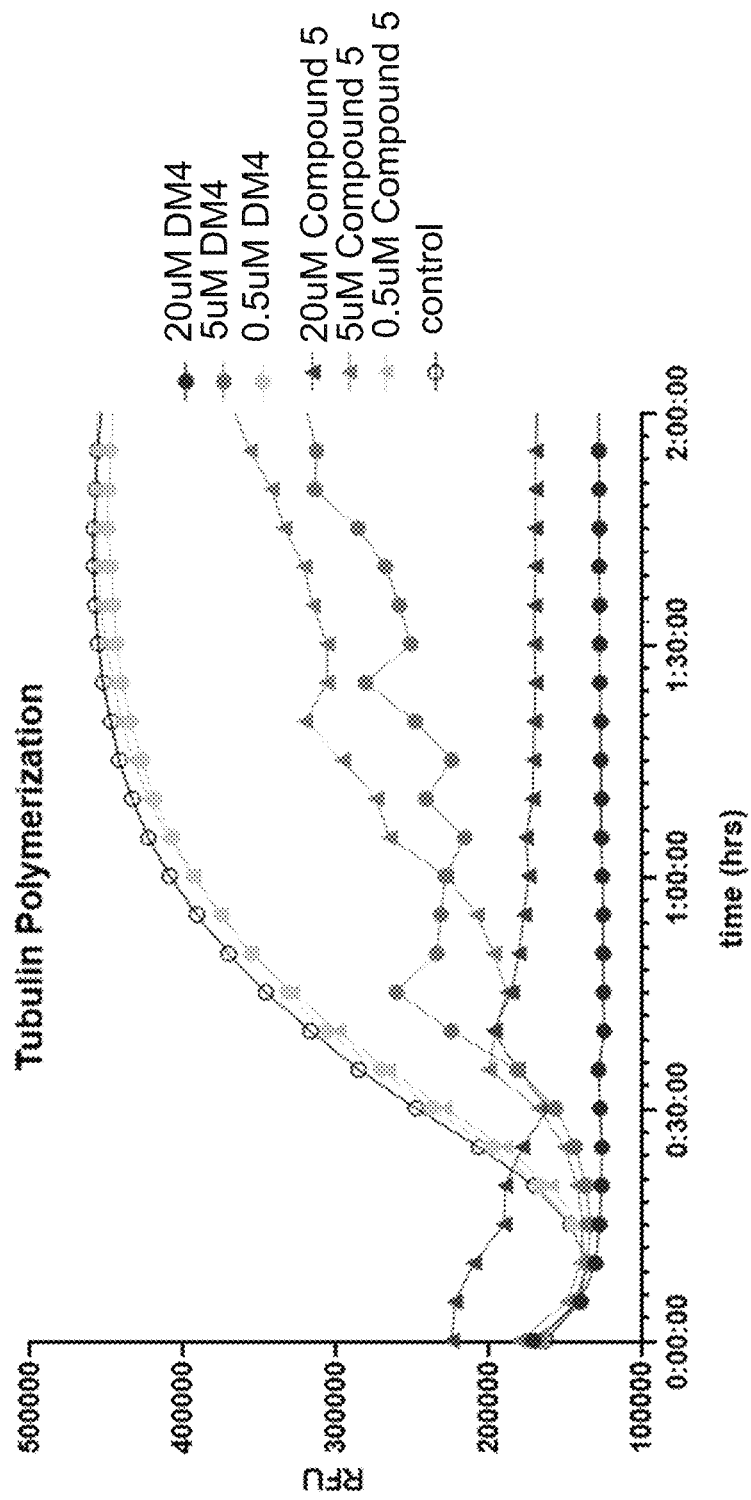
FIG. 1 shows a plot of the effect of free DM4 and Compound 5 on in vitro β-tubulin polymerization (in terms of relative fluorescence units) at various concentrations.

Provided herein is a compound of Formula (I):

$$R^2\text{-L-}R^1 \quad (I)$$

or a pharmaceutically acceptable salt thereof, wherein:
$R^1$ is a peptide;
$R^2$ is a small molecule microtubule targeting moiety; and
L is a linker, which is covalently linked to moiety $R^1$ and $R^2$.

Provided herein is a compound of Formula (I):

$$R^2\text{-L-}R^1 \quad (I)$$

or a pharmaceutically acceptable salt thereof, wherein:
$R^1$ is a peptide having 5 to 50 amino acids;
$R^2$ is a small molecule microtubule targeting moiety; and L is a linker, which is covalently linked to moiety $R^1$ and $R^2$.

Also provided herein is a compound of Formula (I):

$$R^2\text{-L-}R^1 \qquad (I)$$

or a pharmaceutically acceptable salt thereof, wherein:
- $R^1$ is a peptide capable of selectively delivering $R^2$L- across a cell membrane having an acidic or hypoxic mantle;
- $R^2$ is a small molecule microtubule targeting moiety; and
- L is a linker, which is covalently linked to moiety $R^1$ and $R^2$.

In some embodiments, $R^2$ is a maytansine-derived microtubule targeting moiety.

Provided herein is a compound of Formula (I):

$$R^2\text{-L-}R^1 \qquad (I)$$

or a pharmaceutically acceptable salt thereof, wherein:
- $R^1$ is a peptide capable of selectively delivering $R^2$L- across a cell membrane having an acidic or hypoxic mantle;
- $R^2$ is selected from the group consisting of:

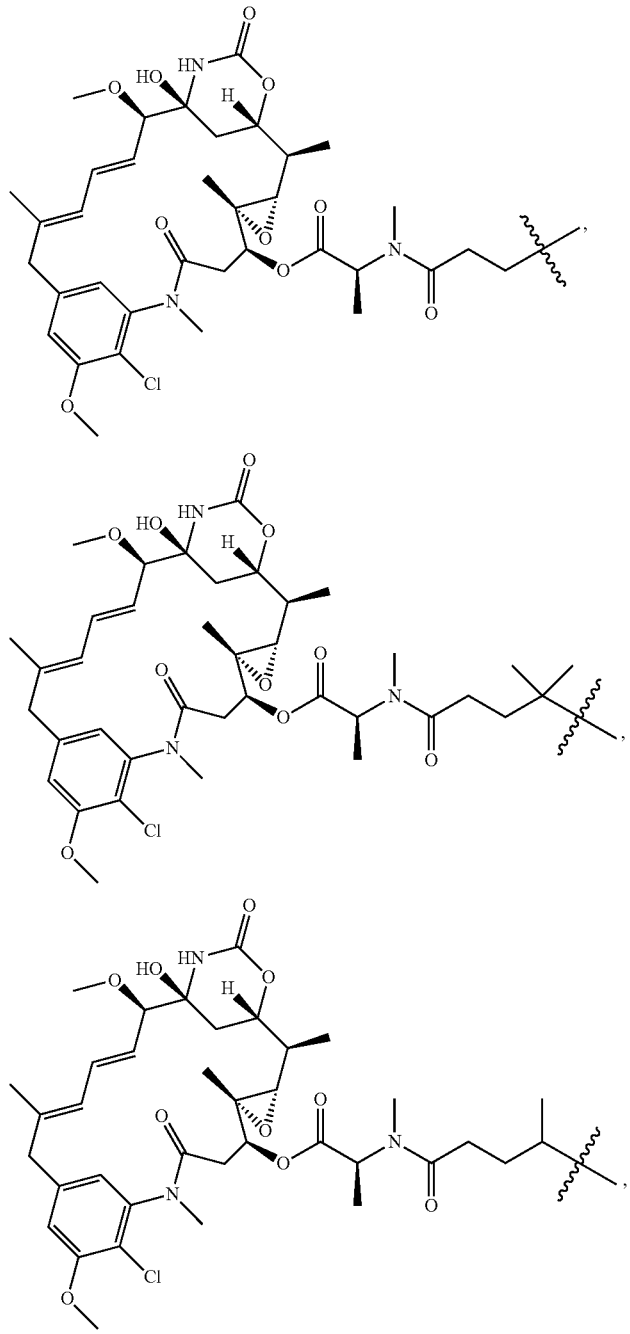

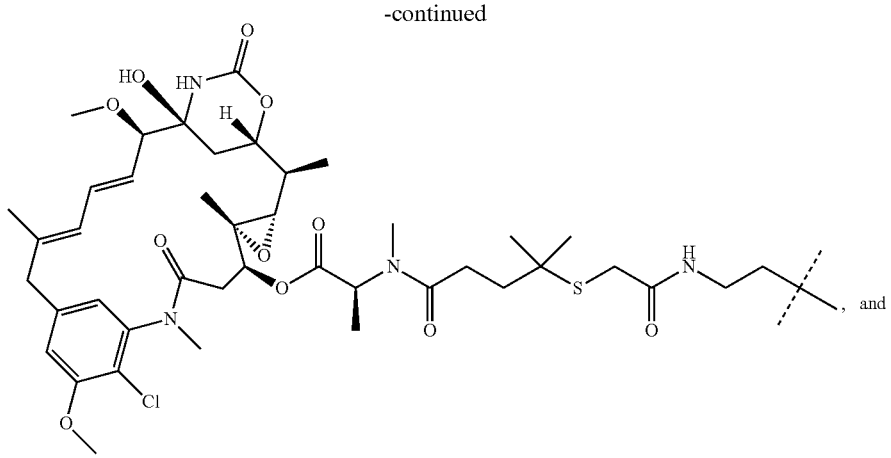

, and

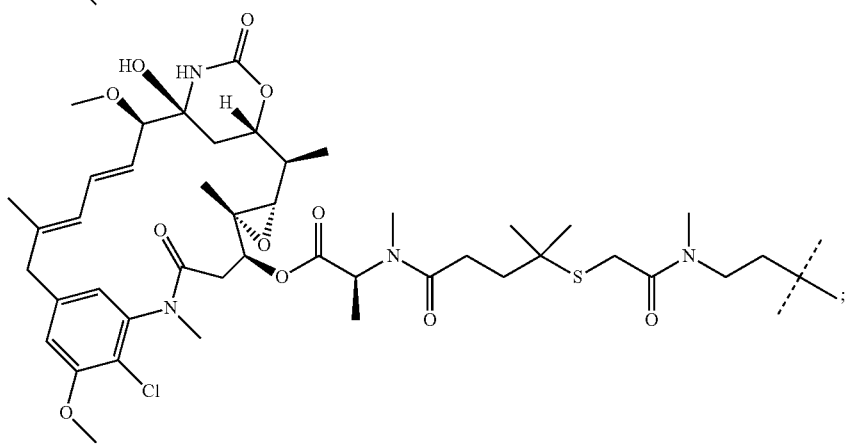

;

and

L is a linker, which is covalently linked to moiety $R^1$ and $R^2$.

Provided herein is a compound of Formula (I):

$$R^2\text{-L-}R^1 \quad (I)$$

or a pharmaceutically acceptable salt thereof, wherein:
- $R^1$ is a peptide capable of selectively delivering $R^2$L- across a cell membrane having an acidic or hypoxic mantle;
- $R^2$ is selected from the group consisting of:

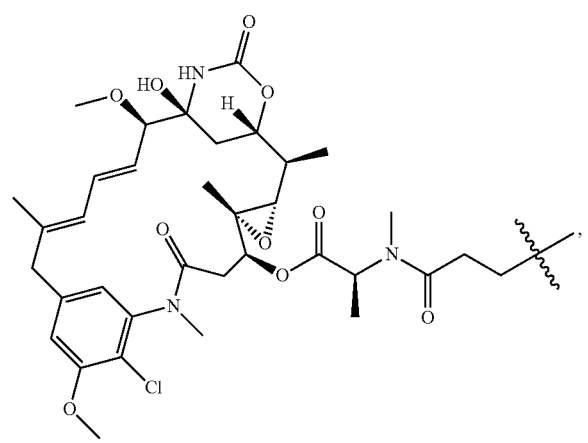

,

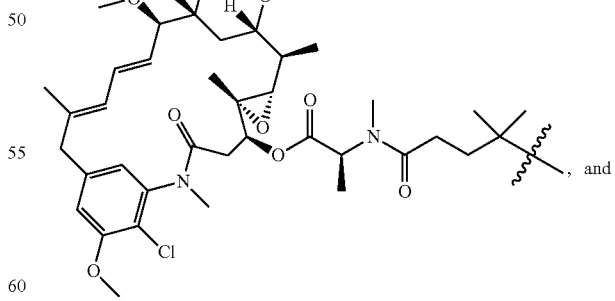

, and

-continued

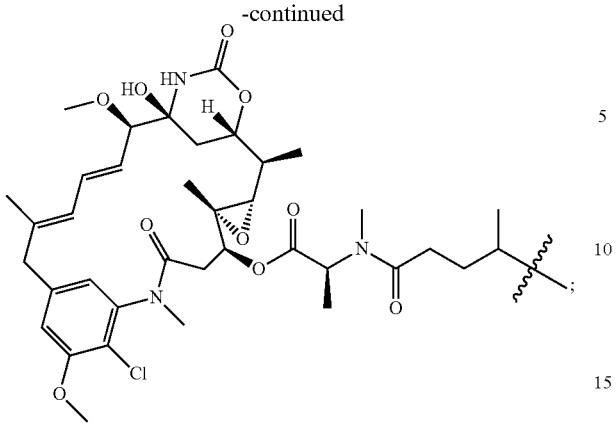
and
L is a linker, which is covalently linked to moiety $R^1$ and $R^2$.
Provided herein is a compound of Formula (I):
$$R^2\text{-L-}R^1 \qquad (I)$$
or a pharmaceutically acceptable salt thereof, wherein:
$R^1$ is a peptide capable of selectively delivering $R^2$L- across a cell membrane having an acidic or hypoxic mantle;
$R^2$ is selected from the group consisting of:
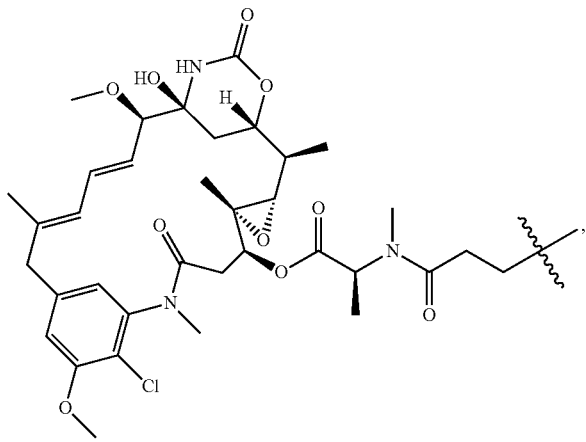
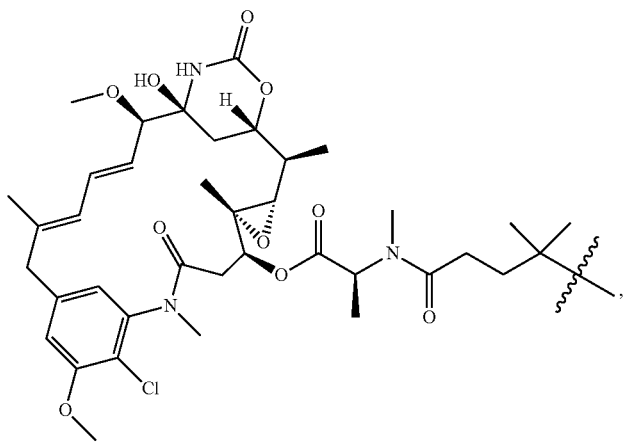

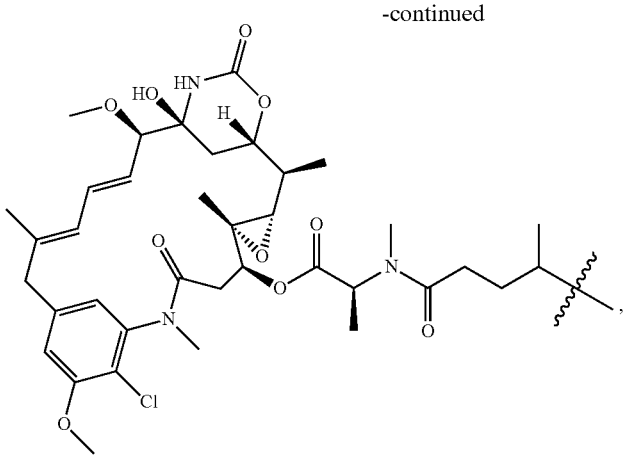
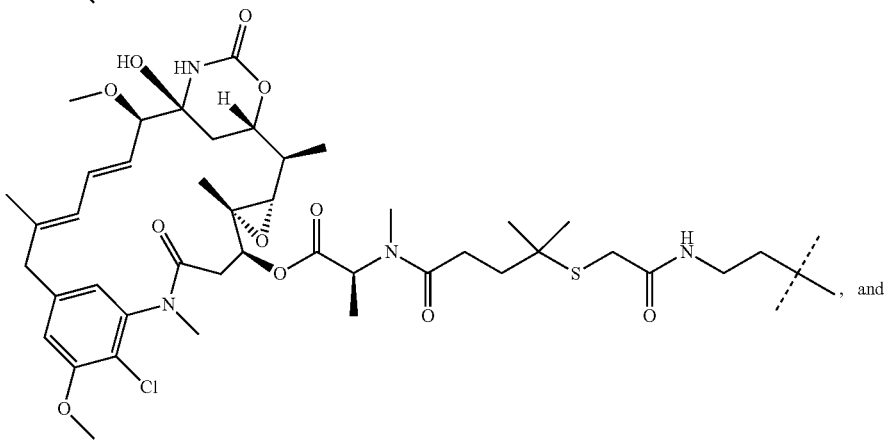
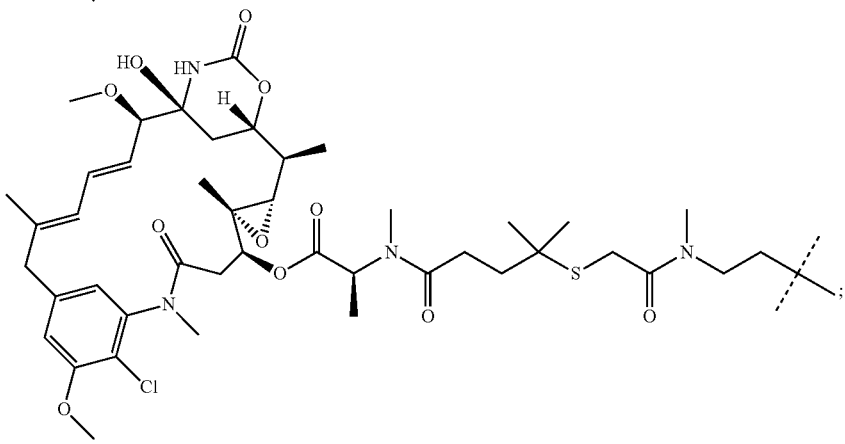
L is a group selected from:
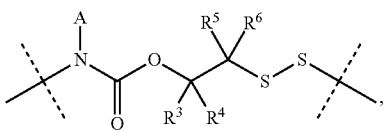
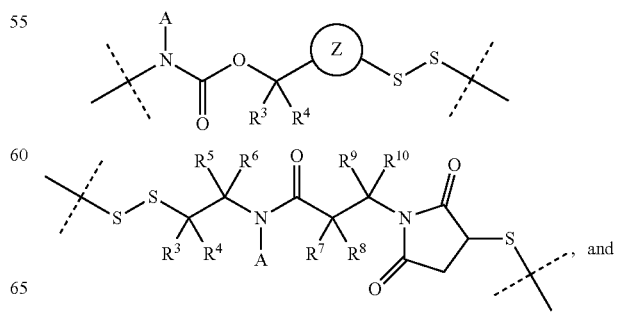

-continued

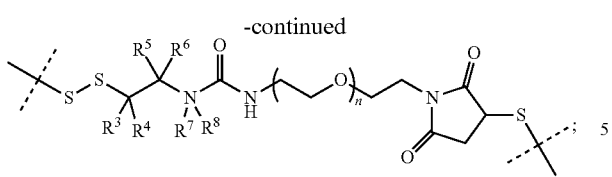

wherein
- $R^3$, $R^4$, $R^5$, $R^6$, $R^7$, $R^1$, $R^9$, and $R^{10}$ are each independently selected from H, $C_{1-4}$ alkyl, $C_{1-4}$ alkenyl, $C_{6-10}$ aryl, $C_{3-10}$ cycloalkyl, 5-10 membered heteroaryl, 4-10 membered heterocycloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$ wherein said $C_{1-4}$ alkyl, $C_{1-4}$ alkenyl, $C_{6-10}$ aryl, and 5-10 membered heteroaryl are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^3$ and $R^4$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^3$ and $R^4$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^4$ and $R^6$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^5$ and $R^6$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^7$ and $R^8$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^7$ and $R^9$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^8$ and $R^{10}$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- or $R^9$ and $R^{10}$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- Z is $C_{6-10}$ aryl or 5-10 membered heteroaryl; wherein the 5-10 membered heteroaryl has at least one ring-forming carbon atom and 1, 2, 3, or 4 ring-forming heteroatoms independently selected from N, O, and S, wherein the $C_{6-10}$ aryl and 5-10 membered heteroaryl are each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;
- A is H or $C_{1-4}$ alkyl;
- $R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH$; and
- n is 0, 1, or 2.

Provided herein is a compound of Formula (I):

$$R^2\text{-}L\text{-}R^1 \tag{I}$$

or a pharmaceutically acceptable salt thereof, wherein:
- $R^1$ is a peptide capable of selectively delivering $R^2L$- across a cell membrane having an acidic or hypoxic mantle;
- $R^2$ is selected from the group consisting of:

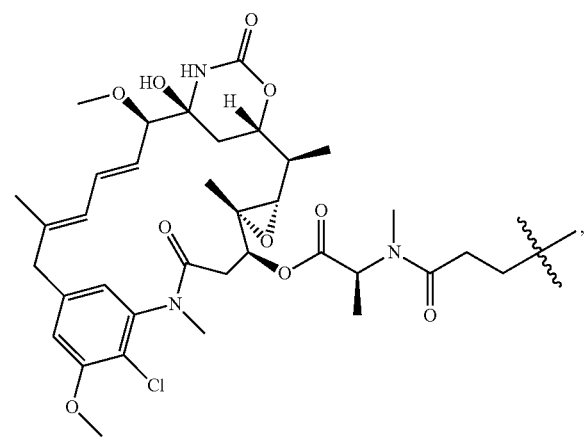

-continued

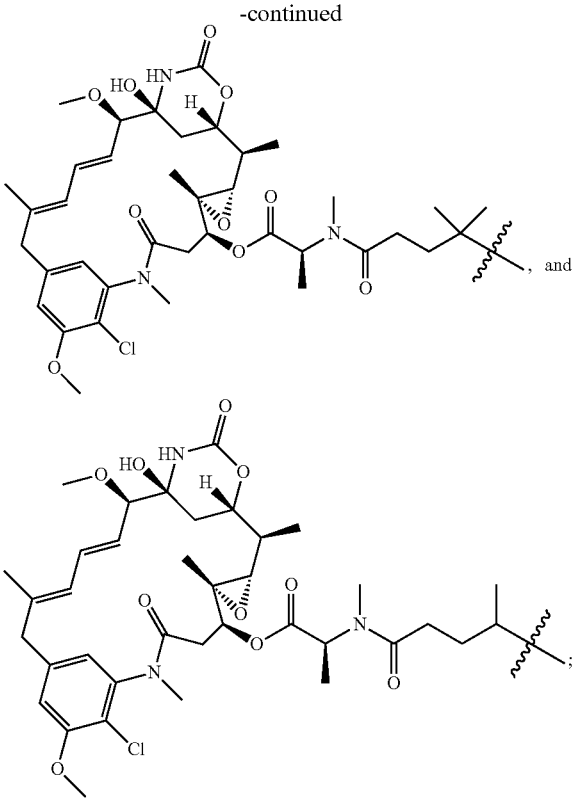

, and

;

L is a group selected from:

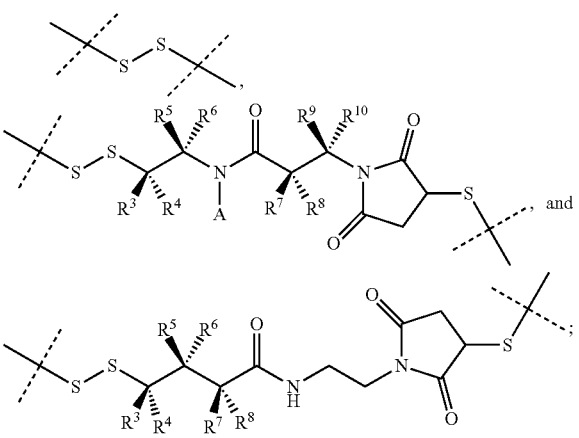

, and

;

wherein $R^3, R^4, R^5, R^6, R^7, R^8, R^9$, and $R^{10}$ are each independently selected from H, $C_{1-4}$ alkyl, $C_{1-4}$ alkenyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl, $C_{1-4}$ alkenyl, $C_{6-10}$ aryl, and 5-10 membered heteroaryl are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^3$ and $R^4$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^3$ and $R^5$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^4$ and $R^6$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^5$ and $R^6$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^7$ and $R^8$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^7$ and $R^9$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^8$ and $R^{10}$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^9$ and $R^{10}$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

A is H or $C_{1-4}$ alkyl; and $R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH$.

In some embodiments, the lefthand side of L attaches to $R^2$ and the righthand side of L attaches to $R^1$.

In some embodiments, a sulfur atom of the disulfide moiety of L is part of a cysteine residue of $R^1$.

As used herein, "peptide" refers to a targeting moiety comprising a 10-50 amino acid sequence, made up of naturally-occurring amino acid residues and optionally one or more non-naturally-occurring amino acids. In some embodiments, the peptide of R¹ is a peptide of 20 to 40, 20 to 30 amino acids, or 30 to 40 residues. Peptides suitable for use in the compounds of the invention are those that can insert across a cell membrane via a conformational change or a change in secondary structure in response to environmental pH changes. In this way, the peptide can target acidic tissue and selectively translocate polar, cell-impermeable molecules across cell membranes in response to low extracellular pH. In some embodiments, the peptide is capable of selectively delivering a conjugated moiety (e.g., R²L-) across a cell membrane having an acidic or hypoxic mantle having a pH less than about 6.0. In some embodiments, the peptide is capable of selectively delivering a conjugated moiety (e.g., R²L-) across a cell membrane having an acidic or hypoxic mantle having a pH less than about 6.5. In some embodiments, the peptide is capable of selectively delivering a conjugated moiety (e.g., R²L-) across a cell membrane having an acidic or hypoxic mantle having a pH less than about 5.5. In some embodiments, the peptide is capable of selectively delivering a conjugated moiety (e.g., R²L-) across a cell membrane having an acidic or hypoxic mantle having a pH between about 5.0 and about 6.0.

In certain embodiments, the peptide of R¹ includes a cysteine residue which can form the site of attachment to a payload moiety (e.g., R²L-) to be delivered across a cell membrane. In some embodiments, R¹ is attached to L through a cysteine residue of R¹. In some embodiments, the sulfur atom of the cysteine residue can form part of the disulfide bond of the disulfide bond-containing linker L.

Suitable peptides, that can conformationally change based on pH and insert across a cell membrane, are described, for example, in U.S. Pat. Nos. 8,076,451 and 9,289,508 (each of which is incorporated herein by reference in its entirety). Other suitable peptides are described, for example, in Weerakkody, et al., PNAS 110 (15), 5834-5839 (Apr. 9, 2013), which is also incorporated herein by reference in its entirety.

In some embodiments, R¹ is a peptide comprising at least one of the following sequences:

```
                                   (SEQ ID NO. 1; Pv1)
ADDQNPWRAYLDLLFPTDTLLLDLLWCG, (SEQ ID NO. 2; Pv2)
AEQNPIYWARYADWLFTTPLLLLDLALLVDADECG,
and (SEQ ID NO. 3; Pv3)
ADDQNPWRAYLDLLFPTDTLLLDLLWDADECG;

(SEQ ID NO. 4; Pv4)
Ac-AAEQNPIYWARYADWLFTTPLLLLDLALLVDADEGTKCG;

(SEQ ID No. 5; Pv5)
AAEQNPIYWARYADWLFTTPLLLLDLALLVDADEGTC;
and (SEQ ID No. 6; Pv6)
AAEQNPIYWWARYADWLFTTPLLLLDLALLVDADEGTCG;
``` wherein R¹ is attached to L through a cysteine residue of R¹.

In some embodiments, Ri is a peptide comprising at least one of the following sequences:

```
                                   (SEQ ID NO. 1; Pv1)
ADDQNPWRAYLDLLFPTDTLLLDLLWCG, (SEQ ID NO. 2; Pv2)
AEQNPIYWARYADWLFTTPLLLLDLALLVDADECG,
and (SEQ ID NO. 3; Pv3)
ADDQNPWRAYLDLLFPTDTLLLDLLWDADECG;
and (SEQ ID No. 6; Pv6)
AAEQNPIYWWARYADWLFTTPLLLLDLALLVDADEGTCG;
``` wherein R¹ is attached to L through a cysteine residue of R¹.

In some embodiments, R¹ is a peptide comprising the sequence

```
                                   (SEQ ID NO. 1; Pv1)
ADDQNPWRAYLDLLFPTDTLLLDLLWCG.
```

In some embodiments, R¹ is a peptide comprising the sequence

```
                                   (SEQ ID NO. 2; Pv2)
AEQNPIYWARYADWLFTTPLLLLDLALLVDADECG.
```

In some embodiments, R¹ is a peptide comprising the sequence

```
                                   (SEQ ID NO. 3; Pv3)
ADDQNPWRAYLDLLFPTDTLLLDLLWDADECG.
```

In some embodiments, R¹ is a peptide comprising the sequence

```
                                   (SEQ ID NO. 4; Pv4)
Ac-AAEQNPIYWARYADWLFTTPLLLLDLALLVDADEGTKCG.
```

In some embodiments, R¹ is a peptide comprising the sequence

```
                                   (SEQ ID NO. 5; Pv5)
AAEQNPIYWARYADWLFTTPLLLLDLALLVDADEGTC.
```

In some embodiments, R¹ is a peptide comprising the sequence

```
                                   (SEQ ID NO. 6; Pv6)
AAEQNPIYWWARYADWLFTTPLLLLDLALLVDADEGTCG.
```

In some embodiments, R¹ is a peptide consisting of the sequence

```
                                   (SEQ ID NO. 1; Pv1)
ADDQNPWRAYLDLLFPTDTLLLDLLWCG.
```

In some embodiments, R¹ is a peptide consisting of the sequence

```
                                   (SEQ ID NO. 2; Pv2)
AEQNPIYWARYADWLFTTPLLLLDLALLVDADECG.
```

In some embodiments, R¹ is a peptide consisting of the sequence

```
                                   (SEQ ID NO. 3; Pv3)
ADDQNPWRAYLDLLFPTDTLLLDLLWDADECG.
```

In some embodiments, R¹ is a peptide consisting of the sequence Ac-

AAEQNPIYWARYADWLFTTPLLLLDLALLVDADEGTKCG. (SEQ ID NO. 4; Pv4)

In some embodiments, R¹ is a peptide consisting of the sequence

AAEQNPIYWARYADWLFTTPLLLLDLALLVDADEGTC. (SEQ ID NO. 5; Pv5)

In some embodiments, R¹ is a peptide consisting of the sequence

AAEQNPIYWWARYADWLFTTPLLLLDLALLVDADEGTCG. (SEQ ID NO. 6; Pv6)

In some embodiments, R¹ is a peptide comprising at least one sequence selected from SEQ ID NO: 7 to SEQ ID NO: 311 as shown in Table 1.

In some embodiments, R¹ is a peptide consisting of a sequence selected from SEQ ID NO: 7 to SEQ ID NO: 311 as shown in Table 1.

TABLE 1

Additional R¹ Sequences

| SEQ ID NO. | Sequence |
|---|---|
| 7 | AEQNPIYWARYADWLFTTPLLLLDLALLVDADEGT |
| 8 | GGEQNPIYWARYADWLFTTPLLLLLDLALLVDADEGT |
| 9 | AEQNPIYWARYADWLFTTPLLLLLDLALLVDADEGT |
| 10 | AAEQNPIYWARYADWLFTTPLLLLLDLALLVDADEGTCG |
| 11 | GGEQNPIYWARYADWLFTTPLLLLLDLALLVDADEGTCG |
| 12 | ACEQNPIYWARYADWLFTTPLLLLLDLALLVDADEGTG |
| 13 | ACEQNPIYWARYADWLFTTPLLLLLDLALLVDADEGT |
| 14 | AKEQNPIYWARYADWLFTTPLLLLLDLALLVDADEGT |
| 15 | AAEQNPIYWARYADWLFTTPLLLLLDLALLVDADEGTKCG |
| 16 | AKEQNPIYWARYADWLFTTPLLLLLDLALLVDADECT |
| 17 | ACEQNPIYWARYANWLFTTPLLLLNLALLVDADEGTG |
| 18 | ACEQNPIYWARYAKWLFTTPLLLLKLALLVDADEGTG |
| 19 | GGEQNPIYWARYADWLFTTPLLLLDLALLVNANQGT |
| 20 | AAEQNPIYWARYADWLFTTPLLLLALALLVDADEGT |
| 21 | AAEQNPIYWARYAAWLFTTPLLLLDLALLVDADEGT |
| 22 | AAEQNPIYWARYADWLFTTALLLLDLALLVDADEGT |
| 23 | AAEQNPIYWARYADWLFTTPLLLLELALLVDADEGT |
| 24 | AAEQNPIYWARYAEWLFTTPLLLLDLALLVDADEGT |
| 25 | AAEQNPIIYWARYADWLFTDLPLLLLDLLALLVDADEGT |
| 26 | GEQNPIYWAQYADWLFTTPLLLLDLALLVDADEGTCG |
| 27 | GGEQNPIYWARYADWLFTTPLLLDLLALLVDADEGTCG |

TABLE 1-continued

Additional R¹ Sequences

| SEQ ID NO. | Sequence |
|---|---|
| 28 | GGEQNPIYWARYADWLFTTPLLLLLDALLVDADEGTCG |
| 29 | GGEQNPIYWARYDAWLFTTPLLLLDLALLVDADEGTCG |
| 30 | GGEQNPIYWARYAWDLFTTPLLLLDLALLVDADEGTCG |
| 31 | AAEQNPIYWARYADWLFTTGLLLLDLALLVDADEGT |
| 32 | DDDEDNPIYWARYADWLFTTPLLLLHGALLVDADECT |
| 33 | DDDEDNPIYWARYAHWLFTTPLLLLHGALLVDADEGCT |
| 34 | DDDEDNPIYWARYAHWLFTTPLLLLHGALLVNADECT |
| 35 | DDDEDNPIYWARYAHWLFTTPLLLLHGALLVNANECT |
| 36 | AEQNPIYWARYADFLFTTPLLLLDLALLVDADET |
| 37 | AEQNPIYFARYADWLFTTPLLLLDLALLVDADEGT |
| 38 | AEQNPIYFARYADFLFTTPLLLLDLALLWDADET |
| 39 | AKEDQNPYWARYADWLFTTPLLLLDLALLVDG |
| 40 | ACEDQNPYWARYADWLFTTPLLLLDLALLVDG |
| 41 | AEDQNPYWARYADWLFTTPLLLLDLALLVDCG |
| 42 | AEDQNPYWARYADWLFTTPLLLLELALLVECG |
| 43 | AKEDQNPYWRAYADLFTPLTLLDLLALWDG |
| 44 | ACEDQNPYWRAYADLFTPLTLLDLLALWDG |
| 45 | ACDDQNPWRAYLDLLFPTDTLLLDLLW |
| 46 | TEDADVLLALDLLLLPTTFLWD |
| 47 | AEQNPIYWARYADWLFTTPL |
| 48 | AEQNPIYWARYADWLFTTPCL |
| 49 | ACEQNPIYWARYADWLFTTPL |
| 50 | AEQNPIYFARYADWLFTTPL |
| 51 | KEDQNPWARYADLLFPTTLAW |
| 52 | ACEDQNPWARYADLLFPTTLAW |
| 53 | ACEDQNPWARYADWLFPTTLLLLD |
| 54 | ACEEQNPWARYAELLFPTTLAW |
| 55 | ACEEQNPWARYAEWLFPTTLLLLE |
| 56 | ACEEQNPWARYLEWLFPTETLLLEL |
| 57 | GGEQNPIY WARYADWLFTTPLLLLDLALLV DADEGT |
| 58 | ACEQNPIY WARYADWLFTTPLLLLDLALLV |
| 59 | WARYADWLFTTPLLLLDLALLV DADEGTCG |
| 60 | WARYADWLFTTPLLLLDLALLV DADEGCT |
| 61 | GGEQNPIY WARYADWLFTTPLLLLDLALLV DADEGTCG |
| 62 | ACEQNPIY WARYADWLFTTPLLLLDLALLV DADEGT |
| 63 | AKEQNPIY WARYADWLFTTPLLLLDLALLV DADEGT |
| 64 | AKEQNPIY WARYADWLFTTPLLLLDLALLV DADEGT |

TABLE 1-continued

Additional R¹ Sequences

| SEQ ID NO. | Sequence |
|---|---|
| 65 | AAEQNPIY WARYADWLFTTALLLLDLALLV DADEGT |
| 66 | ACAEQNPIY WARYADWLFTTGLLLLDLALLV DADEGT |
| 67 | AEQNPIY WARYADFLFTTALLLLDLALLV DADE_T |
| 68 | AEQNPIY FARYADWLFTTPLLLLDLALLV DADEGT |
| 69 | AEQNPIY FARYADFLFTTPLLLLDLALLV DADE_T |
| 70 | AKEDQNP_Y WARYADWLFTTPLLLLDLALLV DG____ |
| 71 | ACEDQNP_Y WARYADWLFTTPLLLLDLALLV DG____ |
| 72 | AEDQNP_Y WARYADWLFTTPLLLLDLALLV DG____ |
| 73 | AEDQNP_Y WARYADWLFTTPLLLLELALLV ECG___ |
| 74 | AKEDQNP_Y WRAYAD_LFT_PLTLLDLLALW DG____ |
| 75 | ACEDQNP_Y WRAYAD_LFT_PLTLLDLLALW DG____ |
| 76 | AKEDQNDP_Y WARYADWLFTTPLLLLDLALLV G_____ |
| 77 | TEDADVLLALDLLLLPTTFLWDAYRAWYPNQECA |
| 78 | GGEQNPIY WARYADWLFTTPLLLLDLALLV DADEGT |
| 79 | AEQNPIY WARYADWLFTTPL |
| 80 | AEQNPIY WARYADWLFTTPCL |
| 81 | ACEQNPIY WARYADWLFTTPL |
| 82 | ACEQNPIY FARYADWLFTTPL |
| 83 | ACDDQNP WRAYLDLLFPTDTLLLDLLW |
| 84 | ACEEQNP WRAYLELLFPTETLLLELLW |
| 85 | ACDDQNP WARYLDWLFPTDTLLLDL |
| 86 | CDNNNP WRAYLDLLFPTDTLLLDW |
| 87 | ACEEQNP WARYLEWLFPTETLLLEL |
| 88 | ACEDQNP WARYADWLFPTTLLLLD |
| 89 | ACEEQNP WARYAEWLFPTTLLLLE |
| 90 | ACEDQNP WARYADLLFPTTLAW |
| 91 | ACEDQNP WARYAELLFPTTLW |
| 92 | KEDQNP WARYADLLFPTTLW |
| 93 | DDDEDNP IYWARYAHWLFTTPLLLLHGALLVDADECT |
| 94 | DDDEDNPIYWARYAHWLFTTPLLLLDGALLVDADECT |
| 95 | DDDEDNPIYWARYAHWLFTTPLLLLHGALLVNADECT |
| 96 | DDDEDNPIYWARYAFIWLFTTPLLLLHGALLVNANECT |
| 97 | DDDEDNPIYWARYADWLFTTPLLLLHGALLVDADECT |
| 98 | ACEQNPIYWARYADWLFTTPLLLLDLALLVDADEGIG |
| 99 | ACEQNPIYWARYADWLFTTPLLLLDLALLVDADET |
| 100 | ACEQNPIYWARYADWLFTTPLLLLDLALLVDADEGT |
| 101 | GGEQNPIYWARYADWLFTTPLLLDLLALLVDADEGTCG |
| 102 | GGEQNPIYWARYADWLFTTPLLLLLDALLVDADEGTCG |
| 103 | GGEQNPIYWARYAWDLFTTPLLLLDLALLVDADEGTCG |
| 104 | AAEQNPIYWARYAEWLFTTPLLLLDLALLVDADEGTCG |
| 105 | AAEQNPIYWARYAEWLFTTPLLLLELALLVDADEGTCG |
| 106 | GGEQNPIYWARYDAWLFTTPLLLLDLALLVDADEGTCG |
| 107 | GGEQNPIYWAQYDAWLFTTPLLLLDLALLVDADEGTCG |
| 108 | GGEQNPIYWAQDYAWLFTTPLLLLDLALLVDADEGTCG |
| 109 | AAEQNPIYWARYAAWLFTTPLLLLDLALLVDADEGTCG |
| 110 | ACEQNPIYWARYANWLFTTPLLLLNLALLVDADEGTG |
| 111 | DDDEDNPIYWARYAFIWLFTTPLLLLHGALLVNANECT |
| 112 | DDDEDNPIYWARYAHWLFTTPLLLLHGALLVNADECT |
| 113 | DDDEDNPIYWARYADWLFTTPLLLLHGALLVDADECT |
| 114 | DDDEDNPIYWARYAHWLFTTPLLLLHGALLVDADECT |
| 115 | DDDEDNPIYWARYAHWLFTTPLLLLDGALLVDADECT |
| 116 | GGEQNPIYWARYADWLFTTPLLLLDLALLVNANQGT |
| 117 | AAEQNPIYWARYADWLFTTPLLLLELALLVDADEGTCG |
| 118 | AAEQNPIYWARYAEWLFTTPLLLLELALLVDADEGTCG |
| 119 | AAEQNPIYWARYADWLFTTPLLLLELALLVDADEGTKCG |
| 120 | GGEQNPIYWAQYDAWLFTTPLLLLDLALLVDADEGTCG |
| 121 | GGEQNPIYWAQYDAWLFTTPLLLLDLALLVDADEGTCG |
| 122 | GGEQNPIYWAQDYAWLFTTPLLLLDLALLVDADEGTCG |
| 123 | GGEQNPIYWARYADWLFTTPLLLLDALLVNANQGT |
| 124 | DDDEDNPIYWARYAHWLFTTPLLLLHGALLVNADECT |
| 125 | DDDEDNPIYWARYAHWLFTTPLLLLHGALLVNANECT |
| 126 | ACEQNPIYWARYAKWLFTTPLLLLKLALLVDADEGTG |
| 127 | GGEQNPIYWAQDYAWLFTTPLLLLDLALLVDADEGTCG |
| 128 | GGEQNPIYWAQYDAWLFTTPLLLLDLALLVDADEGTCG |
| 129 | GGEQNPIYWAQYADWLFTTPLLLLDLALLVDADEGTCG |
| 130 | AAEQNPIYWARYAAWLFTTPLLLLDLALLVDADEGTCG |
| 131 | AAEQNPIYWARYADWLFTDLPLLLLDLLALLVDADEGT |
| 132 | GGEQNPIYWARYADWLFTTPLLLLLDLALLVDADEGTCG |
| 133 | GGEQNPIYWARYADWLFTTPLLLDLLALLVDADEGTCG |
| 134 | AAEQNPIYWARYADWLFTTGLLLLDLALLVDADEGT |
| 135 | AEQNPIYWARYAAWLFTTPLLLLDLALLVDADEGTCG |
| 136 | GGEQNPIYWAQYDAWLFTTPLLLLDLALLVDADEGTCG |
| 137 | GGEQNPIYWAQDYAWLFTTPLLLLDLALLDADEGTCG |
| 138 | GGEQNPIYWARYDAWLFTTPLLLLDLALLVDADEGTCG |

TABLE 1-continued

Additional R¹ Sequences

| SEQ ID NO. | Sequence |
|---|---|
| 139 | AAEQNPIYWARYADWLFTTPLLLLALALLVDADEGTCG |
| 140 | AAEQNPIYWARYADWLFTTPLLLLDLALLVDADEGTKCG . . . EGTK(rhodamine)C(phalloidin)G |
| 141 | AAEQNPIYWARYADWLFTTPLLLLELALLDADEGTKCG |
| 142 | AAEQNPIYWARYADWLFTTPLLLLDLALLVDADEGTCG |
| 143 | AAEQNPIYWARYADWLFTTPLLLLDLALLVDADEGTC(phalloidin)G |
| 144 | GGEQNPIYWARYADWLFTTPLLLLDLALLVDADEGTCG |
| 145 | ACEQNPIYWARYADWLFTTPLLLLDLALLVDADET |
| 146 | ACEQNPIYWARYADWLFTTPLLLLDLALLVDADEGTG |
| 147 | ACEQNPIYWARYADWLFTTPLLLLDLALLVDADEGT |
| 148 | GGEQNPIYWARYADWLFTTPLLLLDLALLVNANQGT |
| 149 | DDDEDNPIYWARYAHWLFTTPLLLLHGALLVNADECT |
| 150 | DDDEDNPIYWARYAHWLFTTPLLLLHGALLVNANECT |
| 151 | GGEQNPIYWARYADWLFTTPLLLLDLALLVDADEGTCG |
| 152 | AAEQNPIYWARYADWLFTTPLLLLDLALLVDADEGTC(phalloidin)G |
| 153 | AAEQNPIYWARYADWLFTTPLLLLELALLVDADEGTKCG |
| 154 | AAEQNPIYWARYADWLFTTPLLLLDLALLVDADEGTKCG |
| 155 | DDDEDNPIYWARYAHWLFTTPLLLLBGALLVDADECT |
| 156 | DDDEDNPIYWARYAHWLFTTPLLLLDGALLVDADECT |
| 157 | DDDEDNPIYWARYAHWLFTTPLLLLBGALLVNADECT |
| 158 | DDDEDNPIYWARYAHWLFTTPLLLLBGALLVNANECT |
| 159 | DDDEDNPIYWARYADWLFTTPLLLLIBGALLVDADECT |
| 160 | DDDEDNPIYWARYADWTFTTPLLLLHGALLVDADECT |
| 161 | DDDEDNPIYWARYAHWLFTTPLLLLDGALLVDADECT |
| 162 | DDDEDNPIYWARYAHWLFTTPLLLLHGALLVDADECT |
| 163 | DDDEDNPIYWARYAHWLFTTPLLLLHGALLVNADECT |
| 164 | DDDEDNPIYWARYHWLFTTPLLLLHGALLVNANECT |
| 165 | DDDEDNPIYWARYAHWLFTTPLLLLHGALLVNANECT |
| 166 | DDDEDNPIYWARYAHWLFTTPLLLLHGALLVNADECT |
| 167 | DDDEDNPIYWARYADWLFTTPLLLLHGALLVDADECT |
| 168 | DDDEDNPIYWARYAHWLFTTPLLLLDGALLVDADECT |
| 169 | DDDEDNPIYWARYADWLFTTPLLLLLDGALLVDADECT |
| 170 | GGEQNPIYWARYADWLFTTPLLLLDLALLVNANQGT |
| 171 | DDDEDNPIYWARYAHWLFTTPLLLLHGALLVNADECT |
| 172 | DDDEDNPIYWARYAHWLFTTPLLLLHGALLVDADECT |
| 173 | DDDEDNPIYWARYAHWLFTTPLLLLHGALLVDADECT |
| 174 | DDDEDNPIYWARYAHMLFTTPLLLLDGALLVDADECT |
| 175 | DDDEDNPIYWARYAHWLFTTPLLLLHGALLVNANECT |
| 176 | DDDEDNPIYWARYAHWLFTTPLLLLDGALLVDADECT |
| 177 | DDDEDNPIYWARYADWLFTTPLLLLHGALLVDADECT |
| 178 | DDDEDNPIYWARYAHWLFTTPLLLLHGALLVDADECT |
| 179 | DDDEDNPIYWARYAHWLFTTPLLLLHGALLVNADECT |
| 180 | DDDEDNPIYWARYAHWLFTTPLLLLHGALLVNANECT |
| 181 | AAEQNPIYWARYADWLFTTGLLLLDLALLVDADEGT |
| 182 | GGEQNPIYWARYAWDLFTTPLLLLDLALLVDADEGTCG |
| 183 | GGEQNPIYWARYDAWLFTTPLLLLDLALLVDADEGTCG |
| 184 | GGEQNPIYWAQYDAWLFTTPLLLLDLALLVDADEGTCG |
| 185 | GGEQNPIYWAQDYAWLFTTPLLLLDLALLVDADEGTCG |
| 186 | AAEQNPIYWARYAAWLFTTPLLLLDLALLVDADEGTCG |
| 187 | GGEQNPIYWARYADWLFTTPLLLLDALLVDADEGTCG |
| 188 | GGEQNPIYWARYADWLFTTPLLLDLLALLVDADEGTCG |
| 189 | GGEQNPIYWARYADWLFTTPLLLLDLLALLVDADEGTCG |
| 190 | GGEQNPIYWARYADWLFTTPLLLLLDALLVDADEGTCG |
| 191 | GGEQNPIYWAQYADWLFTTPLLLLDLALLVDADEGTCG |
| 192 | GGEQNPIYWAQYDAWLFTTPLLLLDLALLVDADEGTCG |
| 193 | GGEQNP1YWAQDYAWLFTTPLLLLDLALLVDADEGTCG |
| 194 | GGEQNPIYWAQYDAWLFTTPLLLLDLALLVDADEGTCG |
| 195 | GGEQNPIYWAQDYAWLFTTPLLLLDLALLVDADEGTCG |
| 196 | GGEQNPIYWAQYADWLFTTPLLLLDLALLVDADEGTCG |
| 197 | AAEQNPIYWARYAAWLFTTPLLLLDLALLVDADEGTCG |
| 198 | GGEQNPIYWAQDYAWLFTTPLLLLDLALLVDADEGTCG |
| 199 | GGEQNPIYWAQYDAWLFTTPLLLLDLALLVDADEGTCG |
| 200 | GGEQNPIYWAQYADWLFTTPLLLLDLALLVDADEGTCG |
| 201 | AAEQNPIYWARYAAWLFTTPLLLLDLALLVDADEGTCG |
| 202 | AAEQNPIYWARYADWLFTTPLLLLELALLVDADEGTKCG |
| 203 | . . . EGTK(rhidamine)C(phalloidin)G |
| 204 | AAEQNPIYWARYADWLFTTPLLLLDLALLVDADEGTKCG |
| 205 | ACEQNPIYWARYADWLFTTPLLLLDLALLVDADEGTG |
| 206 | AAEQNPIYWARYADWLFTTPLLLLDLALLVDADEGTC(phalloidin)G |
| 207 | AAEQNPIYWARYADWLFTTPLLLLDLALLVDADEGTKCG |
| 208 | AAEQNPIYWARYADWLFTTPLLLLELALLVDADEGTKCG |
| 209 | AAEQNPIYWARYADWLFTDLPLLLLDLLALLVDADEGT |
| 210 | AAEQNPIYWARYAAWLFTTPLLLLLDLALLVDADEGTCG |

TABLE 1-continued

Additional R¹ Sequences

| SEQ ID NO. | Sequence |
|---|---|
| 211 | GGEQNPIYWAQYDAWLFTTPLLLLDLALLVDADEGTCG |
| 212 | GGEQNPIYWAQDYAWLFTTPLLLLDLALLVDADEGTCG |
| 213 | GGEQNPIYWARYDAWLFTTPLLLLDLALLVDADEGTCG |
| 214 | AAEQNPIYWARYAEWLFTTPLLLLDLALLVDADEGTCG |
| 215 | AAEQNPIYWARYAEWLFTTPLLLLELALLVDADEGTCG |
| 216 | AAEQNPIYWARYADWLFTTPLLLLALALLVDADEGTCG |
| 217 | AAEQNPIYWARYADWLFTTPLLLLELALLVDADEGTCG |
| 218 | AAEQNPIYWARYAEWLFTTPLLLLELALLVDADEGTCG |
| 219 | AAEQNPIYWARYADWLFTTPLLLLELALLVDADEGTKCG |
| 220 | ACEQNPIYWARYAKWLFTTPLLLLKLALLVDADEGTG |
| 221 | ACEQNPIYWARYANWLFTTPLLLLNLALLVDADEGTG |
| 222 | AAEQNPIYWARYADWLFTTALLLLDLALLVDADEGT |
| 223 | AEQNPIYFARYADLLFPTTLAW |
| 224 | AEQNPIYWARYADLLFPTTLAF |
| 225 | AEQNPIYWARYADLLFPTTLAW |
| 226 | ACEQNPIYWARYADWLFTTPLLLLDLALLVDADET |
| 227 | GGEQNPIYWARYADWLFTTPLLLLDLALLVDADEGT |
| 228 | AAEQNPIYWARYADWLFTTPLLLLDLALLVDADEGTCG |
| 229 | AAEQNPIYWARYADWLFTTPLLLLDLALLVDADEGTKCG |
| 230 | AKEQNPIYWARYADWLFTTPLLLLDLALLVDADECT |
| 231 | CCTCTTACCTCAGTTACA |
| 232 | D-Arg8 D-Arg8-CCTCTTACCTCAGTTACA |
| 233 | D-Lys4 D-Lys4-CCTCTTACCTCAGTTACA |
| 234 | S-S-CCTCTTACCTCAGTTACA |
| 235 | S-S-CCTCTGACCTCATTTACA |
| 236 | D-Arg8-Deca D-Arg8-Deca-CCTCTTACCTCAGTTACA |
| 237 | D-Arg8-Deca-mismatch D-Arg8-Deca-CCTCTGACCTCATTTACA |
| 238 | S-S-CCTCTTACCTCAGTTACA |
| 239 | AAEQNPIYWARYADWLFTTPLLLLLDLALLVDADEGTCG |
| 240 | AEDQNPYWARYDWLFTTPLLLLDLALLVDCG |
| 241 | AEDQNPYWARYADWLFTTPLLLLELALLVECG |
| 242 | AEQNPIYWARYADWLFTTPLLLLDLALLVDADEGCT |
| 243 | ACEQNPIYWARYADWLFTTPLLLLLDLALLVDADET |
| 244 | AE-QN-PIYWARYADWLFTTPLLLLDLALLVDADEGT-COOH |
| 245 | AEDQN-P-YWARYADWLFTTPLLLLDLALLVD---G--COOH |
| 246 | AEDQNDP-YWARYADWLFTTPLLLLDLALLV----G--COOH |
| 247 | AEQNPIYWARYADFLFTTPLLLLDLALLV DADET-COOH |
| 248 | AEQNPI YFARYADWLFTTPLLLLDLALLV DADET-COOH |
| 249 | AEQNPI YFARYADFLFTTPLLLLDLALLW DADET-COOH |
| 250 | AE-QN-PI YWARYADWLFTTPLLLLDLALLV DADEGCT-COOH |
| 251 | AEDQN-PI YWARYADWLFTTPLLLLDLALLV DC--G-T-COOH |
| 252 | AEDQNDPI YWARYADWLFTTPLLLLELALLV EC--G-T-COOH |
| 253 | Chelate-ACEEQNPWARYLEWLFPTETLLLEL |
| 254 | AEQNPIY WARYADWLFTTPLLLLDLALLV DADEGT-COOH |
| 255 | AKEDQNPY WARYADWLFTTPLLLLDLALLV DG-COOH |
| 256 | AKEDQNDPY WARYADWLFTTPLLLLDLALLV G-COO H |
| 257 | AEQNPI YWARYADWLFTTPLLLLDLALLV DADEGC-Biotin-T-COO H |
| 258 | AEDQNP YWARYADWLFTTPLLLLDLALLV DC-Biotin-G-COOH |
| 259 | AEDQNP YWARYADWLFTTPLLLLELALLV EC-Biotin-G-COOH |
| 260 | ACEQNPIY WARYADWLFTTPLLLLDLALLV DADEGT |
| 261 | ACEDQNPY WARYADWLFTTPLLLLDLALLV DG |
| 262 | ACEDQNPY WRAYADLFTPLTLLDLLALW DG |
| 263 | ACDDQNP WRAYLDLLFPTDTLLLDLLW |
| 264 | WRAYLELLFPTETLLLELLW |
| 265 | WARYLDWLFPTDTLLLDL |
| 266 | WRAYLDLLFPTDTLLLDW |
| 267 | WARYLEWLFPTETLLLEL |
| 268 | WAQYLELLFPTETLLLEW |
| 269 | WRAYLELLFPTETLLLEW |
| 270 | WARYADWLFPTTLLLLD |
| 271 | WARYAEWLFPTTLLLLE |
| 272 | ACEDQNP WARYADLLFPTTLAW |
| 273 | ACEEQNP WARYAELLFPTTLAW |
| 274 | Ac-TEDADVLLALDLLLLPTTFLWDAYRAWYPNQECA-Am |
| 275 | CDDDDDNPNY WARYANWLFTTPLLLLNGALLV EAEET |
| 276 | CDDDDDNPNY WARYAPWLFTTPLLLLPGALLV EAEET |
| 277 | Ac-AEQNPIYWARYADWLFTTPLLLLLDLALLVDADEGCT |

TABLE 1-continued

Additional R¹ Sequences

| SEQ ID NO. | Sequence |
|---|---|
| 278 | Ac-AKEQNPIYWARYADWLFTTPLLLLDLALLVDADEGTG |
| 279 | ACEQNPIYWARYANWLFTTPLLLLNLALLVDADEGT |
| 280 | Ac-AAEQNPIYWARYADWLFTTPLLLLELALLVDADEGTKCG |
| 281 | DDDEDNPIYWARYADWLFTTPLLLLHGALLVDADET |
| 282 | CDDDEDNPIYWARYAHWLFTTPLLLLHGALLVDADET |
| 283 | DDDEDNPIYWARYAHWLFTTPLLLLHGALLVDADEGT |
| 284 | DDDEDNPIYWARYAHWLFTTPLLLLHGALLVNADECT |
| 285 | DDDEDNPIYWARYAHWLFTTPLLLLHGALLVNANEGT |
| 286 | AKEDQNDPYWARYADWLFTTPLLLLDLALLVG |
| 287 | AEDQNPYWARYADWLFTTPLLLLELALLVCG |
| 288 | AKDDQNPWRAYLDLLFPTDTLLLDLLWC |
| 289 | ACEEQNPWRAYLELLFPTETLLLELLW |
| 290 | ACDDQNPWARYLDWLFPTDTLLLDL |
| 291 | CDNNNPWRAYLDLLFPTDTLLLDW |
| 292 | CEEQQPWAQYLELLFPTETLLLEW |
| 293 | EEQQPWRAYLELLFPTETLLLEW |
| 294 | CDDDDDNPNYWARYANWLFTTPLLLLNGALLVEAEET |
| 295 | CDDDDDNPNYWARYAPWLFTTPLLLLPGALLVEAEE |
| 296 | AEQNPIYFARYADLLFPTTLAW |
| 297 | AEQNPIYWARYADLLFPTTLAF |
| 298 | AEQNPIYWARYADLLFPTTLAW |
| 299 | KEDQNPWARYADLLFPTTLW |
| 300 | ACEEQNPQAEYAEWLFPTTLLLLE |
| 301 | AAEEQNPWARYLEWLFPTETLLLEL |
| 302 | AKEEQNPWARYLEWLFPTETLLLEL |
| 303 | AAEQNPIYWARYADWLFTTPLLLLDLALLVDADEGTGG |
| 304 | XXEXNPIYWAXXXXXLFTXXLLLXXXALLVXAXXXTXG |
| 305 | DAAEQNPIYWARYADWLFTTLPLLLLDLLALLVDADEGTKGG |
| 306 | GGEQNPIYWARYADWLFTTPLLLLDLALLVDADEGTGG |
| 307 | XXEXNPIYWAXXXXXLFTXXLLLXXXALLVXAXXXTGG |
| 308 | DGGEQNDPIYWARYADWLFTTLPLLLLDLLALLVDADEGCTXGG |
| 309 | AAEQNPIYWARYADWLFTTPLLLLDLALLVDADEGTCG |
| 310 | AEDQNPYWARYDWLFTTPLLLLDLALLVDCG |
| 311 | GLAGLAGLLGLEGLLGLPLGLLEGLWLGLELEGN |

Any of the recited peptides useful in the present invention can be modified to include a cysteine residue by replacing a non-cysteine residue with cysteine, or appending a cysteine residue to either the N-terminus or C-terminus.

In some embodiments, the peptide of $R^1$ is a conformationally restricted peptide. A conformationally restricted peptide can include, for example, macrocyclic peptides and stapled peptides. A stapled peptide is a peptide constrained by a covalent linkage between two amino acid side-chains, forming a peptide macrocycle. Conformationally restricted peptides are described, for example, in Guerlavais et al., Annual Reports in Medicinal Chemistry 2014, 49, 331-345; Chang et al., Proceedings of the National Academy of Sciences of the United States of America (2013), 110(36), E3445-E3454; Tesauro et al., Molecules 2019, 24, 351-377; Dougherty et al., Journal of Medicinal Chemistry (2019), 62(22), 10098-10107; and Dougherty et al., Chemical Reviews (2019), 119(17), 10241-10287, each of which is incorporated herein by reference in its entirety.

In some embodiments, $R^1$ is a peptide having 10 to 50 amino acids. In some embodiments, $R^1$ is a peptide having 20 to 40 amino acids. In some embodiments, $R^1$ is a peptide having 20 to 40 amino acids. In some embodiments, $R^1$ is a peptide having 10 to 20 amino acids. In some embodiments, $R^1$ is a peptide having 20 to 30 amino acids. In some embodiments, $R^1$ is a peptide having 30 to 40 amino acids.

Suitable small molecule microtubule targeting moieties (e.g., $R^2$) can be cytotoxic compounds like maytansinoids that may have undesirable side effects when delivered systemically because of their possible deleterious effect on normal tissue. Small molecule microtubule targeting agents include, but are not limited to, maytansinoids, aclitaxel, docetaxel, epothilones, discodermolide, the vinca alkaloids, colchicine, combretastatins, and derivatives and analogues of the aforementioned. Microtubule targeting agents are described in Tangutur, A. D., Current Topics in Medicinal Chemistry, 2017 17(22): 2523-2537. Microtubule-targeting agents also include maytansinoids, such as maytansine (DM1) and derivatives and analogues thereof, which are described in Lopus, M, Cancer Lett., 2011, 307(2): 113-118; and Widdison, W., J. Med. Chem. 2006, 49:4392-4408.

In some embodiments, $R^2$ is the following group:

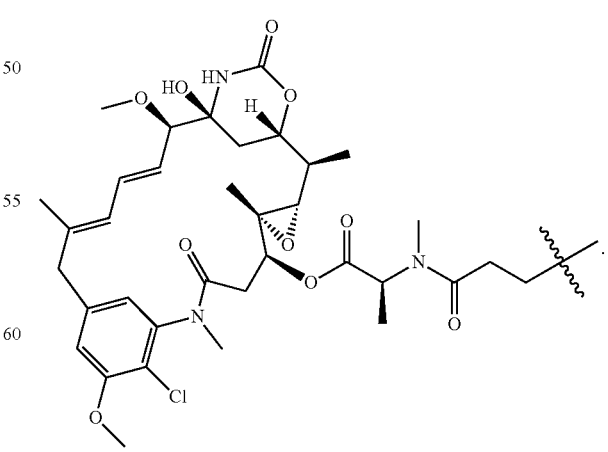

In some embodiments, R² is the following group:
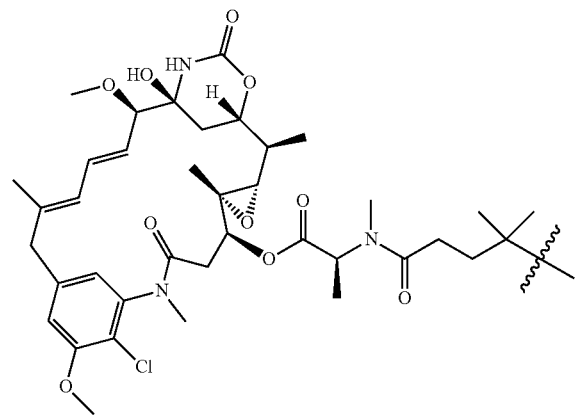
In some embodiments, R² is the following group:
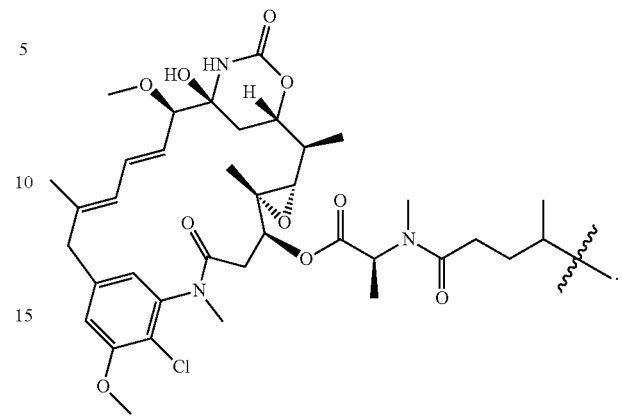
In some embodiments, R² is the following group:
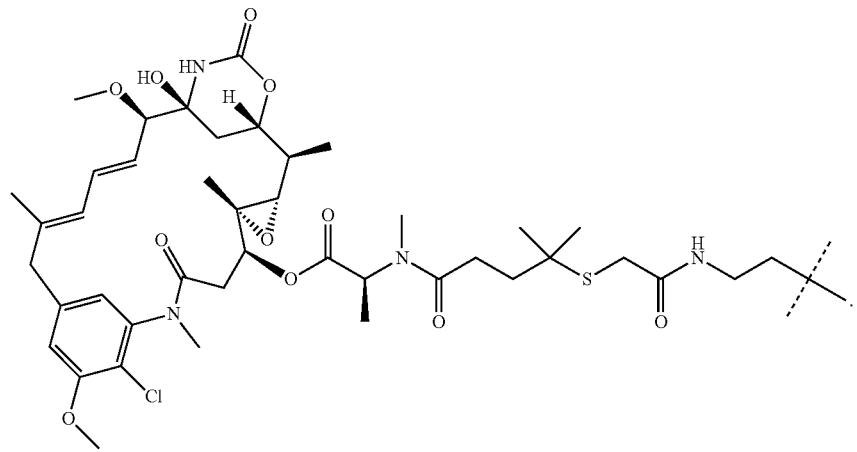
In some embodiments, R² is the following group:
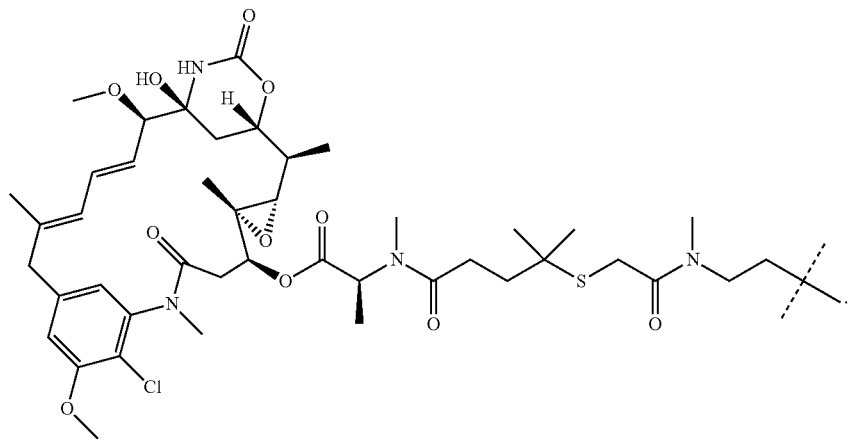

In some embodiments, $R^2$ is a maytansinoid. In some embodiments, $R^2$ is DM1 or DM4. In some embodiments, $R^2$ is DM1. In some embodiments, $R^2$ is DM4.

In some embodiments, L is a linking moiety that covalently connects $R^1$ and $R^2$, and functions to release a moiety containing $R^2$ in the vicinity of acidic or hypoxic tissue, such as inside a cell of diseased tissue.

In some embodiments, L is a linking chain of 1 to 40, 1 to 30, 1 to 25, 1 to 20, 1 to 15, 1 to 10, or 1 to 5 chain atoms (including both carbon and heteroatoms), which is optionally substituted with 1-10 $R^q$ substituents, and wherein one or more chain carbon atoms of L can be oxidized to form a carbonyl (C=O), and wherein one or more N and S chain atoms can each be optionally oxidized to form an amine oxide, sulfoxide or sulfonyl group; wherein each $R^q$ is independently selected from OH, CN, —COOH, $NH_2$, halo, $C_{1-6}$ haloalkyl, $C_{1-6}$ alkyl, $C_{1-6}$ alkoxy, $C_{1-6}$ haloalkoxy, $C_{1-6}$ alkylthio, phenyl, 5-6 membered heteroaryl, 4-6 membered heterocycloalkyl, $C_{3-6}$ cycloalkyl, $NH(C_{1-6}$ alkyl) and $N(C_{1-6}$ alkyl)$_2$, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5- or 6-membered heteroaryl or 4-6 membered heterocycloalkyl; and two $R^q$ groups together with the chain atoms to which they are attached can form a phenyl, 5-6 membered heteroaryl, 4-6 membered heterocycloalkyl, or $C_{3-6}$ cycloalkyl ring.

In some embodiments, $R^q$ is independently selected from OH, CN, —COOH, $NH_2$, halo, $C_{1-6}$ haloalkyl, $C_{1-6}$ alkyl, $C_{1-6}$ alkoxy, $C_{1-6}$ haloalkoxy, $NH(C_{1-6}$ alkyl) and $N(C_{1-6}$ alkyl)$_2$.

In some embodiments, L is the following group:

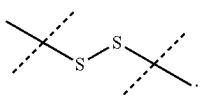

In some embodiments, L is the following group:

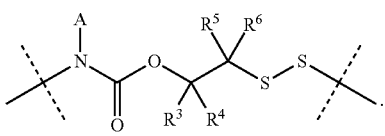

In some embodiments, L is the following group:

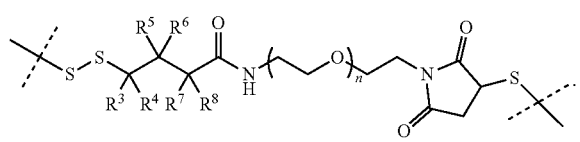

In some embodiments, n is 0. In some embodiments, n is 1. In some embodiments, n is 2.

In some embodiments, L is the following group:

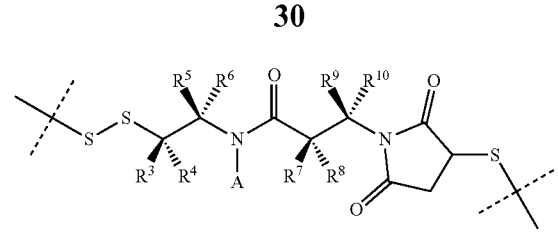

In some embodiments, L is the following group:

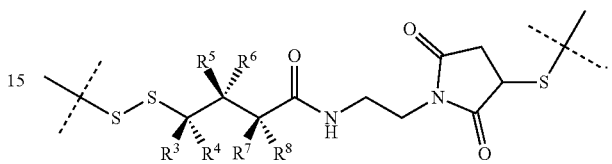

In some embodiments, L is the following group:

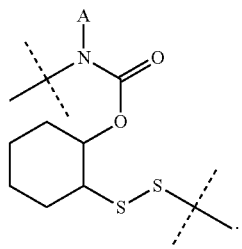

In some embodiments, L is the following group:

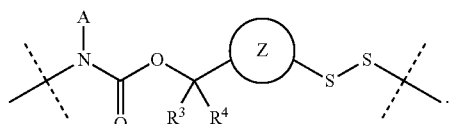

In some embodiments, $R^3$, $R^4$, $R^5$, $R^6$, $R^7$, $R^8$, $R^9$, and $R^{10}$ are each independently selected from H and $C_{1-4}$ alkyl. In some embodiments, $R^3$, $R^4$, $R^5$, $R^6$, $R^7$, $R^8$, $R^9$, and $R^{10}$ are each H.

In some embodiments, $R^3$ and $R^4$ are each independently selected from H and $C_{1-4}$ alkyl. In some embodiments, $R^3$ and $R^4$ are each H.

In some embodiments, $R^5$ and $R^6$ are each independently selected from H and $C_{1-4}$ alkyl. In some embodiments, $R^5$ and $R^6$ are each H.

In some embodiments, $R^7$ and $R^8$ are each independently selected from H and $C_{1-4}$ alkyl. In some embodiments, $R^7$ and $R^8$ are each H.

In some embodiments, $R^9$ and $R^{10}$ are each independently selected from H and $C_{1-4}$ alkyl. In some embodiments, $R^9$ and $R^{10}$ are each H.

In some embodiments, A is H. In some embodiments, A is $C_{1-4}$ alkyl. In some embodiments, A is $CH_3$.

In some embodiments, Z is $C_{6-10}$ aryl, optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$.

In some embodiments, Z is phenyl, optionally substituted with 1, 2, or 3 substituents independently selected from $C_{1-4}$ alkyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$.

In some embodiments, Z is phenyl.

In some embodiments, the compound of the invention is a compound of Formula (II):

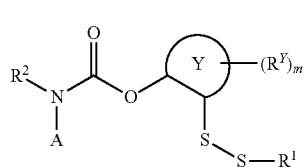

(II)

or a pharmaceutically acceptable salt thereof, wherein.

R$^1$ is a peptide;
R$^2$ is a small molecule microtubule targeting moiety;
A is H or C$_{1-4}$ alkyl;
Ring Y is a monocyclic C$_{5-7}$ cycloalkyl ring or a monocyclic 5-7 membered heterocycloalkyl ring;
each R$^Y$ is independently selected from C$_{1-4}$ alkyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;
or two adjacent R$^Y$ together with the atoms to which they are attached form a fused monocyclic C$_{5-7}$ cycloalkyl ring, a fused monocyclic 5-7 membered heterocycloalkyl ring, a fused C$_{6-10}$ aryl ring, or a fused 6-10 membered heteroaryl ring, each of which is optionally substituted with 1, 2, or 3 substituents independently selected from C$_{1-4}$ alkyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;
R$^{a1}$, R$^{b1}$, R$^{c1}$, and R$^{d1}$ are each independently selected from H, C$_{1-4}$ alkyl, C$_{2-4}$ alkenyl, C$_{2-4}$ alkynyl, each optionally substituted with 1, 2, or 3 substituents independently selected from halo, OH, CN, and NO$_2$; and
m is 0, 1, 2, or 3.

In some embodiments of compounds of Formula (II), R$^1$ is a peptide comprising the sequence of SEQ ID NO: 1, SEQ ID NO:2, SEQ ID NO:3, SEQ ID NO:4, or SEQ ID NO:5.

In some embodiments of compounds of Formula (II), R$^1$ is Pv1, Pv2, Pv3, Pv4, or Pv5.

In some embodiments of compounds of Formula (II), R$^1$ is attached to the core via a cysteine residue of R$^1$ wherein one of the sulfur atoms of the disulfide moiety in Formula II is derived from the cysteine residue.

In some embodiments of compounds of Formula (II), R$^2$ is a maytansinoid. In some embodiments of Formula (II), R$^2$ is DM1 or DM4. In some embodiments of Formula (II), R$^2$ is DM1. In some embodiments of Formula (II), R$^2$ is DM4.

In some embodiments of compounds of Formula (II), R$^2$ is the following group:

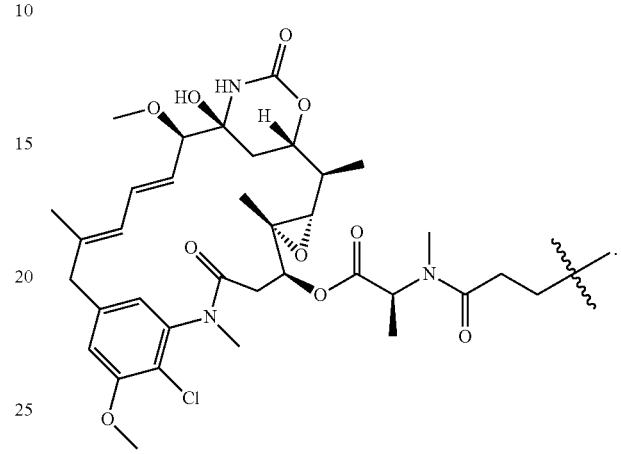

In some embodiments of compounds of Formula (II), R$^2$ is the following group:

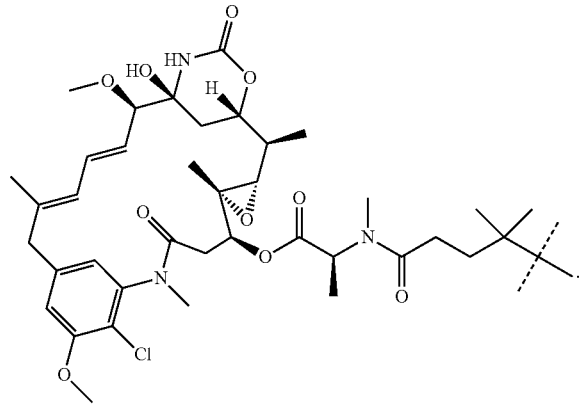

In some embodiments of compounds of Formula (II), R$^2$ is the following group:

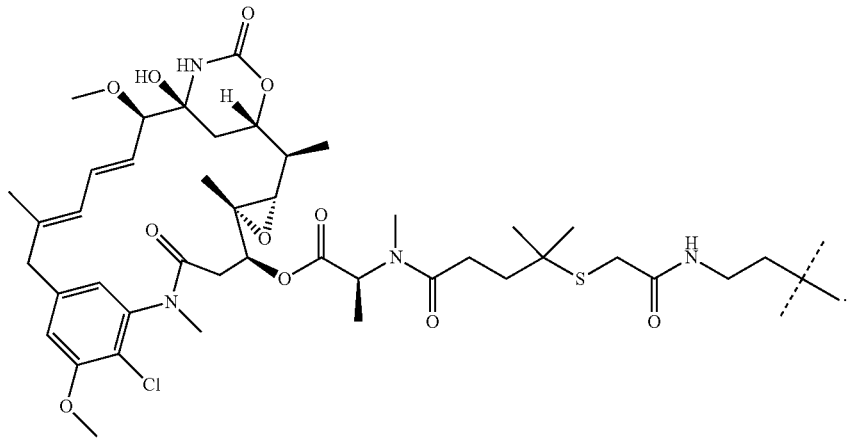

In some embodiments of compounds of Formula (II), $R^2$ is the following group:

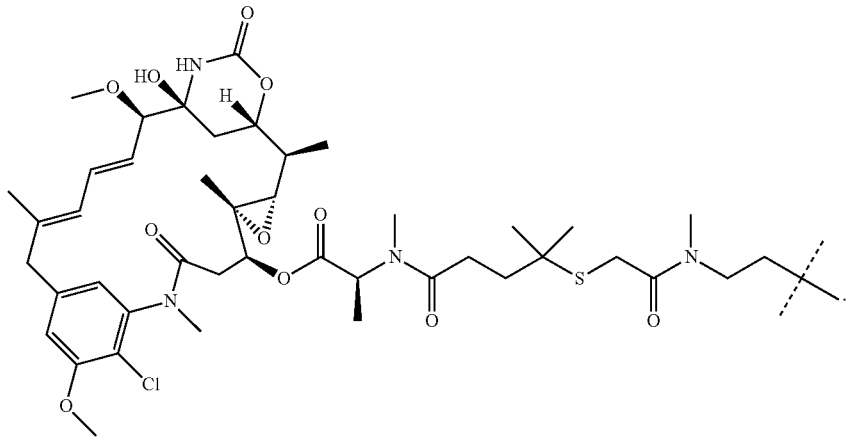

In some embodiments of compounds of Formula (II), A is H. In some embodiments of compounds of Formula (II), A is $C_{1-4}$ alkyl. In some embodiments of compounds of Formula (II), A is $CH_3$.

In some embodiments of compounds of Formula (II), Ring Y is a monocyclic $C_{5-7}$ cycloalkyl ring.

In some embodiments of compounds of Formula (II), Ring Y is a cyclopentyl ring.

In some embodiments of compounds of Formula (II), Ring Y is a cyclohexyl ring.

In some embodiments of compounds of Formula (II), Ring Y is a cycloheptyl ring.

In some embodiments of compounds of Formula (II), Ring Y is a monocyclic 5-7 membered heterocycloalkyl ring.

In some embodiments of compounds of Formula (II), Ring Y is a 5-membered heterocycloalkyl ring.

In some embodiments of compounds of Formula (II), Ring Y is a 6-membered heterocycloalkyl ring.

In some embodiments of compounds of Formula (II), Ring Y is a 7-membered heterocycloalkyl ring.

In some embodiments of compounds of Formula (II), two adjacent $R^Y$ together with the atoms to which they are attached form a fused monocyclic $C_{5-7}$ cycloalkyl ring, a fused monocyclic 5-7 membered heterocycloalkyl ring, a fused $C_{6-10}$ aryl ring, or a fused 6-10 membered heteroaryl ring, each of which is optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$.

In some embodiments of compounds of Formula (II), m is 0.

In some embodiments of compounds of Formula (II), m is 1.

In some embodiments of compounds of Formula (II), m is 2.

In some embodiments of compounds of Formula (II), m is 3.

In some embodiments, the compounds of the invention is a compound of Formula (III), Formula (IV), or Formula (V):

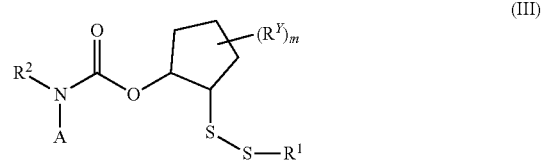

(III)

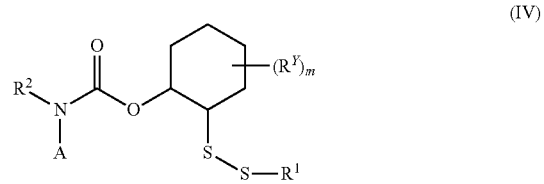

(IV)

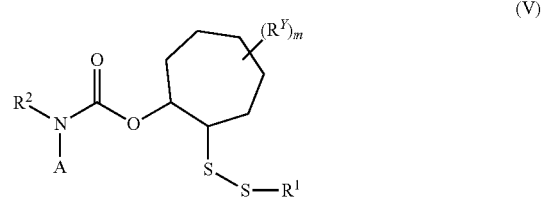

(V)

or a pharmaceutically acceptable salt thereof, wherein $R^1$, $R^2$, $R^Y$, A, and m are defined as in any of the embodiments above for Formula (II).

In some embodiments, the compound of formula (I) is selected from:

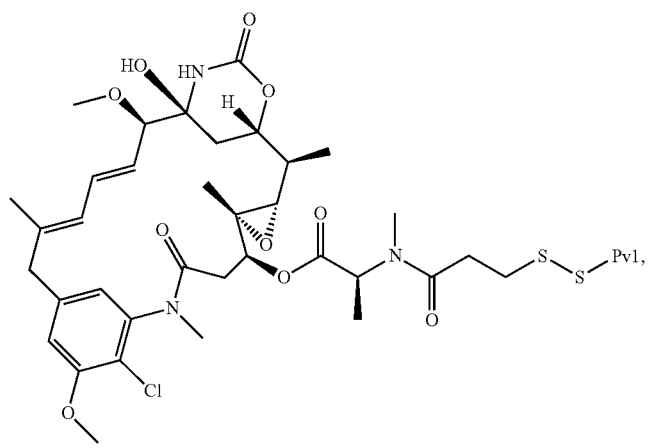
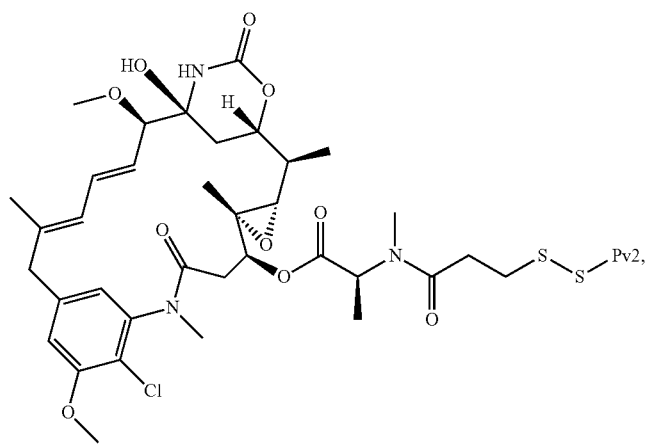
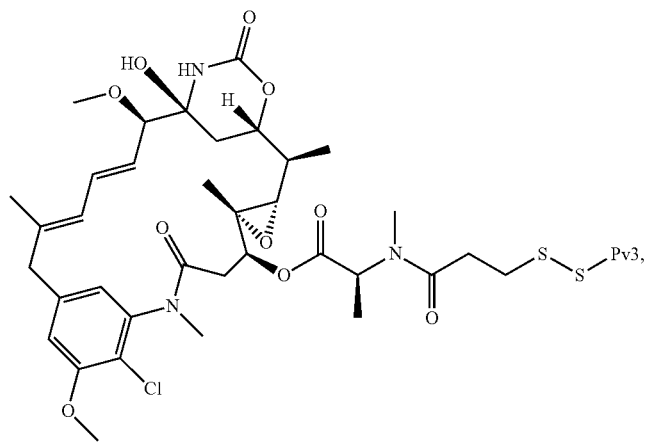

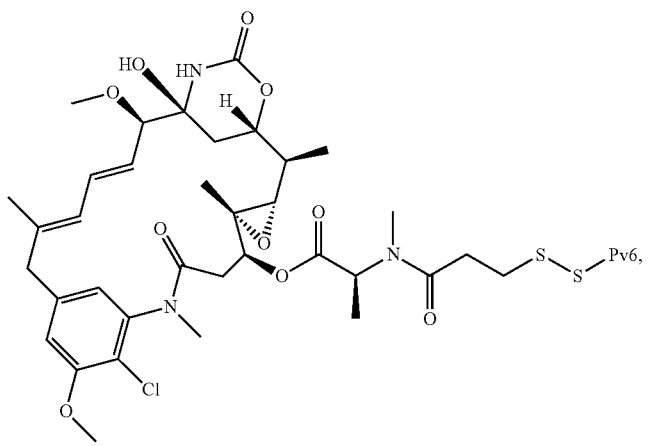
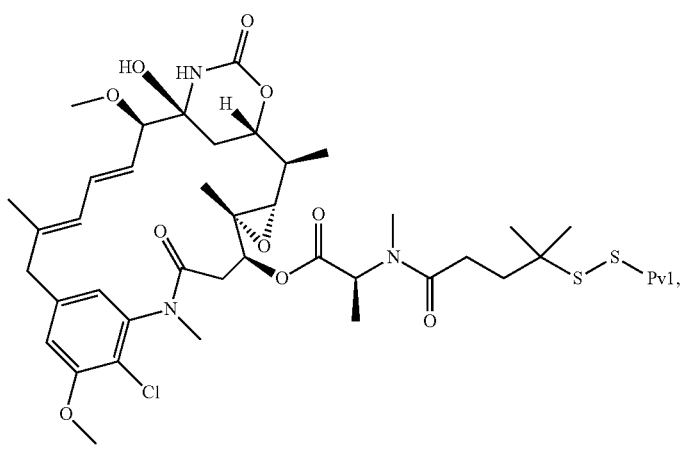
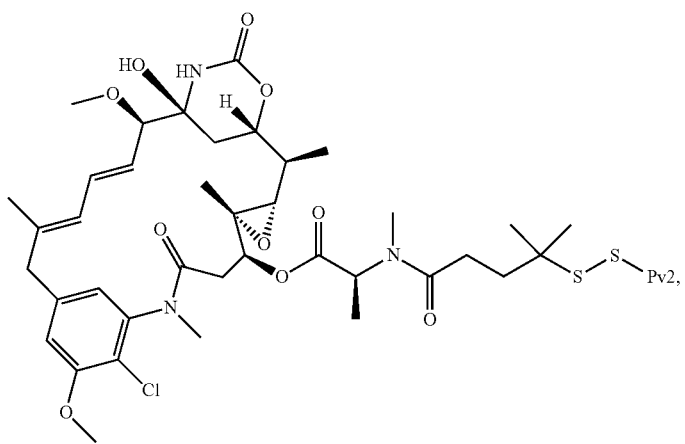

-continued
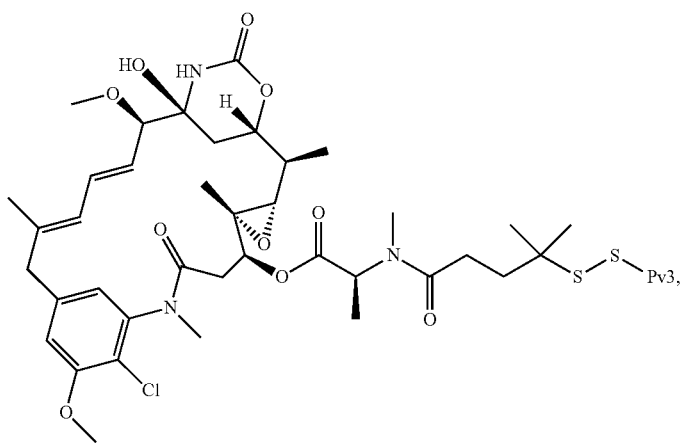
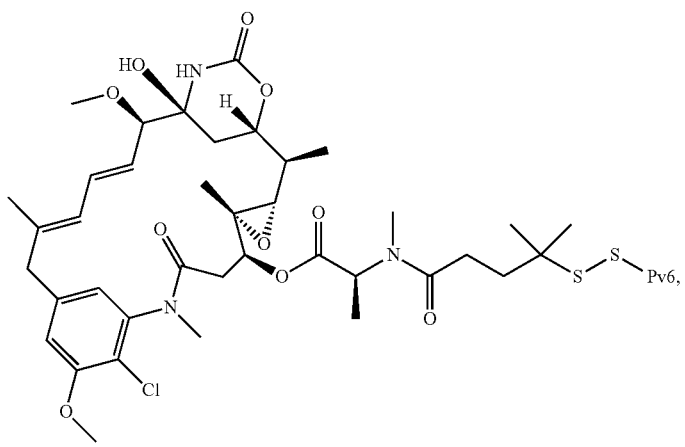
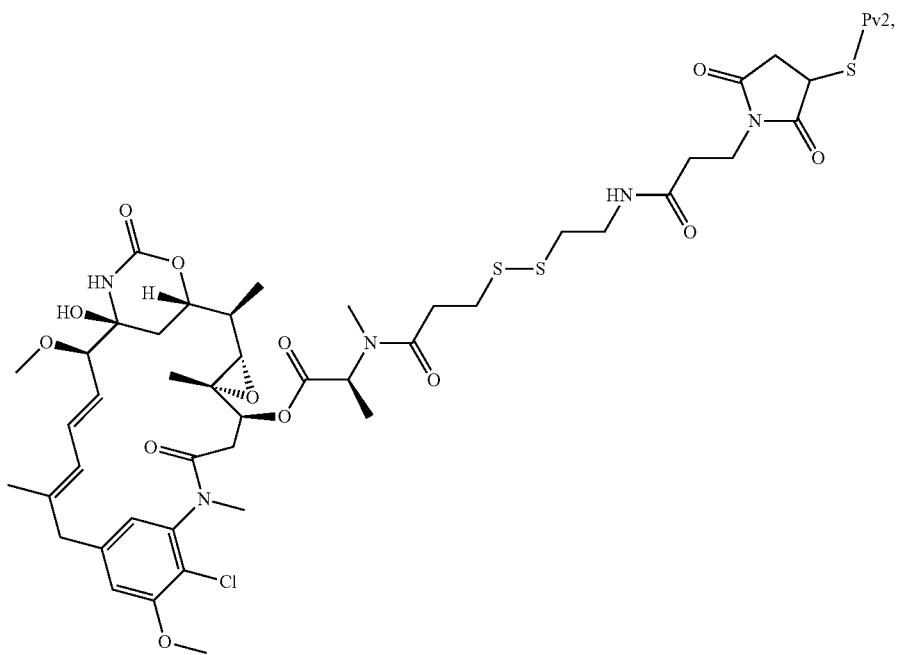

or a pharmaceutically acceptable salt of any of the aforementioned.
In some embodiments, the compound of Formula (I) is selected from:
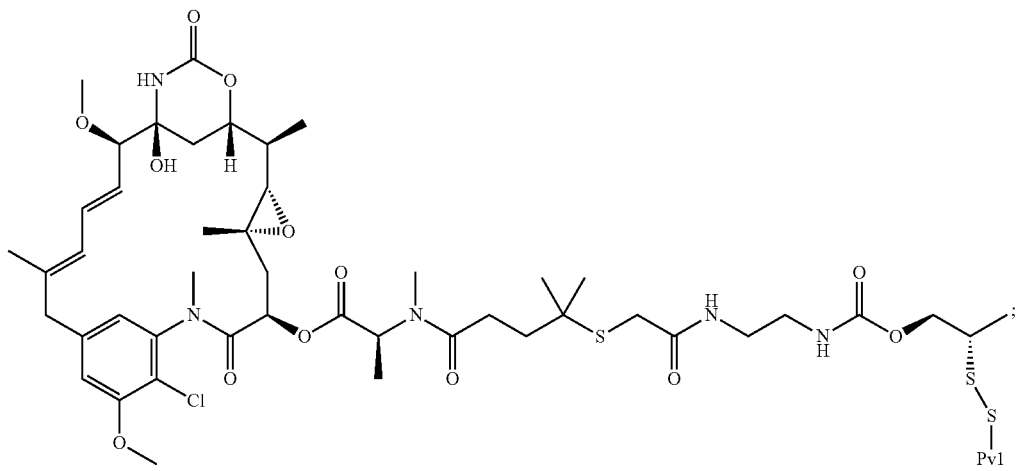
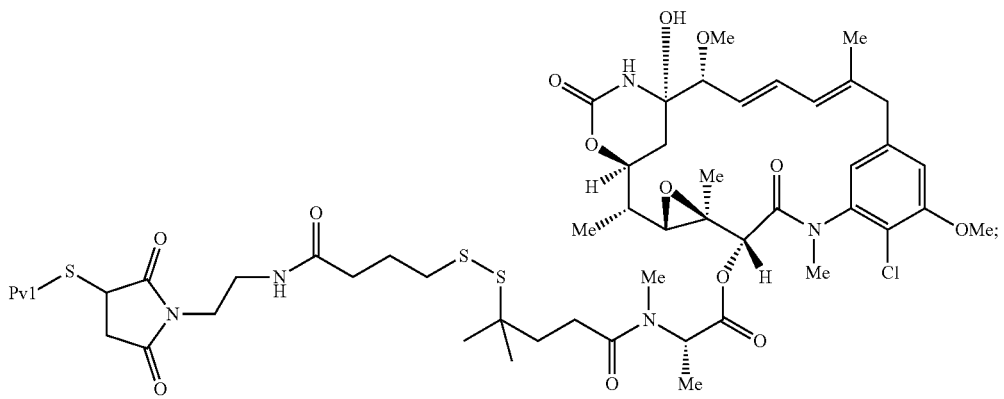
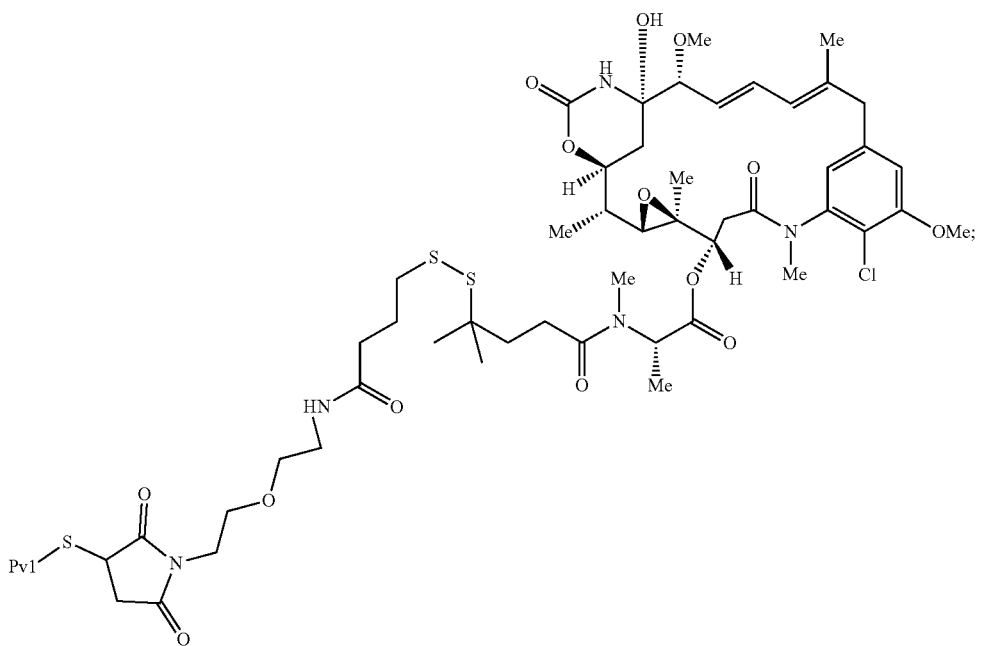

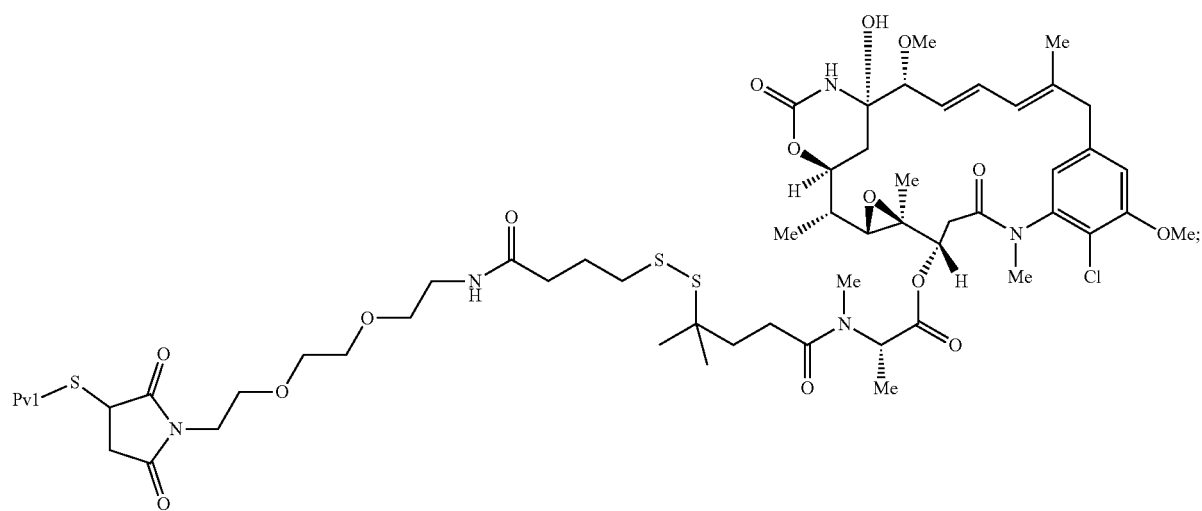
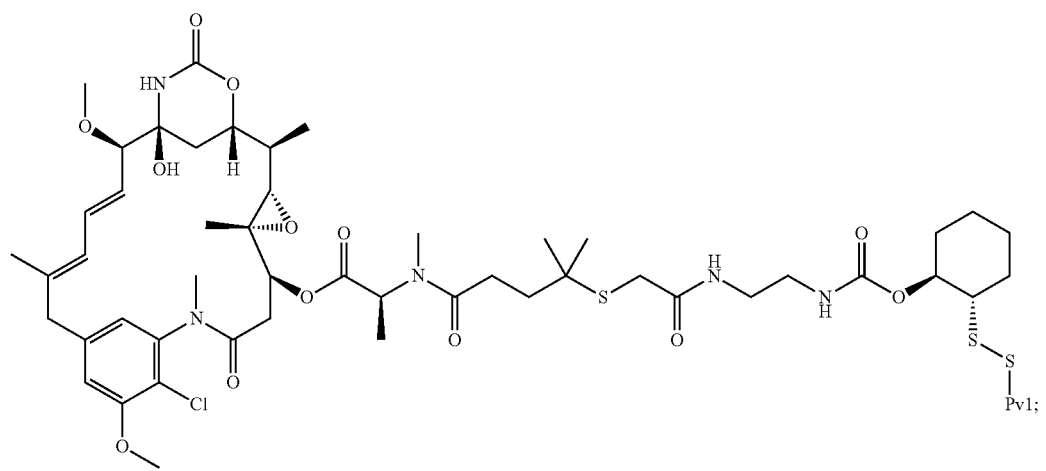
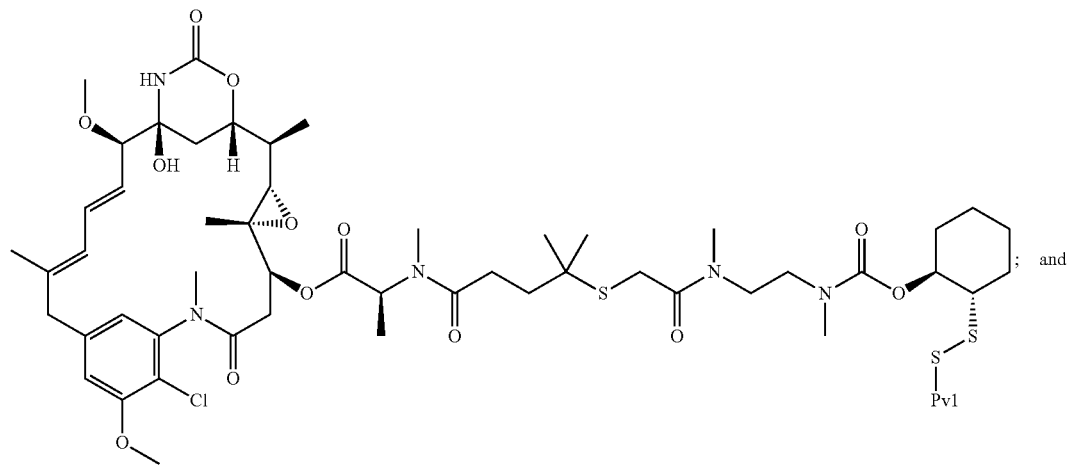

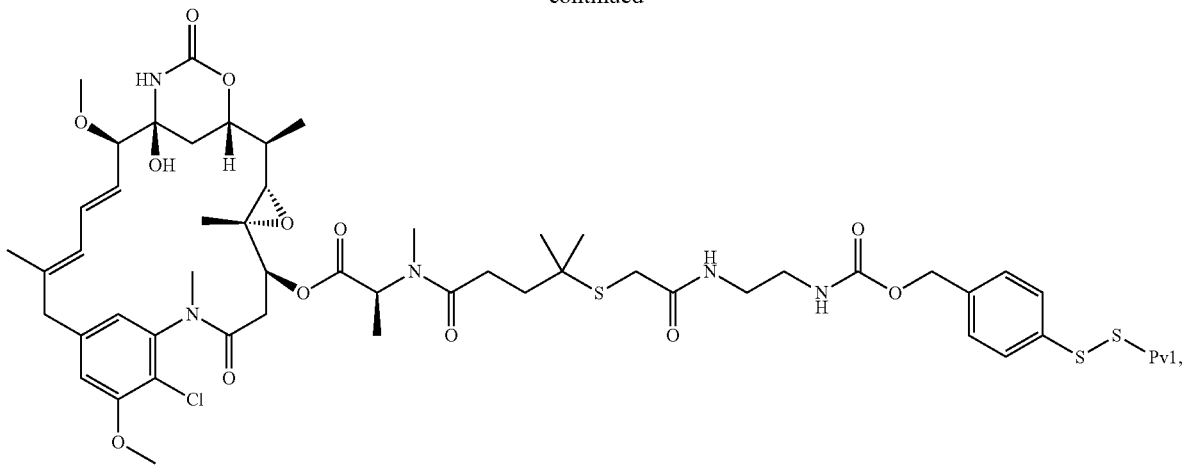

or a pharmaceutically acceptable salt of any of the aforementioned.

In some embodiments, provided herein is a compound having Formula (I-A):

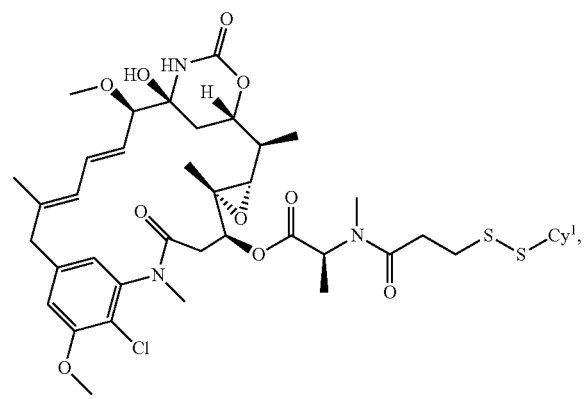

(I-A)

or a salt thereof, wherein $Cy^1$ is $C_{6-10}$ aryl or 5-10 membered heteroaryl. In some embodiments, $Cy^1$ is pyridyl.

In some embodiments, provided herein is a compound having Formula (I-B):

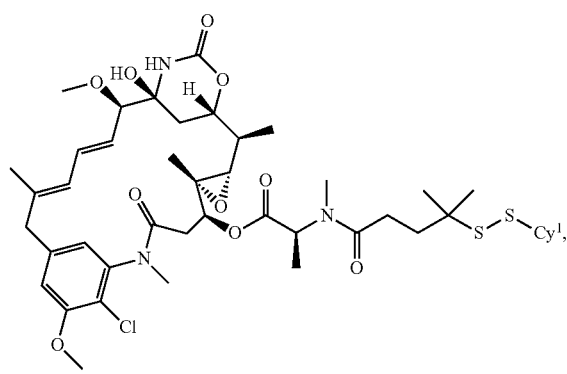

or a salt thereof, wherein $Cy^1$ is $C_{6-10}$ aryl or 5-10 membered heteroaryl. In some embodiments, $Cy^1$ is pyridyl.

The molecules of the invention can be tagged, for example, with a probe such as a fluorophore, radioisotope, and the like. In some embodiments, the probe is a fluorescent probe, such as LICOR. A fluorescent probe can include any moiety that can re-emit light upon light excitation (e.g., a fluorophore).

The Amino acids are represented by the IUPAC abbreviations, as follows: Alanine (Ala; A), Arginine (Arg; R), Asparagine (Asn; N), Aspartic acid (Asp; D), Cysteine (Cys; C), Glutamine (Gln; Q), Glutamic acid (Glu; E), Glycine (Gly; G), Histidine (His; H), Isoleucine (Ile; I), Leucine (Leu; L), Lysine (Lys; K), Methionine (Met; M), Phenylalanine (Phe; F), Proline (Pro; P), Serine (Ser; S), Threonine (Thr; T), Tryptophan (Trp; W), Tyrosine (Tyr; Y), Valine (Val; V).

The term "Pv1" means ADDQNPWRAYLDLL-FPTDTLLLDLLWCG, which is the the peptide of SEQ ID No. 1.

The term "Pv2" means AEQNPIYWARY-ADWLFTTPLLLLDLALLVDADECG, which is the peptide of SEQ ID No. 2.

The term "Pv3" means ADDQNPWRAYLDLL-FPTDTLLLDLLWDADECG, which is the peptide of SEQ ID No. 3.

The term "Pv4" means Ac-AAEQNPIYWARY-ADWLFTTPLLLLDLALLVDADEGTKCG, which is the peptide of SEQ ID NO. 4.

The term "Pv5" means AAEQNPIYWARY-ADWLFTTPLLLLDLALLVDADEGTC, which is the peptide of SEQ ID NO. 5. The term "Pv6" means AAEQN-PIYWWARYADWLFTTPLLLLDLALLVDADEGTCG, which is the peptide of SEQ ID NO. 6. In the compounds of the invention, the peptides $R^1$ are attached to the disulfide linker by a cysteine moiety.

The term "acidic and/or hypoxic mantle" refers to the environment of the cell in the diseased tissue in question having a pH lower than 7.0 and preferably lower than 6.5. An acidic or hypoxic mantle more preferably has a pH of about 5.5 and most preferably has a pH of about 5.0. The compounds of formula (I) insert across a cell membrane having an acidic and/or hypoxic mantle in a pH dependent fashion to insert $R^2L$ into the cell, whereupon the disulfide bond of the linker is cleaved to deliver free $R^2L$ (or $R^2L^*$, wherein L* is a product of degradation). Since the compounds of formula (I) are pH-dependent, they preferentially insert across a cell membrane only in the presence of an acidic or hypoxic mantle surrounding the cell and not across the cell membrane of "normal" cells, which do not have an acidic or hypoxic mantle.

The terms "pH-sensitive" or "pH-dependent" as used herein to refer to the peptide $R^1$ or to the mode of insertion of the peptide $R^1$ or of the compounds of the invention across a cell membrane, means that the peptide has a higher affinity to a cell membrane lipid bilayer having an acidic or hypoxic mantle than a membrane lipid bilayer at neutral pH. Thus, the compounds of the invention preferentially insert through the cell membrane to insert $R^2L$ to the interior of the cell (and thus deliver $R^2H$ as described above) when the cell membrane lipid bilayer has an acidic or hypoxic mantle (a "diseased" cell) but does not insert through a cell membrane when the mantle (the environment of the cell membrane lipid bilayer) is not acidic or hypoxic (a "normal" cell). It is believed that this preferential insertion is achieved as a result of the peptide $R^1$ forming a helical configuration, which facilitates membrane insertion.

The term "small molecule microtubule targeting moiety" refers to a chemical group that binds to microtubules. The small molecule microtubule targeting moiety can be a group derived from a compound that inhibits the activity of microtubules. For example, the small molecule microtubule targeting moiety may suppress the dynamic stability of microtubules. In some embodiments, the small molecule microtubule targeting moiety has a molecular weight (Da) of about 100-1500, about 100-800, about 500-1,000, about 600-1,000, about 100-500, about 700-900, or about 250-500.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR (CR'R")$_n$— and —(CR'R")$_n$NR— and is intended to disclose each of the forms individually.

Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound.

The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1, 4-diyl, butan-1,3-diyl, butan-1,2-diyl, 2-methyl-propan-1,3-diyl and the like.

The term "amino" refers to a group of formula —$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized ☐ (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring.

A five-membered heteroaryl ring is a heteroaryl group having five ring atoms wherein one or more (e.g., 1, 2 or 3) ring atoms are independently selected from N, O and S.

A six-membered heteroaryl ring is a heteroaryl group having six ring atoms wherein one or more (e.g., 1, 2 or 3) ring atoms are independently selected from N, O and S.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_3$-7). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2-pyrrolidinyl, morpholinyl, azetidinyl, tetrahydrofuranyl, tetrahydropyranyl, and piperazinyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as α-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in Remington's Pharmaceutical Sciences, 17th Ed., (Mack Publishing Company, Easton, 1985), p. 1418, Berge et al., J. Pharm. Sci., 1977, 66(1), 1-19 and in Stahl et al., Handbook of Pharmaceutical Salts: Properties, Selection, and Use, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., March's Advanced Organic Chemistry: Reactions, Mechanisms, and Structure, 6th Ed. (Wiley, 2007); Peturssion et al., "Protecting Groups in Carbohydrate Chemistry," J. Chem. Educ., 1997, 74(11), 1297; and Wuts et al., Protective Groups in Organic Synthesis, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below.

Scheme 1 Synthesis of Direct Conjugates

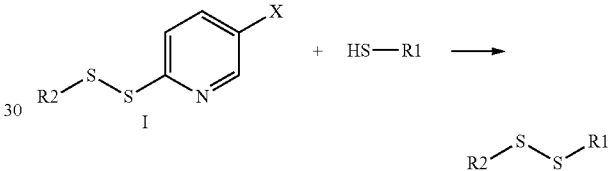

A small molecule microtubule targeting moiety which contains an inherent thiol ($R^2$—SH), such as DM1 or DM4, can be activated by the formation of pyridyl disulfide (wherein X is, for example, H, halo, etc.), which can be displaced with a thiol containing $R^1$ peptide in a disulfide exchange reaction to give the desired conjugate where —S—S— is the linking moiety L.

Scheme 2 Synthesis of Direct Conjugates

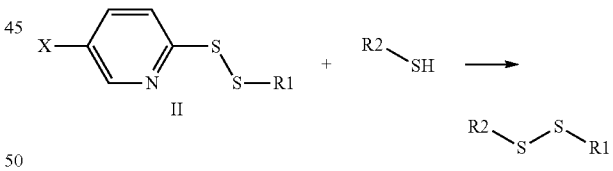

Alternatively, the $R^1$ peptide, which has an inherent thiol, can be activated by the formation of pyridyl disulfide (II) which can be displaced with a thiol-containing $R^2$ in a disulfide exchange reaction to give the desired direct conjugate where L is —S—S—.

Scheme 3 Synthesis of Thioethyl Amine Amide Conjugates

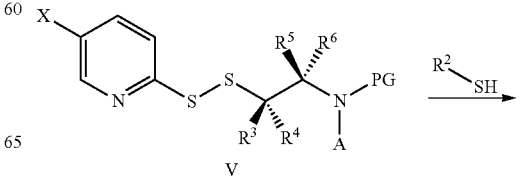

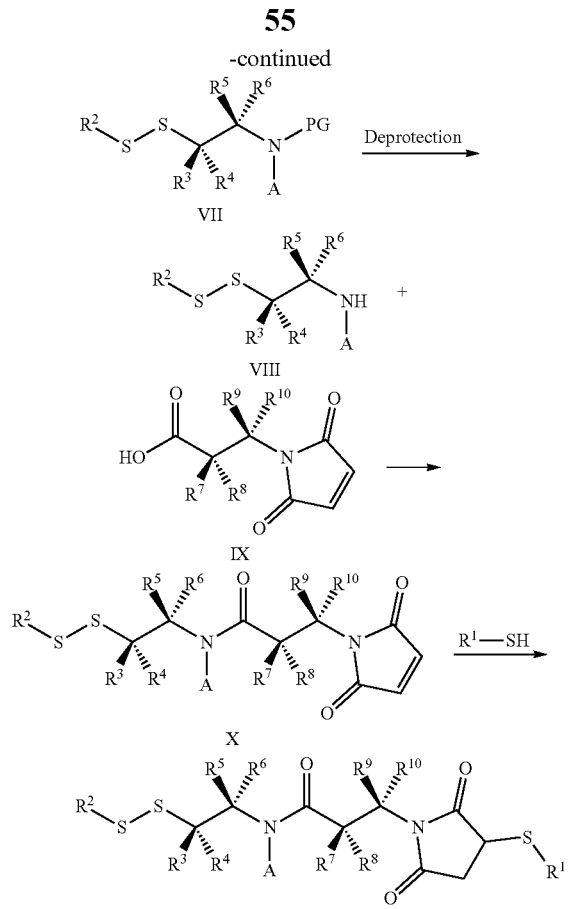

A protected ethyl amine, containing a thiol group that has been activated as pyridyl disulfide V can be reacted with thiol-containing $R^2$ in a disulfide exchange reaction to give VII. Disulfide VII can be deprotected to give VIII and further reacted with a propionic maleimide IX in an acid coupling reaction to provide amide X. Amide X can be reacted with a thiol containing peptide in a Michael addition to give the desired conjugate.

Scheme 4 Synthesis of Thiobutyric Amide Conjugates

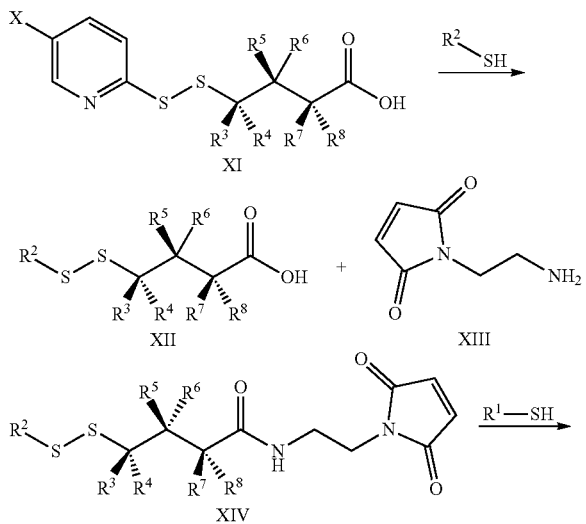

A thiol-containing butyric acid that has been activated as a pyridyl disulfide XI can be reacted with thiol containing $R^2$ in a disulfide exchange reaction to give XII. Disulfide acid XII can be reacted with ethylaminomaleimide XIII in an acid coupling reaction to provide amide XIV. Amide XIV can be reacted with a thiol-containing peptide in a Michael addition to give the desired conjugate.

The peptides $R^1$ may be prepared using the solid-phase synthetic method first described by Merrifield in J.A.C.S., Vol. 85, pgs. 2149-2154 (1963), although other art-known methods may also be employed. The Merrifield technique is well understood and is a common method for preparation of peptides. Useful techniques for solid-phase peptide synthesis are described in several books such as the text "Principles of Peptide Synthesis" by Bodanszky, Springer Verlag 1984. This method of synthesis involves the stepwise addition of protected amino acids to a growing peptide chain which was bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond, followed by the addition of the succeeding protected amino acids, one at a time, in a stepwise manner until the desired sequence is assembled. Finally, the protected peptide is removed from the solid resin support and the protecting groups are cleaved off.

The amino acids may be attached to any suitable polymer. The polymer must be insoluble in the solvents used, must have a stable physical form permitting ready filtration, and must contain a functional group to which the first protected amino acid can be firmly linked by a covalent bond. Various polymers are suitable for this purpose, such as cellulose, polyvinyl alcohol, polymethylmethacrylate, and polystyrene.

Methods of Use

Provided herein is the use of the compounds of formula (I) in the treatment of diseases, such as cancer or neurodegenerative disease. Another aspect of the present invention is the use of the compounds of formula (I) in the treatment of diseases involving acidic or hypoxic diseased tissue, such as cancer. Hypoxia and acidosis are physiological markers of many disease processes, including cancer. In cancer, hypoxia is one mechanism responsible for development of an acid environment within solid tumors. As a result, hydrogen ions must be removed from the cell (e.g., by a proton pump) to maintain a normal pH within the cell. As a consequence of this export of hydrogen ions, cancer cells have an increased pH gradient across the cell membrane lipid bilayer and a lower pH in the extracellular milieu when compared to normal cells. One approach to improving the efficacy and therapeutic index of cytotoxic agents is to leverage this physiological characteristic to afford selective delivery of compound to hypoxic cells over healthy tissue.

In these methods of treatment, a therapeutically-effective amount of a compound of formula (I) or a pharmaceutically-acceptable salt thereof may be administered as a single agent or in combination with other forms of therapy, such as ionizing radiation or cytotoxic agents in the case of cancer. In combination therapy, the compound of formula (I) may be administered before, at the same time as, or after the other therapeutic modality, as will be appreciated by those of skill in the art. Either method of treatment (single agent or combination with other forms of therapy) may be administered as a course of treatment involving multiple doses or treatments over a period of time.

Examples of cancers that are treatable using the compounds of the present disclosure include, but are not limited to, colorectal cancer, gastric cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers treatable with compounds of the present disclosure include bladder cancer, bone cancer, glioma, breast cancer (e.g., triple-negative breast cancer), cervical cancer, colon cancer, colorectal cancer, endometrial cancer, epithelial cancer, esophageal cancer, Ewing's sarcoma, pancreatic cancer, gallbladder cancer, gastric cancer, gastrointestinal tumors, head and neck cancer (upper aerodigestive cancer), intestinal cancers, Kaposi's sarcoma, kidney cancer, laryngeal cancer, liver cancer (e.g., hepatocellular carcinoma), lung cancer (e.g., non-small cell lung cancer, adenocarcinoma), melanoma, prostate cancer, rectal cancer, renal clear cell carcinoma, skin cancer, stomach cancer, testicular cancer, thyroid cancer, and uterine cancer.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, a compound of formula (I) or a pharmaceutically-acceptable salt thereof may be used in combination with a chemotherapeutic agent, a targeted cancer therapy, an immunotherapy or radiation therapy. The agents can be combined with the present compounds in a single dosage form, or the agents can be administered simultaneously or sequentially as separate dosage forms. In some embodiments, the chemotherapeutic agent, targeted cancer therapy, immunotherapy or radiation therapy is less toxic to the patient, such as by showing reduced bone marrow toxicity, when administered together with a compound of formula (I), or a pharmaceutically acceptable salt thereof, as compared with when administered in combination with the corresponding microtubule targeting agent (e.g., $R^2$—H).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents that can be administered in combination with the compounds of the invention include, for example, navelbene, CPT-11, anastrazole, letrazole, capecitabine, reloxafine, cyclophosphamide, ifosamide, and droloxafine.

Also suitable are cytotoxic agents such as, for example, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-α, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines that can be administered in combination with the compounds of the invention include, for example, dendritic cells, synthetic peptides, DNA vaccines and recombinant viruses.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or administered in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with the compounds of the invention. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with compounds of the invention. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds of the invention. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds of the present invention. A further example of a PARP inhibitor that can be combined with a compound of the invention is talazoparib.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

The phrase "therapeutically effective amount" of a compound (therapeutic agent, active ingredient, drug, etc.) refers to an amount of the compound to be administered to a subject in need of therapy or treatment which alleviates a symptom, ameliorates a condition, or slows the onset of disease conditions, according to clinically acceptable standards for the disorder or condition to be treated. For instance, a therapeutically effective amount can be an amount which has been demonstrated to have a desired therapeutic effect in an in vitro assay, an in vivo animal assay, or a clinical trial. The therapeutically effective amount can vary based on the particular dosage form, method of administration, treatment protocol, specific disease or condition to be treated, the benefit/risk ratio, etc., among numerous other factors.

Said therapeutically effective amount can be obtained from a clinical trial, an animal model, or an in vitro cell culture assay. It is known in the art that the effective amount suitable for human use can be calculated from the effective amount determined from an animal model or an in vitro cell culture assay. For instance, as reported by Reagan-Shaw et al., FASEB J. 2008: 22(3) 659-61, "µg/ml" (effective amount based on in vitro cell culture assays)="mg/kg body weight/day" (effective amount for a mouse). Furthermore, the effective amount for a human can be calculated from the effective amount for a mouse based on the fact that the metabolism rate of mice is 6 times faster than that of humans.

As an example of treatment using a compound of formula (I) in combination with a cytotoxic agent, a therapeutically-effective amount of a compound of formula (I) may be administered to a patient suffering from cancer as part of a treatment regimen also involving a therapeutically-effective amount of ionizing radiation or a cytotoxic agent. In the context of this treatment regimen, the term "therapeutically-effective" amount should be understood to mean effective in the combination therapy. It will be understood by those of skill in the cancer-treatment field how to adjust the dosages to achieve the optimum therapeutic outcome.

Similarly, the appropriate dosages of the compounds of the invention for treatment of non-cancerous diseases or conditions (such as cardiovascular diseases) may readily be determined by those of skill in the medical arts.

The term "treating" as used herein includes the administration of a compound or composition which reduces the frequency of, delays the onset of, or reduces the progression of symptoms of a disease involving acidic or hypoxic diseased tissue, such as cancer, stroke, myocardial infarction, or long-term neurodegenerative disease, in a subject relative to a subject not receiving the compound or composition. This can include reversing, reducing, or arresting the symptoms, clinical signs, or underlying pathology of a condition in a manner to improve or stabilize a subject's condition (e.g., regression of tumor growth, for cancer or decreasing or ameliorating myocardial ischemia reperfusion injury in myocardial infarction, stroke, or the like cardiovascular disease). The terms "inhibiting" or "reducing" are used for cancer in reference to methods to inhibit or to reduce tumor growth (e.g., decrease the size of a tumor) in a population as compared to an untreated control population.

All publications (including patents) mentioned herein are incorporated herein by reference for the purpose of describing and disclosing, for example, the constructs and methodologies that are described in the publications, which might be used in connection with the disclosure herein described. The publications discussed throughout the text are provided solely for their disclosure prior to the filing date of the present application.

Disclosed herein are several types of ranges. When a range of any type is disclosed or claimed, the intent is to disclose or claim individually each possible number that such a range could reasonably encompass, including end points of the range as well as any sub-ranges and combinations of sub-ranges encompassed therein. When a range of therapeutically effective amounts of an active ingredient is disclosed or claimed, for instance, the intent is to disclose or claim individually every possible number that such a range could encompass, consistent with the disclosure herein. For example, by a disclosure that the therapeutically effective amount of a compound can be in a range from about 1 mg/kg to about 50 mg/kg (of body weight of the subject).

Formulation, Dosage Forms and Administration

To prepare the pharmaceutical compositions of the present invention, a compound of Formula (I) or a pharmaceutically-acceptable salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. One of skill in the pharmaceutical and medical arts will be able to readily determine a suitable dosage of the pharmaceutical compositions of the invention for the particular disease or condition to be treated.

EXAMPLES

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

Brine: a saturated NaCl solution in water
DCM: dichloromethane
TFA: trifluoroacetic acid
DIPEA: diisopropylethylamine
DMA: dimethylacetamide
DME: dimethoxyethane
DMF: dimethylformamide
DMSO: methylsulfoxide
DTT: dithiothreitol
MSD: mass spec detector
$Et_2O$: ethyl ether
EtOAc: ethyl acetate
EtOH: ethyl alcohol
HATU: O-(7-azabenzotriazol-1-yl)-N,N,N',N'-tetramethyluronium hexafluorophosphate
HOBt: 1-hydroxybenzotriazole
RP: reverse phase
HPLC: high performance liquid chromatography
IPA: isopropanol
LAH: lithium aluminum hydride
N-BuLi: n-butyl lithium
LC-MS: liquid chromatography-mass spectrometry
LDA: lithium diisoproylethylamide
Me: methyl
MeOH: methanol
MTBE: methyl t-butyl ether
NMP: N-methylpyrrolidine
Ph: phenyl
PNPC: para-nitrophenylchloroformate
RT or rt: room temperature
SFC: supercritical fluid chromatography
TBAI: tetrabutylammonium iodide
TBME: tert-butylmethyl ether
tBu: tertiary butyl
THF: tetrahydrofuran
TEA: triethylamine
TMEDA: tetramethylethylenediamine
GSH: Glutathione
GS: Glutathione bonded at sulfur
LiOH: lithium hydroxide
DPPA: diphenyl phosphoryl azide
$Sn(Bu)_2(Laurate)_2$: dibutyltin dilaurate
PBS: phosphate buffered saline
ACN: acetonitrile
AcOH: acetic acid
EEDQ: N-ethoxycarbonyl-2-ethoxy-1,2-dihydroquinoline DMAP: 4-dimethylaminopyridine
EDC: 1-ethyl-3-(3-dimethylaminopropyl)carbodiimide
The HPLC methods employed are set forth below.

HPLC Methods

A: Sunfire C18 150×4.6 mm; H₂O/Acetonitrile w/TFA modifier (0.05%); Flow rate: 1 ml/min; Wavelength=217 nM.

B: Ace Equivalence 250×4.6 mm; H₂O/Acetonitrile w/TFA modifier (0.05%); Flow rate: 1 ml/min; Wavelength=217 nM.

C: Sunfire C18 150×30 mm; H₂O/Acetonitrile w/TFA modifier (0.05%); Flow rate: 30 ml/min; Wavelength=217 nM.

D: Sunfire C18 150×4.6 mm; H₂O/Acetonitrile w/AcOH modifier (0.5%); Flow rate: 1 ml/min; Wavelength=217 nM E: Sunfire C18 150×30 mm; H₂O/Acetonitrile w/AcOH modifier (0.5%); Flow rate: 30 ml/min; Wavelength=217 nM.

F: Agilent 1100/1200/1260 or 1290 systems (coupled or uncoupled with MS).

| HPLC Parameters | |
| --- | --- |
| Mobile Phase A | 0.1% AcOH in water |
| Mobile Phase B | 0.1% AcOH in ACN |
| Column | Merck Chromolith RP-18e |
| Column Temperature | rt |
| Autosampler Temperature | rt |
| Injection Volume | 5 μL |
| Flow Rate | 1 mL/minute |
| Wavelength | Agilent diode array detector at λ = 254, 220 or 280 nm |

| Gradient Program | Time (min) | % A | % B |
| --- | --- | --- | --- |
| | Initial | 95.00 | 5.00 |
| | 4.00 | 5.00 | 95.00 |
| | 4.99 | 5.00 | 95.00 |
| | 5.00 | 95.00 | 5.00 |
| | 6.00 | 95.00 | 5.00 |
| Run Time | 6.00 | | |

G: Agilent 1100/1200/1260 or 1290 systems (coupled or uncoupled with MS).

| HPLC Parameters | |
| --- | --- |
| Mobile Phase A | 0.1% TFA in water |
| Mobile Phase B | 0.1% TFA in ACN |
| Column | Agilent Eclipse XDB C8 column (3.5 μm, 4.6 × 150 mm) |
| Column Temperature | 40° C. |
| Autosampler Temperature | rt |
| Injection Volume | 5 μL |
| Flow Rate | 1.5 mL/minute |
| Wavelength | Agilent diode array detector at λ = 254, 220 or 280 nm |

| Gradient Program | Time (min) | % A | % B |
| --- | --- | --- | --- |
| | Initial | 80.00 | 20.00 |
| | 0.20 | 80.00 | 20.00 |
| | 7.50 | 20.00 | 80.00 |
| | 8.00 | 0.00 | 100.00 |
| | 9.00 | 0.00 | 100.00 |
| | 10.00 | 80.00 | 20.00 |
| Run Time | 10.00 | | |

Mass Spectrometry Methods

Maldi-TOF (Matrix-assisted laser desorption/ionization-Time of Flight) mass spectrometry was measured on an Applied Biosystems Voyager System 6268. The sample was prepared as a matrix of α-cyano hydroxy cinnamic acid on an AB Science plate (Part #V700666).

ESI (Electrospray Ionization) mass spectrometry was measured on either an Agilent 1100 series LC-MS with a 1946 MSD or a Waters Xevo Qtof high-resolution MS, both providing a mass/charge species (m/z=3).

The source of the starting materials employed in the Examples are set forth below in the following tables.

TABLE 2

Starting materials for $R^2$

| $R^2$ Code | $R^2$H Structure | Synthesis, Reference or Purchased |
| --- | --- | --- |
| $R^2$SH-1 | | MedKoo 123212 |

TABLE 2-continued

Starting materials for $R^2$

| $R^2$ Code | $R^2H$ Structure | Synthesis, Reference or Purchased |
|---|---|---|
| $R^2SH$-2 | | MedKoo 206839 |
| $R^2SH$-3 | | US 20040235840 A1 |

Synthesis of Intermediate I ($R^2S$—S-Pyr)

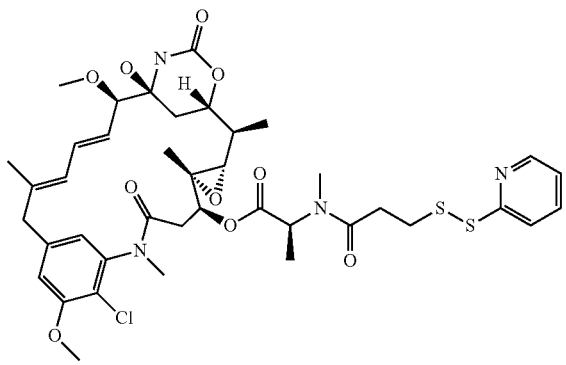

To [(1S,2R,3 S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[methyl(3-sulfanylpropanoyl)amino]propanoate (46.7 mg, 0.06 mmol) in 1 mL of CH₃CN was added 2-(2-pyridyldisulfanyl)pyridine (20.0 mg, 0.09 mmol). The mixture was concentrated and purified (SiO₂, 0-10% MeOH/CH₂Cl₂) to give [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[methyl-[3-(2-pyridyldisulfanyl)propanoyl]amino]propanoate (53.6 mg, yield: 100%). MS m/z 847.1 [M+H]⁺.

Synthesis of Pv3-S-Pyr (Intermediate II-3)

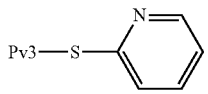

Pv3 (250 mg, 0.06 mmol; as a free flowing solid) and 2-(2-pyridyldisulfanyl)pyridine (0.110 g, 0.5 mol) were dissolved in MeOH (10 mL) and the reaction stirred overnight at room temperature. LC-MS indicates the desired product was formed. The reaction mixture was concentrated and the residue taken up in DMSO and purified by reverse phase column chromatography (40-65% CH₃CN/H₂O (0.5%

AcOH), 13 min) to give 212 mg of the desired product (187 mg, yield: 74.9%). MS m/z=3 1273.4.

Intermediates II-1, II-2 and II-6 were prepared analogously to II-3, using Pv1, Pv2, and Pv6, as shown below:

| Intermediate | Structure | MS<br>A: Maldi-TOF<br>B: m/z = 3 |
|---|---|---|
| II-1 | Pv1-SPyr | B: 1130.1 |
| II-2 | Pv2-SPyr | B: 1373.9 |
| II-3 | Pv3-SPyr | B: 1273.4 |
| II-6 | Pv6-SPyr | B: 1450.3 |

TABLE 3

Starting materials for L groups

| Intermediate | Structure | Purchased, Reference or Synthesized |
|---|---|---|
| III-1 | HS~~NH₂ | Enamine EN3000-33931 |
| III-2 | HS-C(CH₃)₂-CH₂-NH₂·HCl | Astatech 39541 |
| III-3 | HS-CH(CH₃)-CH₂-NH₂ (S) | Enamine EN3000-6731388 |
| III-4 | HS-CH(CH₃)-CH₂-NH₂ (R) | Enamine EN3000-6731596 |
| III-5 | HS-(4-piperidinyl) | Astatech 39018 |

Synthesis of Intermediate VI-2

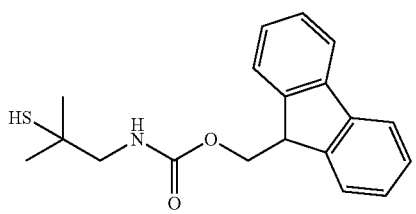 [SMILES: CC(C)(S)CNC(=O)OCC1c2ccccc2-c2ccccc21]

1-Amino-2-methyl-propane-2-thiol hydrochloride (100 mg, 0.706 mmol) was dissolved in $CH_2Cl_2$ (7 mL) and to it was added 9H-fluoren-9-ylmethyl carbonochloridate (274 mg, 1.06 mmol) and N,N-diisopropylethylamine (182 mg, 1.41 mmol). The reaction mixture was stirred at room temperature overnight. The reaction mixture was washed with water and concentrated. The residue was purified by column chromatography (0-50% EtOAc/hexanes) to give 9H-fluoren-9-ylmethyl N-(2-methyl-2-sulfanyl-propyl)carbamate (213 mg, yield: 92.2%). MS m/z 350.1 [M+Na]⁺.

Synthesis of Intermediate V-1

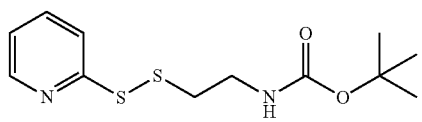 [SMILES: CC(C)(C)OC(=O)NCCSSc1ccccn1]

2-(2-Pyridyldisulfanyl)pyridine (746 mg, 3.38 mmol) was dissolved in MeOH (15 mL) and to it was added tert-butyl N-(2-sulfanylethyl)carbamate (200 mg, 1.13 mmol). The reaction was stirred for 3 h at room temperature. The mixture was concentrated and the residue purified by column chromatography (0-50% EtOAc/hexanes) to give tert-butyl N-[2-(2-pyridyldisulfanyl)ethyl]carbamate (200 mg, yield: 61.9%). MS m/z 287.1 [M+H]⁺.

Synthesis of Intermediate V-2

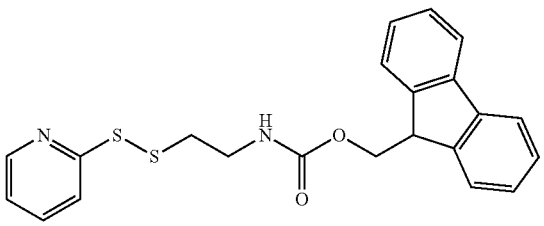 [SMILES: O=C(NCCSSc1ccccn1)OCC1c2ccccc2-c2ccccc21]

2-(2-Pyridyldisulfanyl)ethanamine hydrochloride (200 mg, 0.898 mmol) was dissolved in $CH_2Cl_2$ and to it was added 9H-fluoren-9-ylmethyl carbonochloridate (348 mg, 1.35 mmol) and N,N-diisopropylethylamine (232 mg, 1.80 mmol). The reaction mixture was stirred at RT for 2 h, washed with water and concentrated. The residue was purified by column chromatography (0-50% EtOAc/hexanes) to give 9H-fluoren-9-ylmethyl N-[2-(2-pyridyldisulfanyl)ethyl]carbamate (288 mg, yield: 78.5%). MS m/z 409.1 [M+H]⁺.

Synthesis of Intermediate VII-1

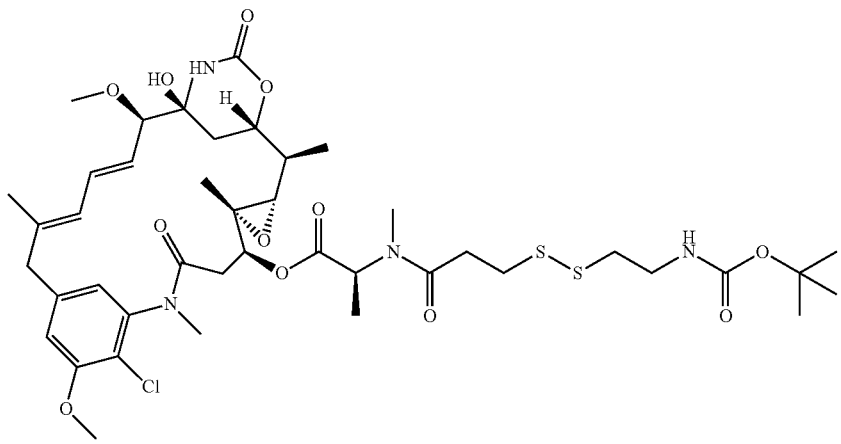

To a vial containing [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[methyl(3-sulfanylpropanoyl)amino]propanoate (25.0 mg, 0.03 mmol) in 1 mL of $CH_3CN$ was added tert-butyl N-[2-(2-pyridyldisulfanyl)ethyl]carbamate (Intermediate V-1, 14.5 mg, 0.051 mmol) and 4-methylmorpholine (0.138 mL, 1.25 mmol). The mixture was stirred for 16 h. LC-MS analysis indicates the desired material. The mixture was concentrated, dissolved in 50 mL of EtOAc and washed with 1×25 mL of sat. $NH_4Cl$ and 1×25 mL of sat. brine. The organic phase was dried with $MgSO_4$, filtered and concentrated. The crude residue was purified ($SiO_2$, 0-100% EtOAc/hexanes) to give [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-[2-(tert-butoxycarbonylamino)ethyldisulfanyl]propanoyl-methyl-amino]propanoate (30.9 mg, yield: 100%). MS m/z 913.2 $[M+H]^+$.

Synthesis of Intermediate VII-2

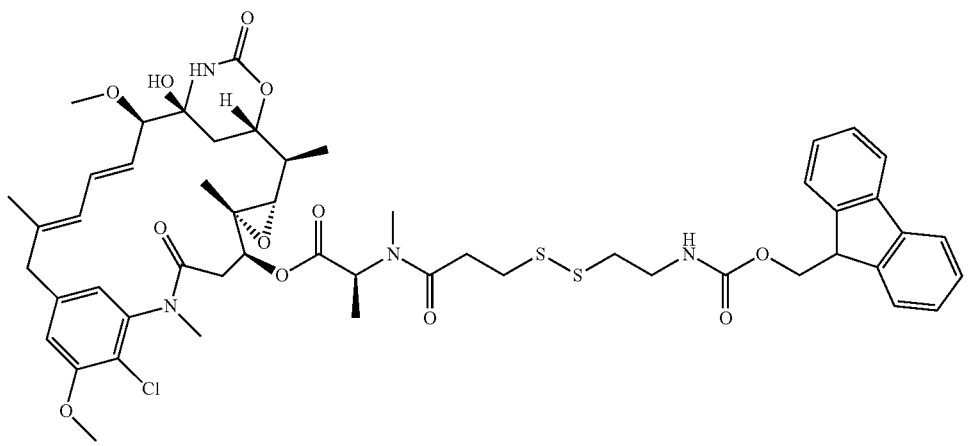

Intermediate VII-2 was prepared analogously to VII-1, using Intermediate V-2 in place of Intermediate V-1.

Synthesis of Intermediate VII-3

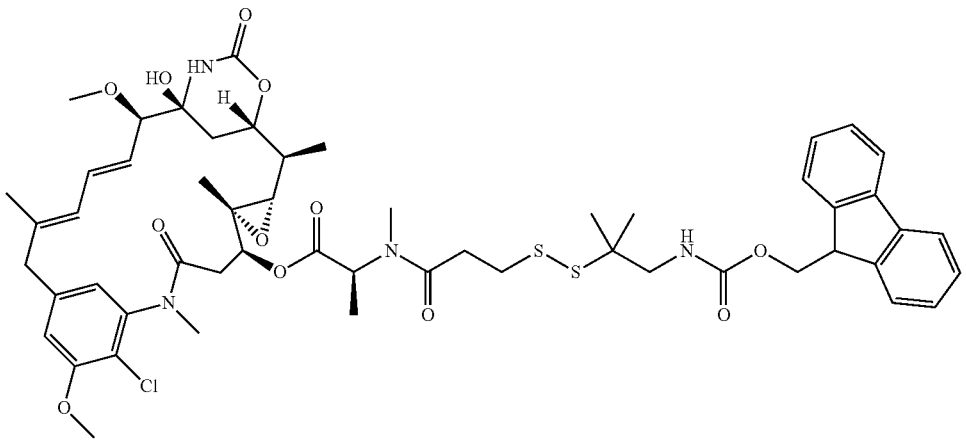

To a vial containing [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-[2-(9H-fluoren-9-ylmethoxycarbonylamino)ethyldisulfanyl]propanoyl-methyl-amino]propanoate (25.0 mg, 0.03 mmol) in 1 mL of CH$_3$CN was added 9H-fluoren-9-ylmethyl N-(2-methyl-2-sulfanyl-propyl)carbamate (14.5 mg, 0.044 mmol) and 4-methylmorpholine (0.120 mL, 1.09 mmol). The mixture was stirred for 16 h. LC-MS analysis indicated the desired material was formed. The mixture was concentrated, dissolved in 50 mL of EtOAc and washed with 1×25 mL of sat. NH$_4$Cl and 1×25 mL of sat. brine. The organic phase was dried with MgSO$_4$, filtered and concentrated. The crude residue was purified (SiO$_2$, 0-100% EtOAc/hexanes) to [(1S,2R,3 S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-[[2-(9H-fluoren-9-ylmethoxycarbonylamino)-1,1-dimethyl-ethyl]disulfanyl]propanoyl-methyl-amino]propanoate (0.0313 g, yield: 100%). MS m/z 1085.0 [M+Na]$^+$.

Synthesis of Intermediate VIII-1 (BOC Deprotection)

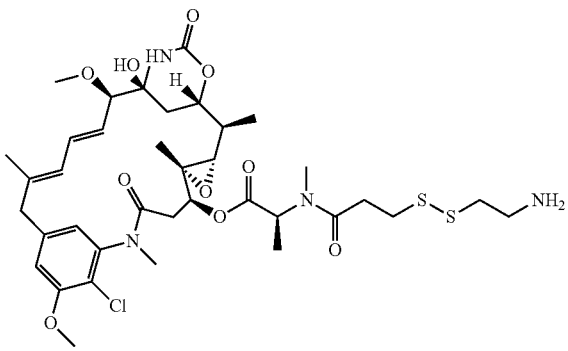

[(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-[2-(tert-butoxycarbonylamino)ethyldisulfanyl]propanoyl-methyl-amino]propanoate (31.9 mg, 0.05 mmol) was dissolved in 0.3/0.1/0.1 mL of CH$_3$CN/H$_2$O/TFA. The mixture was stirred for 36 h. LC-MS indicated complete deprotection. The mixture was purified by prep HPLC (20-95% CH$_3$CN/H$_2$O w/0.05% TFA) to give [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-(2-aminoethyldisulfanyl)propanoyl-methyl-amino]propanoate; 2,2,2-trifluoroacetic acid (22.9 mg, yield: 70.7%). MS m/z 813.2 [M+H]$^+$.

Alternative Synthesis of Intermediate VIII-1 (FMOC Deprotection)

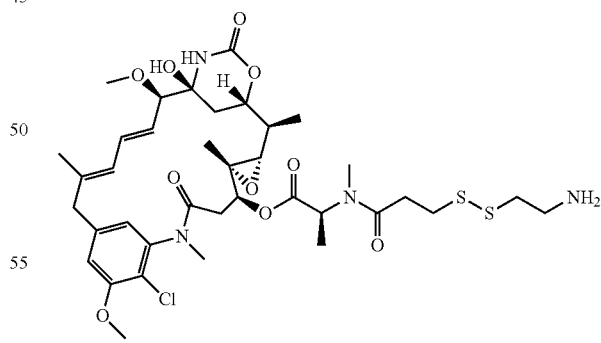

To a vial containing [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-[2-(9H-fluoren-9-ylmethoxycarbonylamino)ethyldisulfanyl]propanoyl-methyl-amino]propanoate (Intermediate VII-2; 29.6 mg, 0.03 mmol) was added 0.5 mL of DMF and 4-methylmorpholine (0.120 mL, 1.09 mmol).

The mixture was heated for 16 h at 40° C. LC-MS confirmed complete deprotection. The mixture was purified by (20-95% CH₃CN/H₂O w/0.05% TFA) to give [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-(2-aminoethyldisulfanyl)propanoyl-methyl-amino]propanoate trifluoroacetate (22.9 mg, yield: 86.4%). MS m/z 813.2 [M+H]⁺.

Synthesis of Intermediate VIII-2

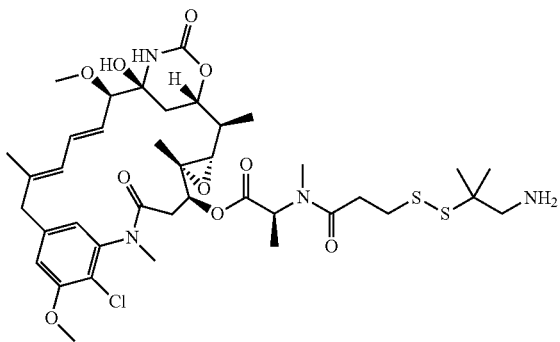

Intermediate VIII-2 was prepared analogously to Intermediate VIII-1. MS m/z 841.2 [M+H]⁺.

Synthesis of Intermediate X-1

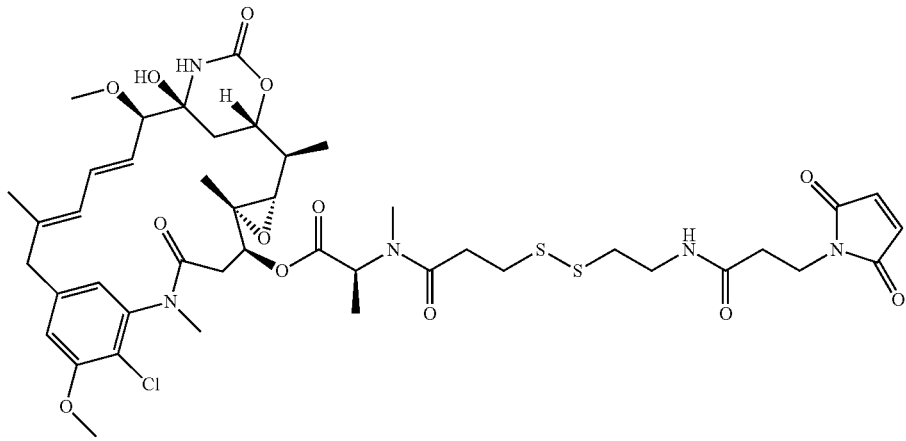

To [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-(2-aminoethyldisulfanyl)propanoyl-methyl-amino]propanoate trifluoroacetate (Intermediate VIII-1; 45.8 mg, 0.05 mmol) in 1 mL of DMF was added 3-(2,5-dioxopyrrol-1-yl)propanoic acid (12.5 mg, 0.074 mmol), TBTU (23.8 g, 0.074 mmol) and DIPEA (0.0169 mL, 0.1 mmol). LC-MS indicated complete conversion to the product. The mixture was diluted with 50 mL of EtOAc. This was washed with 1×25 mL sat NH₄Cl, 4×25 mL H₂O and 1×25 mL of H₂O. The organic phase was dried with MgSO₄, filtered and concentrated. The crude product was purified (SiO₂, 0-10% MeOH/CL₂Cl₂) to give [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110, 14.03,5]hexacosa-10(26),11,13,16,18-pentaen-6-yl] (2S)-2-[3-[2-[3-(2,5-dioxopyrrol-1-yl)propanoylamino] ethyldisulfanyl]propanoyl-methyl-amino]propanoate (17.3 mg, yield: 36.5%) MS m/z 986.1 [M+Na]⁺.

Example 2: Synthesis of Compound 2

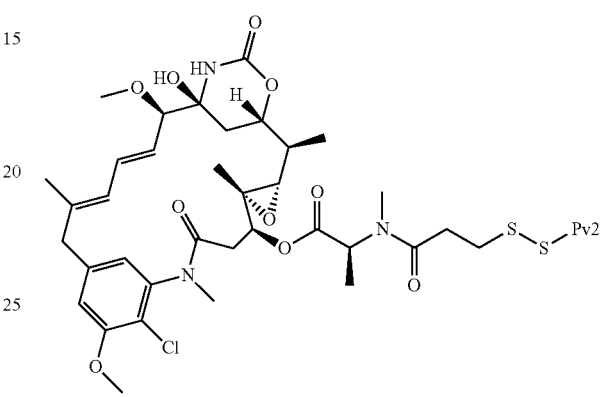

To a vial containing Pv2 (25.0 mg, 0.006 mmol; as a free flowing solid) and [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110, 14.03,5]hexacosa-10(26),11,13,16,18-pentaen-6-yl] (2S)-2-[methyl-[3-(2-pyridyldisulfanyl)propanoyl]amino] propanoate (7.70 mg, 0.009 mmol) was added 1 mL of degassed DMF and 0.5 mL degassed H₂O. To this was added CH₃CO₂H (0.0103 mL, 0.180 mmol). The mixture was stirred for 72 h. LC-MS indicated formation of desired product. The mixture was purified by prep HPLC (Sunfire C18 150×30 mm; 20-77% H₂O/Acetonitrile w/0.5% AcOH modifier; 15 min run; Flow rate: 30 ml/min; Wavelength=217 nM) to give the desired conjugate (17.0 mg, yield: 59.1%).

Example 6: Synthesis of Compound 6

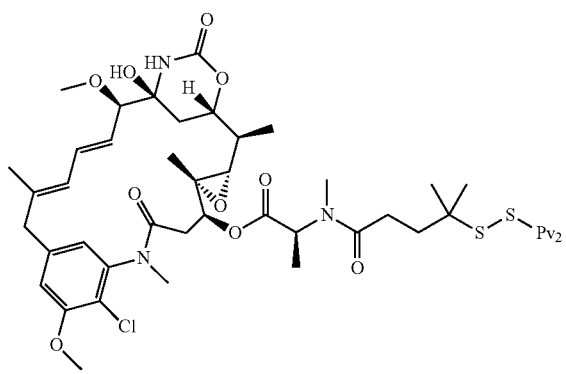

To a vial containing Pv2-SPyr (Intermediate II-2; 27.0 mg, 6.55e-6 mol) and [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10,12,14(26),16,18-pentaen-6-yl] (2S)-2-[methyl-(4-methyl-4-sulfanyl-pentanoyl)amino]propanoate (7.67 mg, 0.01 mmol). To this was added 1 mL of degassed DMF and 0.5 mL degassed $H_2O$. To this was added $CH_3CO_2H$ (0.015 mL, 0.262 mmol). The mixture was stirred for 72 h. LC-MS indicated formation of desired product. The mixture was purified by prep HPLC (Sunfire C18 150×30 mm; 20-80% $H_2O$/Acetonitrile w/0.5% AcOH modifier; 16 min run; Flow rate: 30 ml/min; Wavelength=217 nM) to give the desired conjugate (11.4 g, yield: 36.6%).

Example 9. Synthesis of Compound 9

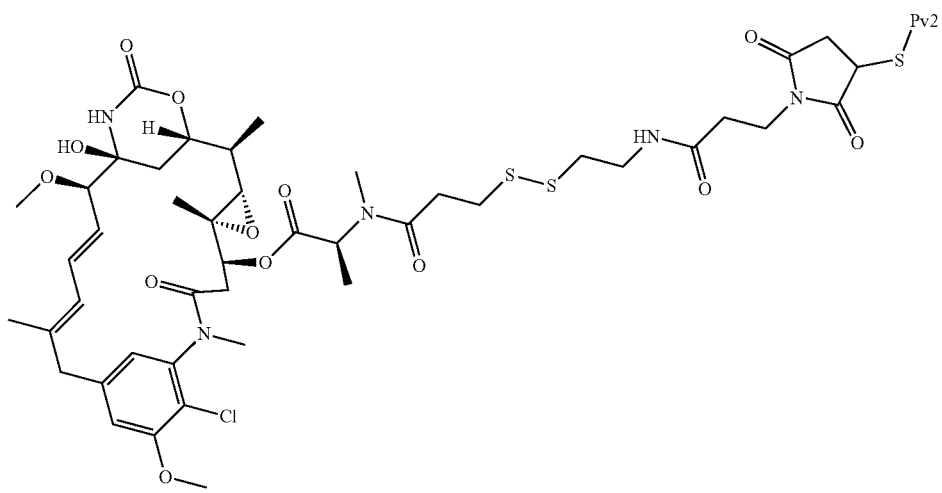

To a vial containing Pv2 (25.0 mg, 0.006 mol; as a free flowing solid) and [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10(26),11,13,16,18-pentaen-6-yl] (2S)-2-[3-[2-[3-(2,5-dioxopyrrol-1-yl)propanoylamino]ethyldisulfanyl]propanoyl-methyl-amino]propanoate (Intermediate X-1; 0.00877 g, 0.01 mmol) was added 1 mL of $CH_3CN$. The mixture was heterogeneous. To this was added 0.5 mL of $CH_3CN$, 0.5 mL of $H_2O$ and 0.5 mL of MeOH. Homogeneity was not achieved. The mixture was stirred rigorously for 72 h. LC-MS indicated formation of desired product. The mixture was purified by prep HPLC (Sunfire C18 150×30 mm; 45-61% $H_2O$/Acetonitrile w/0.05% TFA modifier; 13 min run; Flow rate: 30 ml/min; Wavelength=217 nM) to give desired conjugate (21.1 mg, yield: 70.0%).

Compounds 1, 3, and 4 were synthesized analogously to the compound of Compound 2, using Pv1, Pv3, and Pv4, respectively. Compounds 5, 7, and 8 were synthesized analogously to Compound 6, using Intermediates II-1, II-3, and II-6, respectively.

TABLE 4

Example Compounds

| Compound | Structure | MS  A: Maldi-TOF (M+)  B: ESI (m/z = 3) | Conditions  % ACN/H₂O  Run Time  RT |
|---|---|---|---|
| 1 | (structure with Pv1) | B: 1339.3 | D  20-95%  11 min  7.28 min |
| 2 | (structure with Pv2) | B: 1582.7 | A  20-95%  11 min  7.0 min |
| 3 | (structure with Pv3) | B: 1483.8 | D  20-95%  11 min  7.82 min |

TABLE 4-continued

Example Compounds

| Compound | Structure | MS<br>A: Maldi-TOF (M+)<br>B: ESI<br>(m/z = 3) | Conditions<br>% ACN/H$_2$O<br>Run Time<br>RT |
|---|---|---|---|
| 4 | 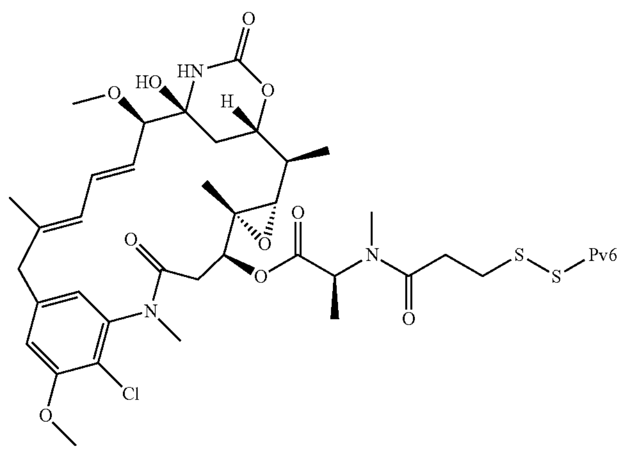 | B:<br>1659.4 | A<br>20-95%<br>11 min<br>6.92 min |
| 5 | 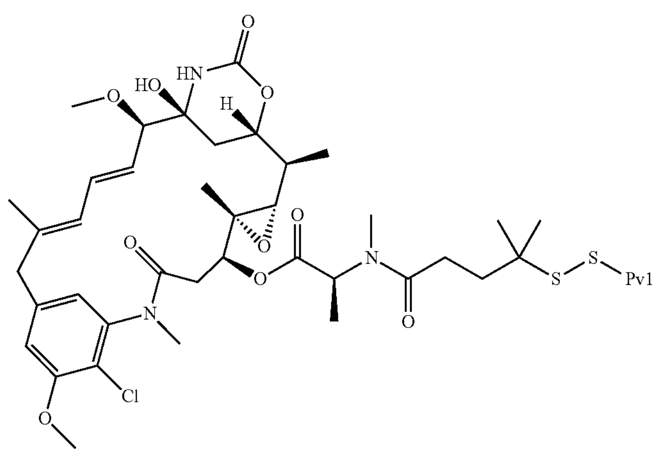 | B:<br>1352.8 | A<br>20-95%<br>11 min<br>6.81 min |
| 6 | 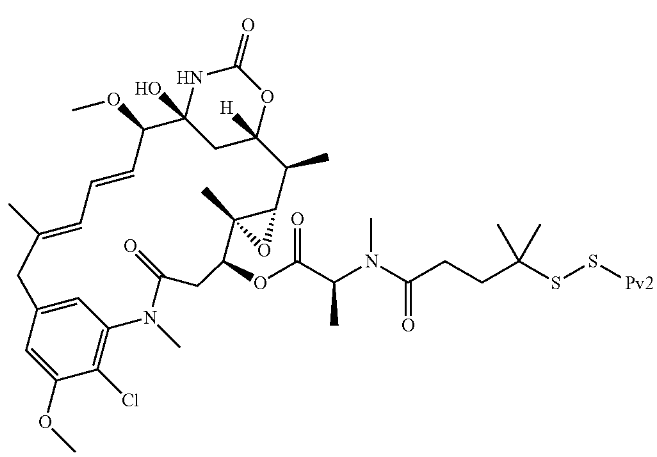 | B:<br>1597.0 | A<br>20-95%<br>11 min<br>7.44 min |

TABLE 4-continued

Example Compounds

| Compound | Structure | MS<br>A: Maldi-TOF (M+)<br>B: ESI<br>(m/z = 3) | Conditions<br>% ACN/H$_2$O<br>Run Time<br>RT |
|---|---|---|---|
| 7 | 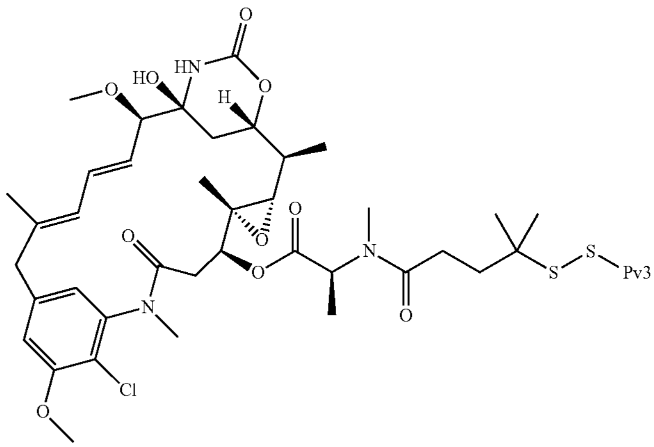 | B:<br>1487.1 | A<br>20-95%<br>11 min<br>6.60 min |
| 8 | 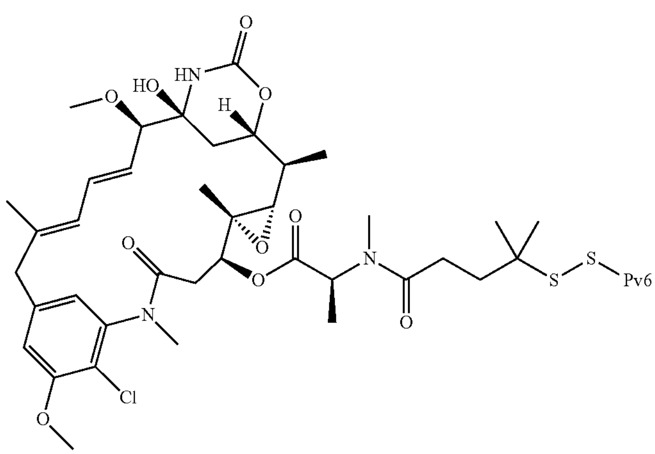 | B:<br>1673.4 | A<br>20-95%<br>11 min<br>7.14 min |

TABLE 4-continued

Example Compounds

| Compound | Structure | MS<br>A: Maldi-TOF (M+)<br>B: ESI (m/z = 3) | Conditions<br>% ACN/H$_2$O<br>Run Time<br>RT |
|---|---|---|---|
| 9 | 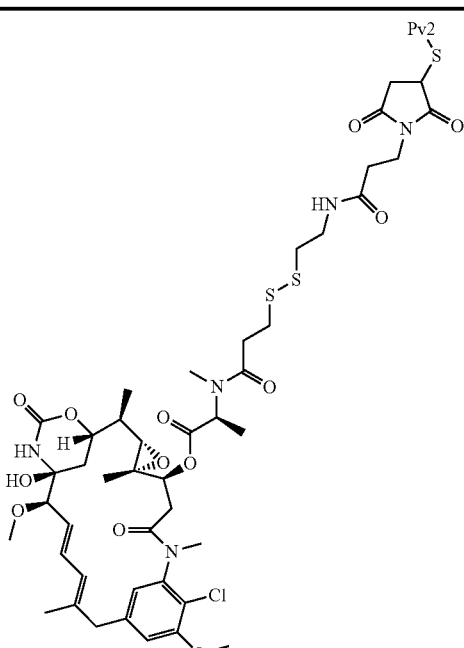 | B: 1659.4 | A<br>20-95%<br>11 min<br>7.16 min |

Example 5: Detailed Synthesis of Compound 5

To Pv1 (50.0 mg, 1.48e-5 mol) and [(1S,2R,3S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.110,14.03,5]hexacosa-10,12,14(26),16,18-pentaen-6-yl] (2S)-2-[methyl-(4-methyl-4-sulfanyl-pentanoyl)amino]propanoate (0.0150 g, 1.92e-5 mol) in 3 mL of 2:1 CH$_3$CN/H$_2$O was added N-methylmorpholine (0.0600 mL, 0.000546 mol). The mixture was stirred for 36 h. LC-MS analysis indicated formation of the desired material. The mixture was purified by Gilson prep HPLC (Sunfire C18 30×150 mm; 20-80% CH$_3$CN/H$_2$O w/0.05% TFA; 16 min run; 13.5 min) to give desired conjugate. The mixture was purified by Gilson prep HPLC (Sunfire C18 30×150 mm; 20-72% CH$_3$CN/H$_2$O w/0.05% TFA; 15 min run; 12.5 min; retention time: 6.847 min) to give Compound 5 (0.0322 g, 7.94e-6 mol, yield: 53.8%). ESI (m/z=3): 1352.8.

Example 5a: Alternative Synthesis of Compound 5

Step 1. Preparation of Pv1-S-Pyridyl

Peptide Pv1 and 2,2'-dipyridyl disulfide were dissolved in MeOH and the reaction was stirred overnight. LC-MS indicated the desired product was formed. The reaction mixture was concentrated and the residue was taken up in DMSO and purified by reverse phase column chromatography (40-75% ACN/H$_2$O (0.5% AcOH), 15 min) to give 212 mg of the desired product.

Step 2. Preparation of Compound 5

To a vial containing Pv1-SPyr (25.0 mg, 736e-6 mol) and [(1S,2R,3S,6S,16E,18E,20R,21S)-11-chloro-21-hydroxy12,20-dimethoxy-2,5,9,16-tetramethyl-8,23-dioxo-4,24-dioxa-9,22-diazatetracyclo[19.3.1.110,14.03,5]hexacosa10,12,14(26),16,18-pentaen-6-yl] (2S)-2-[methyl-(4-methyl-4-sulfanyl-pentanoyl)amino]propanoate (0.00864 g, 1.11e-5 mol). To this mixture was added 1 mL of degassed DMF and 0.5 mL degassed H$_2$O. CH$_3$CO$_2$H (0.017 mL, 0.000295 mol) was added. The mixture was stirred for 72 h. LC-MS indicated formation of the desired product. The mixture was purified by Gilson prep HPLC (Sunfire C18 30×150 mm; 20-80 CH$_3$CN/H$_2$O w/0.5% AcOH; 16 min run; 12.9 min) to give Compound 5 (0.00750 g, 1.85e-6 mol, yield: 25.1%).

Example 10: Synthesis of Compound 10

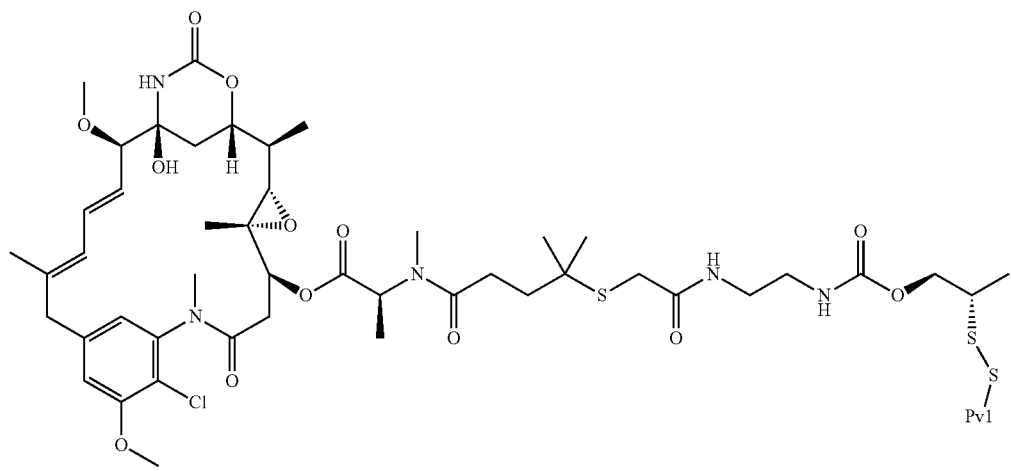

Step 1. (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl N-(4-((2-((2,5-dioxopyrrolidin-1-yl)oxy)-2-oxoethyl)thio)-4-methylpentanoyl)-N-methyl-L-alaninate

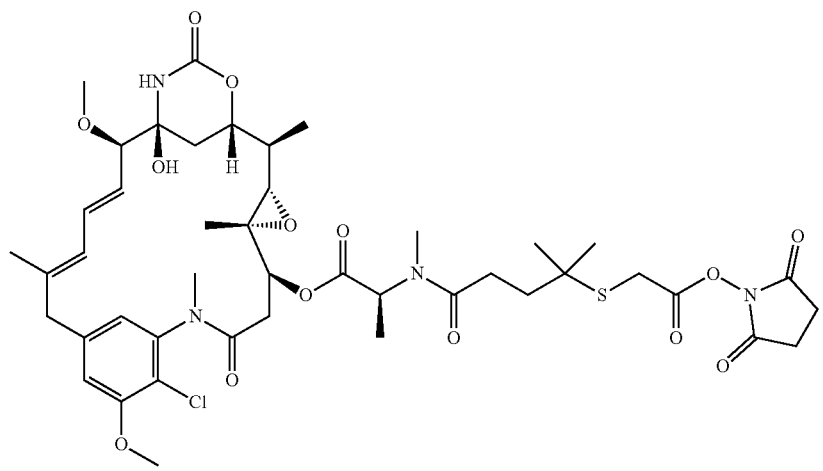

180 mg of DM4 (0.23 mmol) and 57 mg of bromoacetic acid N-hydroxysuccinimide ester (0.24 mmol) were dissolved in DMF (4.6 mL) and cooled in ice-water bath. 36.2 µL of DBU (0.24 mmol) was added at once and the mixture was allowed to warm to RT. At that moment LC/MS indicated nearly 95% conversion and the reaction was quenched with addition of 0.1 mL AcOH. Crude reaction mixture was directly loaded onto a 50 g C18 Aq column and purified via standard 10-100% B gradient (A: water w. 0.05% AcOH; B: water w. 0.05% AcOH). Product containing fractions were lyophilized to afford 160 mg of product (77% yield). HPLC purity at 254 nm: 96%. Retention time: 2.83 min (Method F). LCMS: 935.4 MH⁺.

Step 2. $1^4S,1^6S,3^2S,3^3S,2R,4S,10E,12E,14R$)-$8^6$-chloro-1+-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl N-(4-((2-((2-aminoethyl)amino)-2-oxoethyl)thio)-4-methylpentanoyl)-N-methyl-L-alaninate

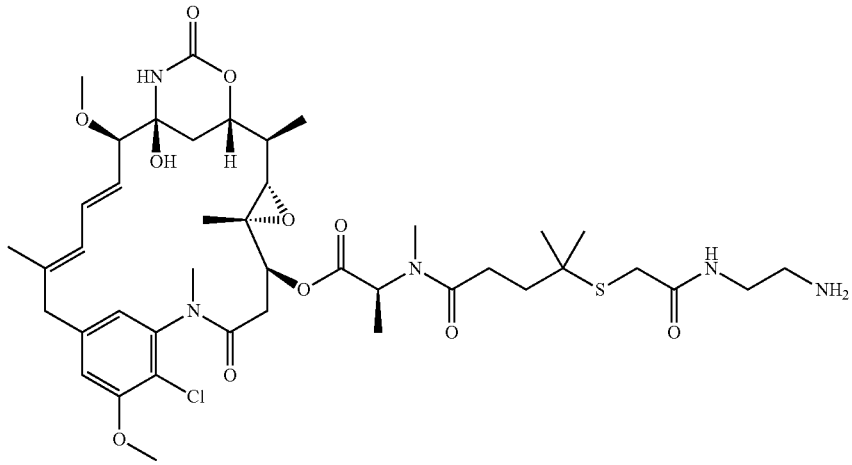

25 mg of $1^4S,1^6S,3^2S,3^3S,2R,4S,10E,12E,14R$)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl N-(4-((2-((2,5-dioxopyrrolidin-1-yl)oxy)-2-oxoethyl)thio)-4-methylpentanoyl)-N-methyl-L-alaninate (0.027 mmol) and 36 mg of N1-((4-methoxyphenyl)diphenylmethyl)ethane-1,2-diamine (0.11 mmol, 4 eq) were dissolved in dioxane (1 mL). After 3 h, the reaction appeared to be complete on LC/MS. The mixture was concentrated to dryness and dissolved in 80% AcOH in water (2 mL). LC/MS showed complete deprotection of the intermediate and the mixture was directly freeze-dried. The residue was dissolved in DMSO (1 mL) and loaded onto 15.5 g C18 Aq column and purified via standard 5-100% B gradient (A: water w. 0.05% AcOH; B: water w. 0.05% AcOH). Product containing fractions were lyophilized to afford 18 mg of product. HPLC purity at 254 nm: 95%. Retention time: 2.17 min (Method F). LCMS: 880.4 MH+.

Step 3. ($1^4S,1^6S,3^2S,3^3S,2R,4S,10E,12E,14R$)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl (2S,18S)-2,3,7,7-tetramethyl-4,10,15-trioxo-18-(pyridin-2-yldisulfaneyl)-16-oxa-8-thia-3,11,14-triazanonadecanoate

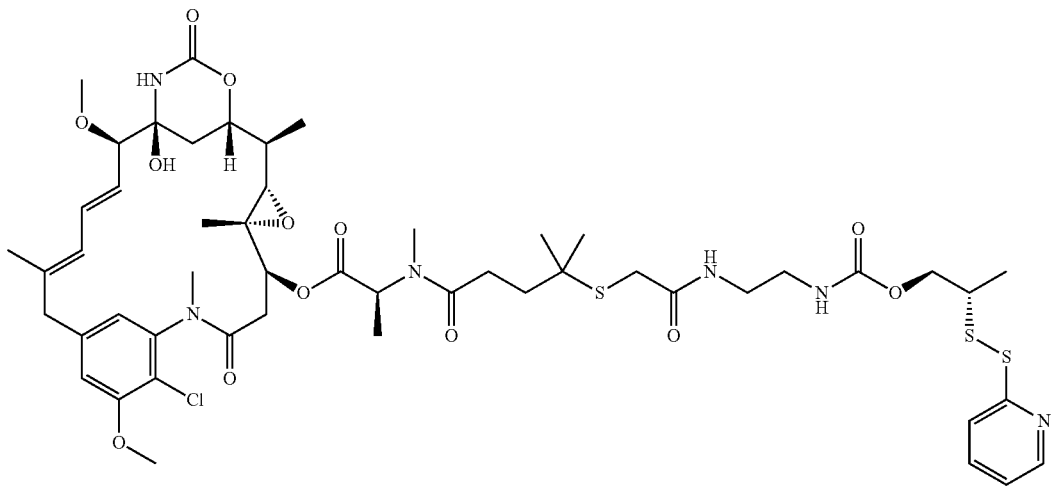

A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl N-(4-((2-((2-aminoethyl)amino)-2-oxoethyl)thio)-4-methylpentanoyl)-N-methyl-L-alaninate (14 mg, 0.016 mmol) in DMF (0.2 mL) was added to solid (S)-4-nitrophenyl (2-(pyridin-2-yldisulfaneyl)propyl) carbonate (6.6 mg, 0.018 mmol). Catalytic HOAt and DIEA (10 mL, 0.057 mmol) were added to the resultant solution and stirred at room temperature for 3 hours. The solution was neutralized with acetic acid (10 mL) and applied to a reverse phase column (RediSEP C18 (15.5 g)) and eluted with a gradient of acetonitrile (30% to 95%) in water with acetic acid (0.05%) to afford 18 mg (85% yield) of the title product. HPLC purity at 254 nm: 99%. Retention time: 2.85 min (Method F). LCMS: 1129.4 MNa⁺.

Step 4. Synthesis of Compound 10

A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (2S,18S)-2,3,7,7-tetramethyl-4,10,15-trioxo-18-(pyridin-2-yldisulfaneyl)-16-oxa-8-thia-3,11,14-triazanonadecanoate (17.7 mg, 0.00857 mmol) in DMF (1 mL) was treated with sodium bicarbonate (1.8 mg, 0.0214 mmol) and water (50 mL). The resultant solution was treated with peptide, Pv1 (31.5 mg, 0.0899 mmol) and stirred at room temperature for 3 hours, then applied to a reverse phase column, RediSep C18 (15.5 g) and eluted with a gradient of acetonitrile (30% to 70%) in water with ammonium acetate (10 mM). The fractions were combined, frozen and lyophilized to afford the product as a white solid, 18.7 mg (50%). HPLC purity at 254 nm: 99%. Retention time: 6.49 min (Method G) LCMS: 2138.0 (M+2H)/2⁺, 1425.3 (M+3H)/3⁺.

Example 11: Synthesis of Compound 11

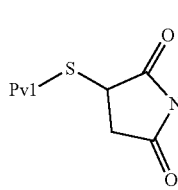
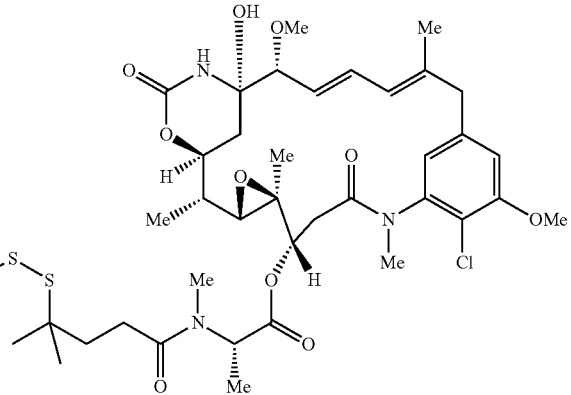

Step 1. (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl N-(4-((4-((2-(2,5-dioxo-2,5-dihydro-1H-pyrrol-1-yl)ethyl)amino)-4-oxobutyl)disulfaneyl)-4-methylpentanoyl)-N-methyl-L-alaninate

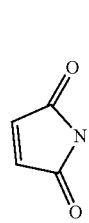
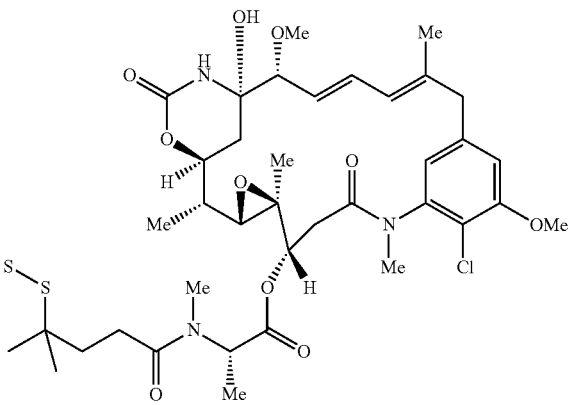

DM4 (10 mg, 0.013 mmol) and succinimidyl 4-(2-pyridyldithio)butanoate (6 mg, 0.02 mmol) were mixed in DMF (0.26 mL). Triethylamine was added (0.015 mL) and the mixture was stirred for 2 h. 1-(2-aminoethyl)-1H-pyrrole-2,5-dione hydrochloride (5 mg, 0.026 mmol) was added and after 3 h the mixture was directly loaded onto a RediSEP C18 Aq (15.5 g) column and eluted with a gradient of acetonitrile (30% to 95%) in water with acetic acid (0.05%) to afford 6 mg (40% yield) of the title product. HPLC purity at 254 nm: 92%. Retention time: 2.83 min (Method F). LCMS: 1020.4 MH$^+$.

Step 2. Synthesis of Compound 11

A solution of (1$^4$S,1$^6$S,3$^2$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl N-(4-((4-((2-(2,5-dioxo-2,5-dihydro-1H-pyrrol-1-yl)ethyl)amino)-4-oxobutyl)disulfaneyl)-4-methylpentanoyl)-N-methyl-L-alaninate (6 mg, 0.006 mmol) and Pv1 peptide (22.3 mg, 0.006 mmol) were dissolved in DMF (0.12 mL) and treated with triethylamine (0.001 mL). After 30 minutes the reaction mixture was directly loaded onto a RediSEP C8 (15.5 g) column and eluted with a gradient of acetonitrile (35% to 75%) in water with TFA (0.05%) to afford 16 mg (64% yield) of the title compound. HPLC purity at 254 nm: 98%. Retention time: 6.19 min (Method G). LCMS: 2150.2 (M+2H)/2$^+$, 1433.3 (M+3H)/3$^+$.

Example 12. Synthesis of Compound 12

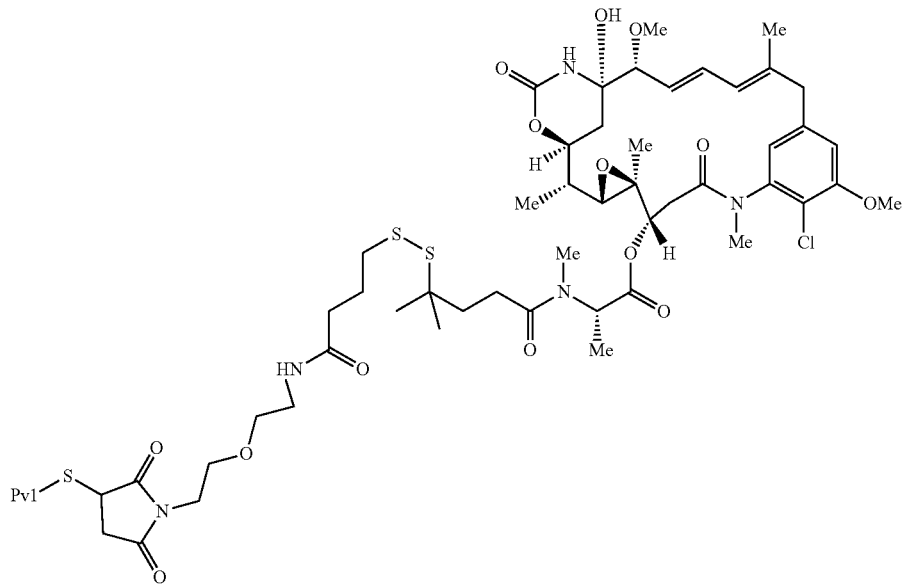

Step 1. ((1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-1-(2,5-dioxo-2,5-dihydro-1H-pyrrol-1-yl)-16,16,20,21-tetramethyl-10,19-dioxo-3,6-dioxa-14,15-dithia-9,20-diazadocosan-22-oate

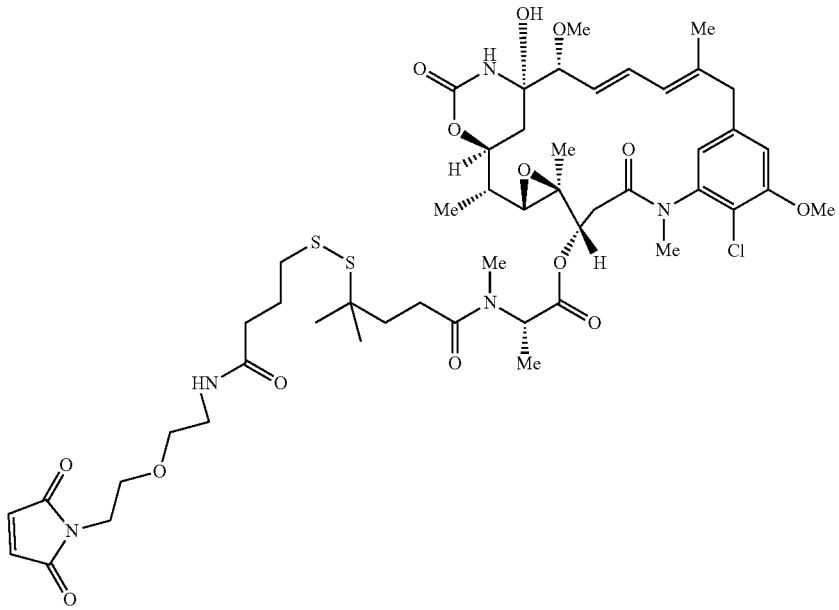 [SMILES: COc1cc2cc(c1Cl)N(C)C(=O)C[C@H](OC(=O)[C@H](C)N(C)C(=O)CCC(C)(C)SSCCCC(=O)NCCOCCN1C(=O)C=CC1=O)[C@]1(C)O[C@H]1[C@H](C)[C@@H]1C[C@@](O)(NC(=O)O1)[C@H](OC)/C=C/C=C(\C)C2]

DM4 (20 mg, 0.026 mmol) and succinimidyl 4-(2-pyridyldithio)butanoate (12 mg, 0.04 mmol) were mixed in DMF (0.75 mL). Triethylamine was added (0.045 mL) and the mixture was stirred for 2 h. 1-(21-(2-(2-(2-aminoethoxy)ethoxy)ethyl)-1H-pyrrole-2,5-dione hydrochloride (9 mg, 0.036 mmol) was added and after 3 h the mixture was directly loaded onto a RediSEP C18 Aq (15.5 g) column and eluted with a gradient of acetonitrile (30% to 95%) in water with acetic acid (0.05%) to afford 17 mg (61% yield). HPLC purity at 254 nm: 99%. Retention time: 2.84 min (Method F). LCMS: 1108.4 MH⁺.

Step 2. Synthesis of Compound 12

A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-1-(2,5-dioxo-2,5-dihydro-1H-pyrrol-1-yl)-16,16,20,21-tetramethyl-10,19-dioxo-3,6-dioxa-14,15-dithia-9,20-diazadocosan-22-oate (15 mg, 0.014 mmol) and Pv1 peptide (52 mg, 0.015 mmol) were dissolved in DMF (0.28 mL) and treated with triethylamine (0.006 mL). After 30 minutes the reaction mixture was directly loaded onto a RediSEP C8 (15.5 g) column and eluted with a gradient of acetonitrile (35% to 60%) in water with TFA (0.05%) to afford 25 mg (34% yield). HPLC purity at 254 nm: 98%. Retention time: 6.26 min (Method G). LCMS: 2194.0 (M+2H)/2⁺, 1463.0 (M+3H)/3⁺.

Example 13. Synthesis of Compound 13

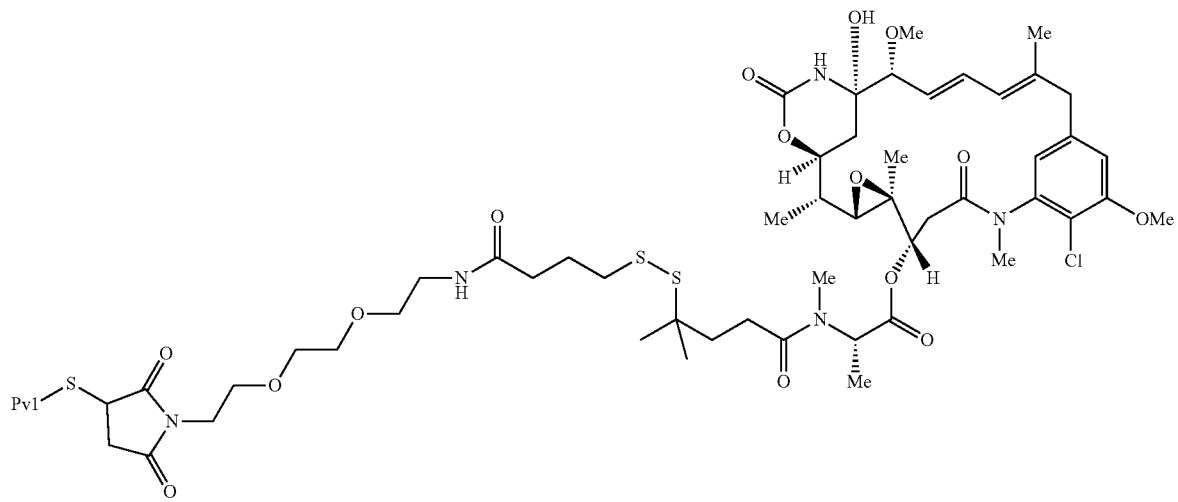

Step 1. 1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-1-(2,5-dioxo-2,5-dihydro-1H-pyrrol-1-yl)-13,13,17,18-tetramethyl-7,16-dioxo-3-oxa-11,12-dithia-6,17-diazanonadecan-19-oate

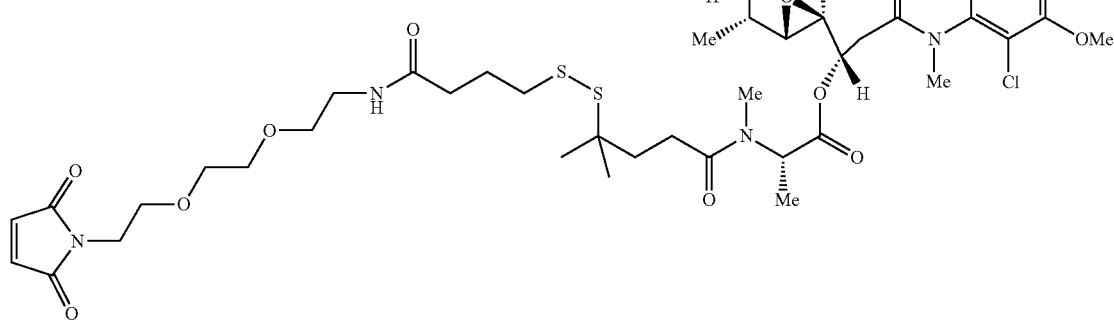

DM4 (20 mg, 0.026 mmol) and succinimidyl 4-(2-pyridyldithio)butanoate (12 mg, 0.04 mmol) were mixed in DMF (0.75 mL). Triethylamine was added (0.045 mL) and the mixture was stirred for 2 h. 1-(2-(2-aminoethoxy)ethyl)-1H-pyrrole-2,5-dione hydrochloride (5 mg, 0.024 mmol) was added and after 3 h the mixture was directly loaded onto a RediSEP C18 Aq (15.5 g) column and eluted with a gradient of acetonitrile (30% to 95%) in water with acetic acid (0.05%) to afford 13 mg (41% yield) of the title product. HPLC purity at 254 nm: 94%. Retention time: 2.85 min (Method F). LCMS: 1064.4 MH⁺.

Step 2. Synthesis of Compound 13

A solution of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl (S)-1-(2,5-dioxo-2,5-dihydro-1H-pyrrol-1-yl)-16,16,20,21-tetramethyl-10,19-dioxo-3,6-dioxa-14,15-dithia-9,20-diazadocosan-22-oate (18 mg, 0.017 mmol) and Pv1 peptide (63 mg, 0.019 mmol) were dissolved in DMF (0.34 mL) and treated with triethylamine (0.007 mL). After 30 minutes the reaction mixture was directly loaded onto a RediSEP C8 (15.5 g) column and eluted with a gradient of acetonitrile (35% to 60%) in water with TFA (0.05%) to afford 25 mg (34% yield) of the title compound. HPLC purity at 254 nm: 99%. Retention time: 6.24 min (Method G). LCMS: 2172.0 (M+2H)/2⁺, 1448.7 (M+3H)/3⁺.

Example 14. Synthesis of Compound 14

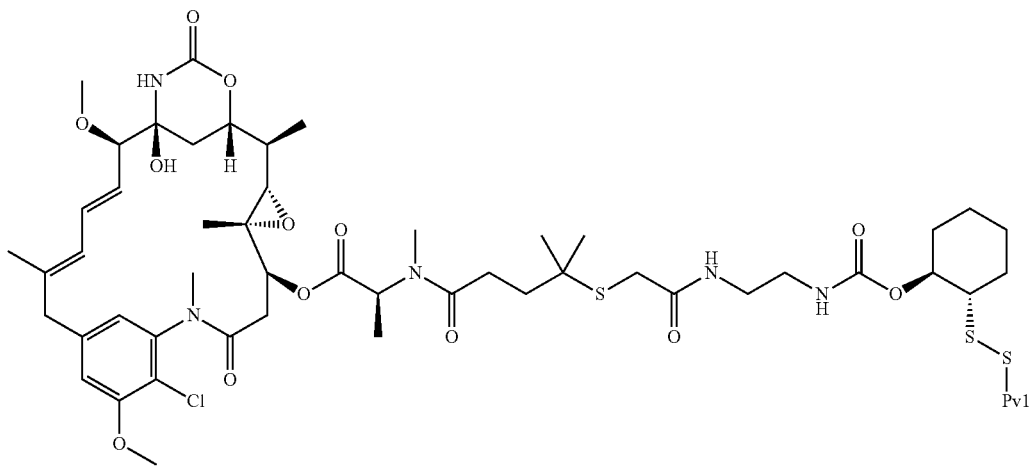

Step 1. (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-9,9,13,14-tetramethyl-1,6,12-trioxo-1-(((1S,2S)-2-(pyridin-2-yldisulfaneyl)cyclohexyl)oxy)-8-thia-2,5,13-triazapentadecan-5-oate A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl N-(4-((2-((2-aminoethyl)amino)-2-oxoethyl)thio)-4-methylpentanoyl)-N-methyl-L-alaninate (14 mg, 0.016 mmol; Example 10, Step 2) in DMF (0.2 mL) was added to solid 4-nitrophenyl ((1S,2S)-2-(pyridin-2-yldisulfaneyl)cyclohexyl) carbonate (7.2 mg, 0.018 mmol). Catalytic HOAt and DIEA (10 mL, 0.057 mmol) were added to the resultant solution and stirred at room temperature for 3 hours. The solution was neutralized with acetic acid (10 mL) and applied to a reverse phase column, RediSEP C18 (15.5 g) and eluted with a gradient of acetonitrile (30% to 95%) in water with acetic acid (0.05%) to afford 15 mg (80% yield) of the title compound. HPLC purity at 254 nm: 98%. Retention time: 3.05 min (Method F). LCMS: 1147.4 MH⁺.

Step 2. Synthesis of Compound 14

A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-

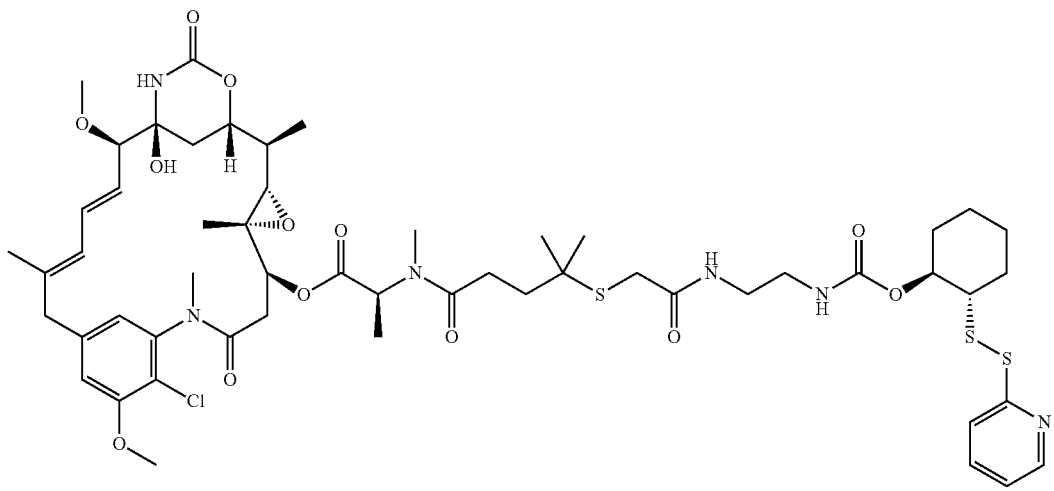

1²,6-dioxo-7-aza-1(6,4)-oxazinana-3(2,3)-oxirana-8(1,3)-benzenacyclotetradecaphane-10,12-dien-4-yl (S)-9,9,13,14-tetramethyl-1,6,12-trioxo-1-(((1S,2S)-2-(pyridin-2-yldisulfaneyl)cyclohexyl)oxy)-8-thia-2,5,13-triazapentadecan-15-oate (17 mg, 0.015 mmol) and Pvl peptide (47 mg, 0.013 mmol) were dissolved in DMF (0.34 mL) and treated with triethylamine (0.007 mL). After 30 minutes the reaction mixture was directly loaded onto a RediSEP C8 (15.5 g) column and eluted with a gradient of acetonitrile (35% to 60%) in water with TFA (0.05%) to afford 28 mg (37% yield). HPLC purity at 254 nm: 99%. Retention time: 7.36 min (Method G). LCMS: 2158.0 (M+2H)/2⁺, 1439.0 (M+3H)/3⁺.

Example 15. Synthesis of Compound 15

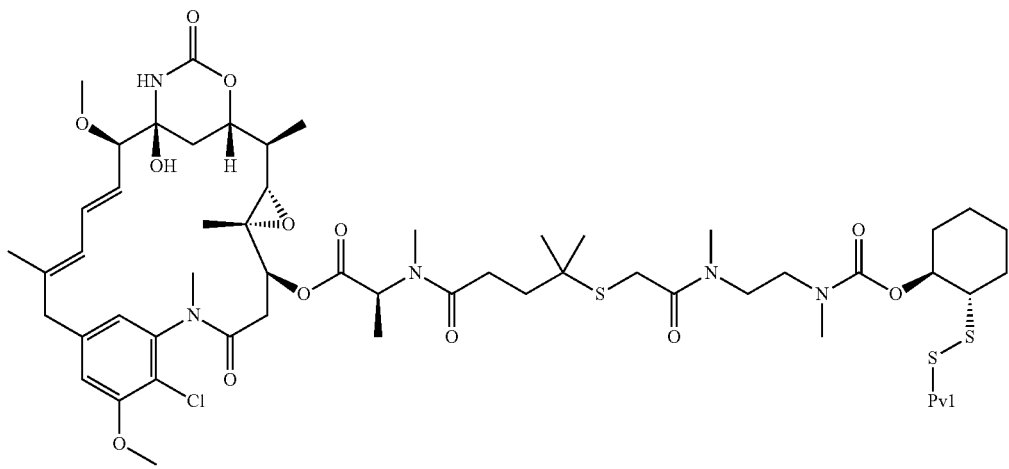

Step 1. (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-5,9,9,13,14-pentamethyl-6,12-dioxo-8-thia-2,5,13-triazapentadecan-15-oate

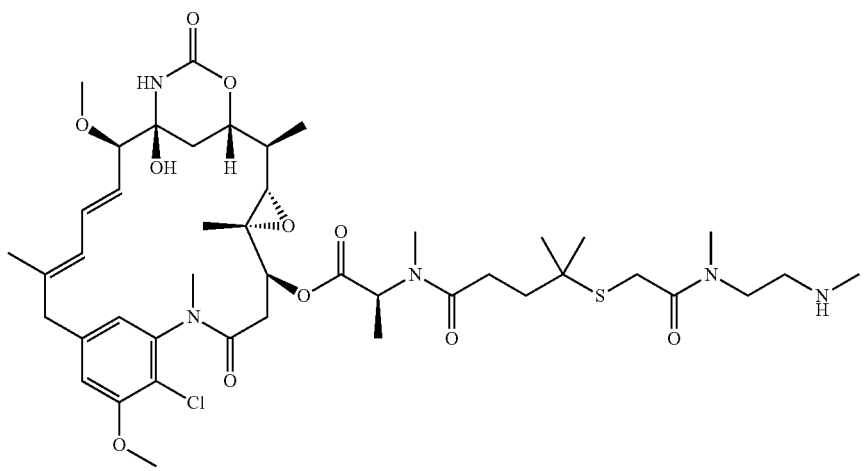

25 mg of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl N-(4-((2-((2,5-dioxopyrrolidin-1-yl)oxy)-2-oxoethyl)thio)-4-methylpentanoyl)-N-methyl-L-alaninate (0.027 mmol) and 40 mg of N1-((3-methoxyphenyl)diphenylmethyl)-N1,N2-dimethylethane-1,2-diamine (0.11 mmol, 4 eq) were dissolved in dioxane (1 mL). After 3 h, the reaction appeared to be complete on LC/MS. 0.05 mL of TFA was added and the mixture was loaded onto a 15.5 g C18 Aq column and purified via standard 5-100% B gradient (A: water w. 0.05% TFA; B: ACN w. 0.05% TFA). Product containing fractions were lyophilized to afford 22 mg of product (75% yield). HPLC purity at 254 nm: 98%. Retention time: 2.25 min (Method F). LCMS: 908.4 MH⁺.

Step 2. (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-2,5,9,9,13,14-hexamethyl-1,6,12-trioxo-1-(((1S,2S)-2-(pyridin-2-yldisulfaneyl)cyclohexyl)oxy)-8-thia-2,5,13-triazapentadecan-15-oate

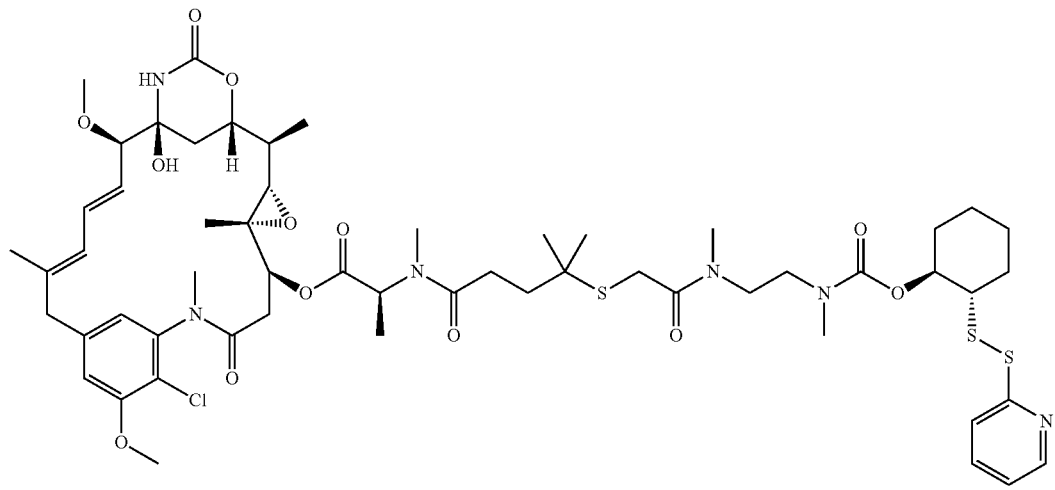

A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-5,9,9,13,14-pentamethyl-6,12-dioxo-8-thia-2,5,13-triazapentadecan-15-oate (15 mg, 0.016 mmol) in DMF (0.2 mL) was added to solid 4-nitrophenyl ((1S,2S)-2-(pyridin-2-yldisulfaneyl)cyclohexyl) carbonate (6.6 mg, 0.018 mmol). Catalytic HOAt and DIEA (10 mL, 0.057 mmol) were added to the resultant solution and stirred at room temperature for 3 hours. The solution was neutralized with acetic acid (10 mL) and applied to a reverse phase column, RediSEP C18 (15.5 g) and eluted with a gradient of acetonitrile (30% to 95%) in water with acetic acid (0.05%) to afford 16 mg (82% yield) of the title product. HPLC purity at 254 nm: 97%. Retention time: 3.36 min (Method F). LCMS: 1175.5 MH⁺.

Step 3. Synthesis of Compound 15

A solution of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (S)-2,5,9,9,13,14-hexamethyl-1,6,12-trioxo-1-(((1S,2S)-2-(pyridin-2-yldisulfaneyl)cyclohexyl)oxy)-8-thia-2,5,13-triazapentadecan-15-oate (16 mg, 0.014 mmol) and Pv1 peptide (52 mg, 0.015 mmol) were dissolved in DMF (0.28 mL) and treated with triethylamine (0.008 mL). After 30 minutes the reaction mixture was directly loaded onto a RediSEP C8 (15.5 g) column and eluted with a gradient of acetonitrile (35% to 60%) in water with TFA (0.05%) to afford 32 mg (44% yield) of the title compound. HPLC purity at 254 nm: 99%. Retention time: 6.86 min (Method G). LCMS: 2172.0 (M+2H)/2⁺, 1448.4 (M+3H)/3⁺.

Example 16. Synthesis of Compound 16

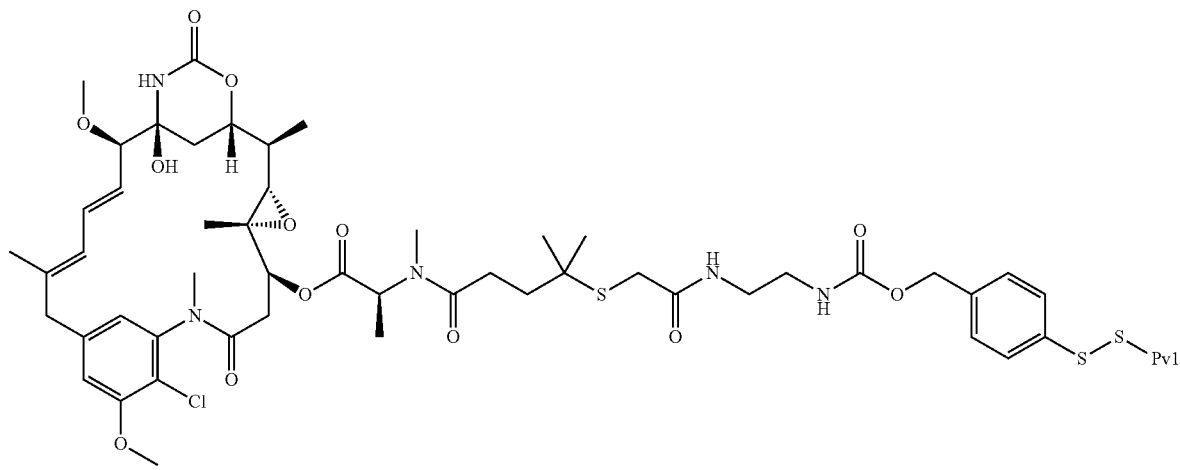

Step 1. (4-((5-nitropyridin-2-yl)disulfaneyl)phenyl)methanol

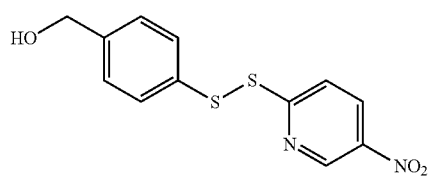 [SMILES: O=[N+]([O-])c1ccc(SSc2ccc(CO)cc2)nc1]

A solution of (4-mercaptophenyl)methanol (0.74 g, 4.83 mmol) in THF (10 mL) was treated with 5-nitro-2-((4-nitrophenyl)disulfaneyl)pyridine (1.0 g, 3.23 mmol). The resultant suspension was stirred at room temperature for 2 hours, and the solvent was evaporated in vacuo. The residue was dissolved in DCM and applied to a RediSep silica gel column and eluted with a gradient of ethyl acetate (10% to 60%) in hexanes to afford the product (0.499 g, 52% yield). HPLC purity at 254 nm: 90%. Retention time: 2.72 min (Method F). MS data, 295.1 (M+H)$^+$. $^1$HNMR (DMSO-d$_6$) δ 9.18 (s, 1H), 8.58 (d of d, 1H), 8.02 (d, 1H), 7.56 (d, 2H), 7.34 (d, 2H), 5.24 (t, 1H) and 4.47 (d, 2H).

Step 2. 4-nitrophenyl (4-((5-nitropyridin-2-yl)disulfaneyl)benzyl) carbonate

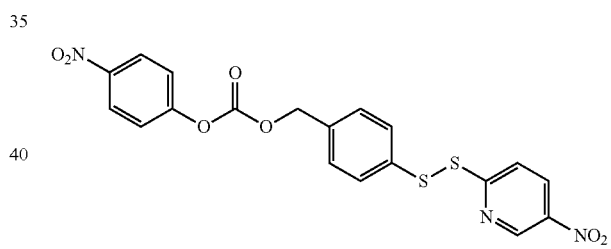

A solution of 4-nitrophenyl chloroformate (255 mg, 1.26 mmol) in THF (5 mL) was cooled on an ice-bath and treated with a solution (4-((5-nitropyridin-2-yl)disulfaneyl)phenyl)methanol (220 mg, 0.748 mmol), triethyl amine (0.7 mL, 5.03 mmol), and 4-dimethyaminopyridine (45 mg, 0.368 mmol) in THF (5 mL) added over about 15 minutes. The ice-bath was removed, and the solution was stirred at room temperature for one hour and stored in a freezer overnight. The solvent was evaporated in vacuo, and the residue was dissolved in DCM, applied to a RediSep silica gel column (12 g) and eluted with a gradient of ethyl acetate (2% to 100%) in hexanes. The product was purified further by reverse phase chromatography on a RediSep C18 cartridge (50 g) eluted with a gradient of acetonitrile (30% to 95%) in water with acetic acid (0.05%), to afford the product, 55 mg (16%). HPLC purity at 254 nm: >99%. Retention time: 3.77 min (Method F). MS data, 460.7 (M+H)$^+$. $^1$HNMR(CDCl$_3$) δ 9.29 (d, 1H), 8.39 (d of d, 1H), 8.28 (d of d, 2H), 7.83 (d of d, 1H), 7.55 (d of d, 2H), 7.44 (d of d), 7.36 (d of d, 2H) and 5.26 (d, 2H).

Step 3. (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl (S)-11,11,15,16-tetramethyl-1-(4-((5-nitropyridin-2-yl)disulfaneyl)phenyl)-3,8,14-trioxo-2-oxa-10-thia-4,7,15-triazaheptadecan-17-oate 6.63 min (Method G). MS data, 2162.4 (M+2H)/2$^+$, 1441.8 (M+3H)/3$^+$, 1082.6 (M+4H)/4$^+$, 1435.7 (M+3H−H$_2$O)/3$^+$.

Example A. Growth Delay Assay

Cells were plated in 96 well black walled-clear bottom plates (Griener), DLD-1 WT cells at 2500 cells per well, FaDu, and HeLa cells at 5000 cells per well, and HCT116

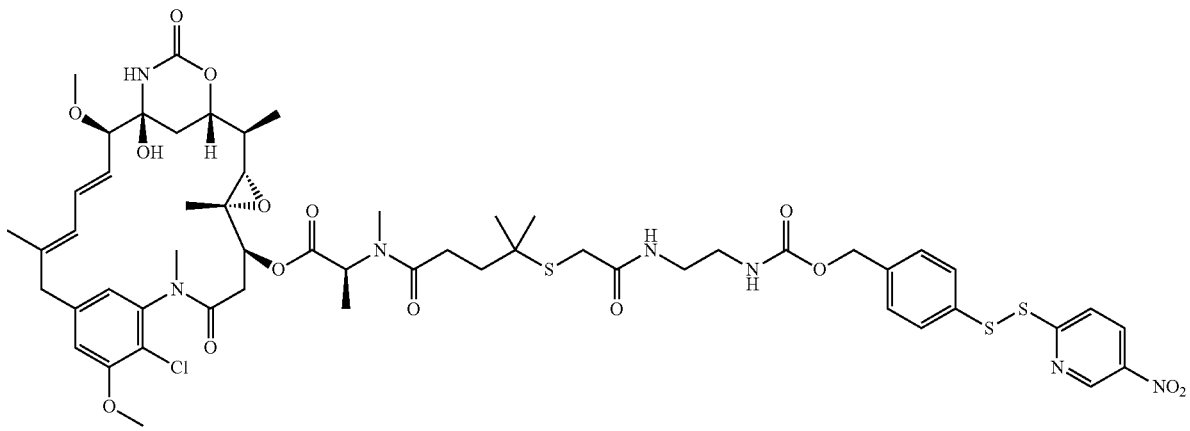

A solution of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-((2-aminoethyl)amino)-2-oxoethyl)thio)-4-methylpentanoyl)-N-methyl-L-alaninate (15 mg, 0.017 mmol; Example 10, Step 2) in DMF (1 mL) was added to solid 4-nitrophenyl (4-((5-nitropyridin-2-yl)disulfaneyl)benzyl) carbonate (26 mg, 0.0566 mmol). Catalytic HOAt and DIEA (10 mL, 0.057 mmol) were added to the resultant solution and stirred at room temperature for 3 hours. The solution was neutralized with acetic acid (7 mL, 0.122 mmol) and applied to a reverse phase column, RediSEP C18 (15.5 g) and eluted with a gradient of acetonitrile (30% to 95%) in water with acetic acid (0.05%). Further purification on a silica gel column, RediSep (4 g), using a gradient of methanol (0.2% to 6%) in DCM as the eluant, afforded the title product (10.3 mg, 50% yield). HPLC purity at 254 nm: >99%. Retention time: 3.16 min (Method F). MS data, 1182.3 (M+H−H$_2$O)$^+$, 1201.3 (M+H)$^+$, 1222.3 (M+Na)$^+$.

Step 4. Synthesis of Compound 16

A solution of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl (S)-11,11,15,16-tetramethyl-1-(4-((5-nitropyridin-2-yl)disulfaneyl)phenyl)-3,8,14-trioxo-2-oxa-10-thia-4,7,15-triazaheptadecan-17-oate (10.3 mg, 0.00857 mmol) in DMF (1 mL) was treated with sodium bicarbonate (1.8 mg, 0.0214 mmol) and water (50 mL). The resultant solution was treated with peptide, Pv1 (31.5 mg, 0.0899 mmol) and stirred at room temperature for 3 hours, then applied to a reverse phase column, RediSep C18 (15.5 g) and eluted with a gradient of acetonitrile (30% to 70%) in water with ammonium acetate (10 mM). The fractions were combined, frozen and lyophilized to afford the product as a white solid, 18.7 mg (50%). HPLC purity at 254 nm: 99%. Retention time:

at 3000 cells per well, in growth media containing 1000 FBS. Cells were allowed to adhere at room temperature for 60 minutes before returning to a 37 C, 5% CO$_2$ incubator. After 24 hours, media was removed and replaced with fresh growth media containing various drug concentrations. Each drug concentration was added in triplicate. Non-drug treated controls contained growth media only. Cells were returned to the incubator. Ninety-six hours after addition of drug, cells were fixed with 40% paraformaldehyde for 20 minutes and stained with Hoechst at 1 µg/mL. The plates were imaged on a Cytation 5 auto imager (BioTek) and cells were counted using CellProfiler (http://cellprofiler.org). The percent cell growth delay was calculated and data plotted using GraphPad Prism

TABLE 5

Growth Delay Assay data

| Example | DLD-1 (IC$_{50}$, nM) | HCT116 (IC$_{50}$, nM) | FaDu (IC$_{50}$, nM) | HeLa (IC$_{50}$, nM) |
|---|---|---|---|---|
| R$^2$SH-1 (see Table 2) | 9.8 | 4.3 | 2.8 | 2.6 |
| R$^2$SH-2 (see Table 2) | 0.45 | 0.20 | 0.13 | 0.02 |
| 1 | 60.5 | 21.8 | 10.4 | 7.4 |
| 2 | 114 | 21.1 | 15.4 | 8.0 |
| 3 | 45.1 | 19.3 | 10.1 | 6.9 |
| 4 | 11.7 | 2.5 | 1.4 | 0.85 |
| 5 | 9.4 | 2.7 | 2.3 | 0.95 |
| 6 | 8.3 | 3.3 | 5.2 | 1.8 |
| 7 | NC* | 3.4 | 4.6 | 2.0 |
| 8 | 9.8 | 3.0 | 3.4 | 1.6 |

NC* = Not calculated

Example B: Effect on In Vitro Tubulin Polymerization

A fluorescence-based tubulin polymerization assay (Cytoskeleton Cat #BK011P) was performed to quantitate the impact of unconjugated DM4 and Compound 5 on in vitro tubulin polymerization. DM4 and Compound 5 were prepared as 10 mM stocks in DMSO then diluted at 10× to 200, 50 and 5 µM in ultrapure distilled water for a final DMSO concentration of 0.2%. Kit reagents were defrosted rapidly then kept cold on ice to prevent premature polymerization. A tubulin reaction mixture was prepared on ice by mixing purified porcine brain tubulin, GTP, and glycerol buffer all in 1× kit buffer for final concentrations of 2 mg/mL tubulin, 1 mM GTP and 15% glycerol. 5 µL of DM4, Compound 5 or DMSO control were added to a pre-warmed black, half-well reaction plate at 37° C. for no longer than 1 minute, to warm, but not allow for evaporation. 50 µL of tubulin reaction mixture was rapidly added to each well and immediately placed in a pre-warmed Cytation 5 imaging reader (BioTek). A kinetic reading was performed at 360 excitation/450 emission for 2 hours at 37° C., with readings every 2.5 minutes to follow the enhancement of fluorescence due to incorporation of a fluorescent reporter into microtubules as polymerization occurs.

FIG. 1 shows a plot of the effect of free DM4 and Compound 5 on in vitro β-tubulin polymerization (in terms of relative fluorescence units) at 0.5 µM, 5 µM, and 20 µM.

Example C: Kinetic Analysis of Conjugate Binding

Binding experiments were performed using a Biacore S200 instrument. A Series S sensor chip with pre-immobilized streptavidin was conditioned with 1 M NaCl in 50 mM NaOH. Biotin-labeled human tubulin derived from HeLa cells was immobilized to the sensor chip at a concentration of 125 µg/mL in HBS-P+ buffer at a flow rate of 10 µl/min. A final 3000 RU (response units) of protein was directly immobilized to the chip. After tubulin immobilization, the sensor chip was washed with 50% isopropanol, 50 mM NaOH and 1 M NaCl and subsequently allowed to equilibrate in assay buffer for 4 hours. A streptavidin-biotin capture blank (reference FC) was used to monitor non-specific binding.

To collect kinetic binding data, Compound 5 diluted in assay buffer was injected over the flow cells at concentrations ranging from 100 µM to 0.048 µM and 50 µM to 0.024 µM, at a flow rate of 60 µL/minute and a temperature of 25° C. The complex was allowed to dissociate for 60 seconds. Binding of compound to tubulin was monitored in real time to obtain on (Ka) and off (Koff) rates. The affinity constant (KD) was calculated by steady state kinetics.

Figure 2:
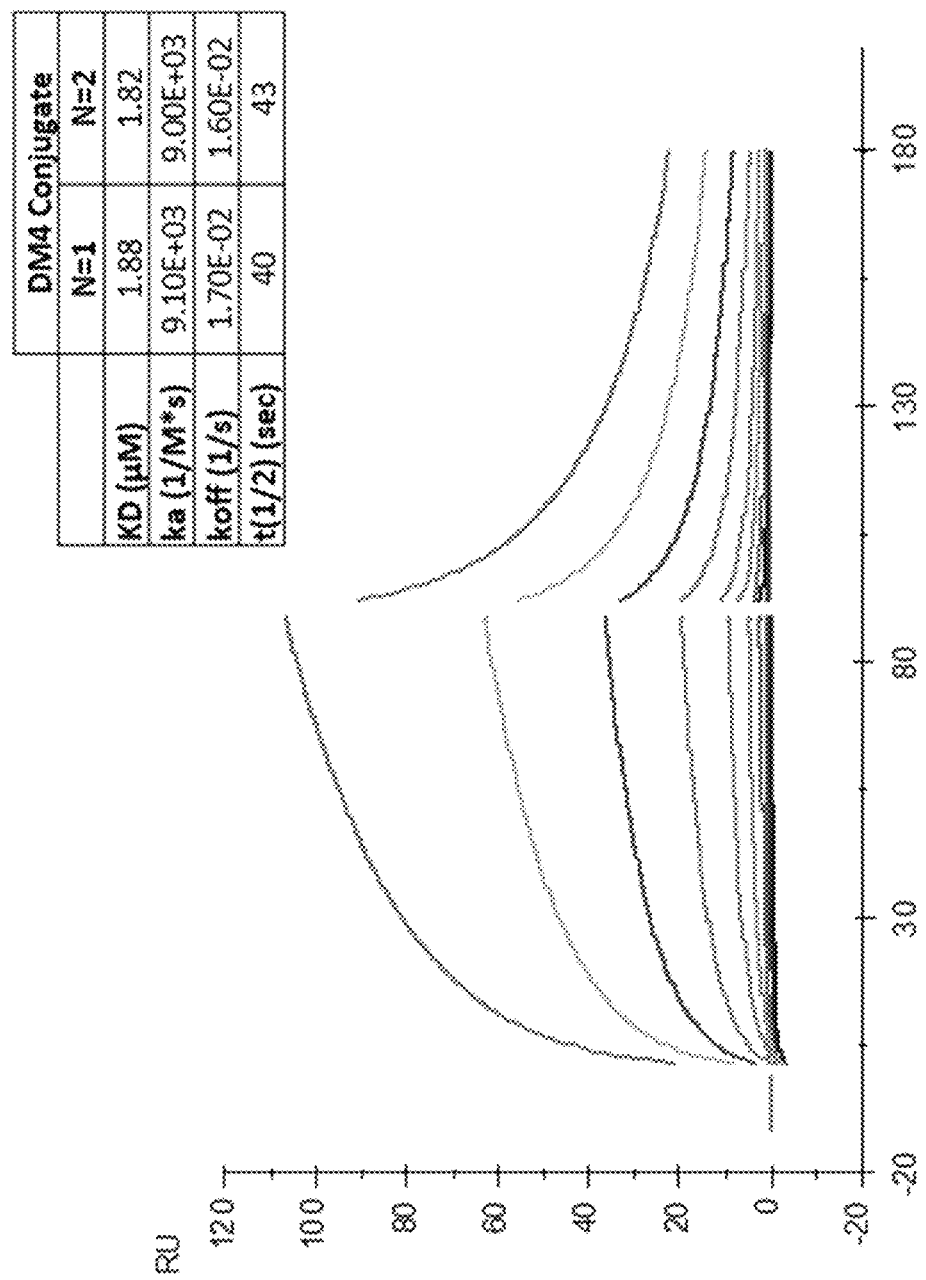
FIG. 2 depicts the kinetic analysis of Compound 5 binding to β-tubulin in vitro as determined by Biacore surface plasmon resonance.

FIG. 2 depicts the kinetic analysis of Compound 5 binding to β-tubulin in vitro as determined by Biacore surface plasmon resonance. Compound 5 is able to bind to β-tubulin with a similar KD as free DM4 (3.55 µM) and slower on/off rates relative to free DM4.

Example D: Efficacy of Compound 5 in a Mouse Colorectal Cancer Model

Six-week-old female athymic nude Foxn$^{nu}$ mice were obtained from Taconic Labs (Cat #NCRNU-F) and were housed 5 per cage on Alpha-Dri bedding in a disposable caging system. Human HCT116 cells derived from colorectal carcinoma were diluted 1:1 in Phenol Red-free Matrigel and subcutaneously implanted into the left flank of each mouse at a density of 2.5×10$^6$ cells in 100 µL. When xenografts reached a mean volume of 100-200 mm$^3$, mice were randomized into groups and treated as detailed in the table below. Mice were administered intraperitoneal (IP) doses of vehicle or 0.21, 0.29, 0.35, 0.42 µmole/kg Compound 5 (equivalent to 1.1, 1.4, 1.7, or 2 mg/kg Compound 5) or 0.42 µmole/kg unconjugated DM4 (equivalent to 0.33 mg/kg unconjugated DM4). Doses were prepared by diluting 0.1 mg/µL DMSO stocks in 5% mannitol in citrate buffer and were administered QDX4 with a two day interval between the second and third doses, at a volume of 12 mL/kg (300 µL per 25 g mouse). Xenograft tumors were measured by calipers and volume was calculated using the equation for ellipsoid volume: Volume=π/6×(length)×(width)$^2$. Body weight of animals was measured at the same time as tumor volume assessment. Animals were removed from the study due to death, tumor size exceeding 2000 mm$^3$ or loss of >20% body weight. Kaplan-Meier analysis was used to evaluate survival rate based on death or removal from study.

Figure 3A:
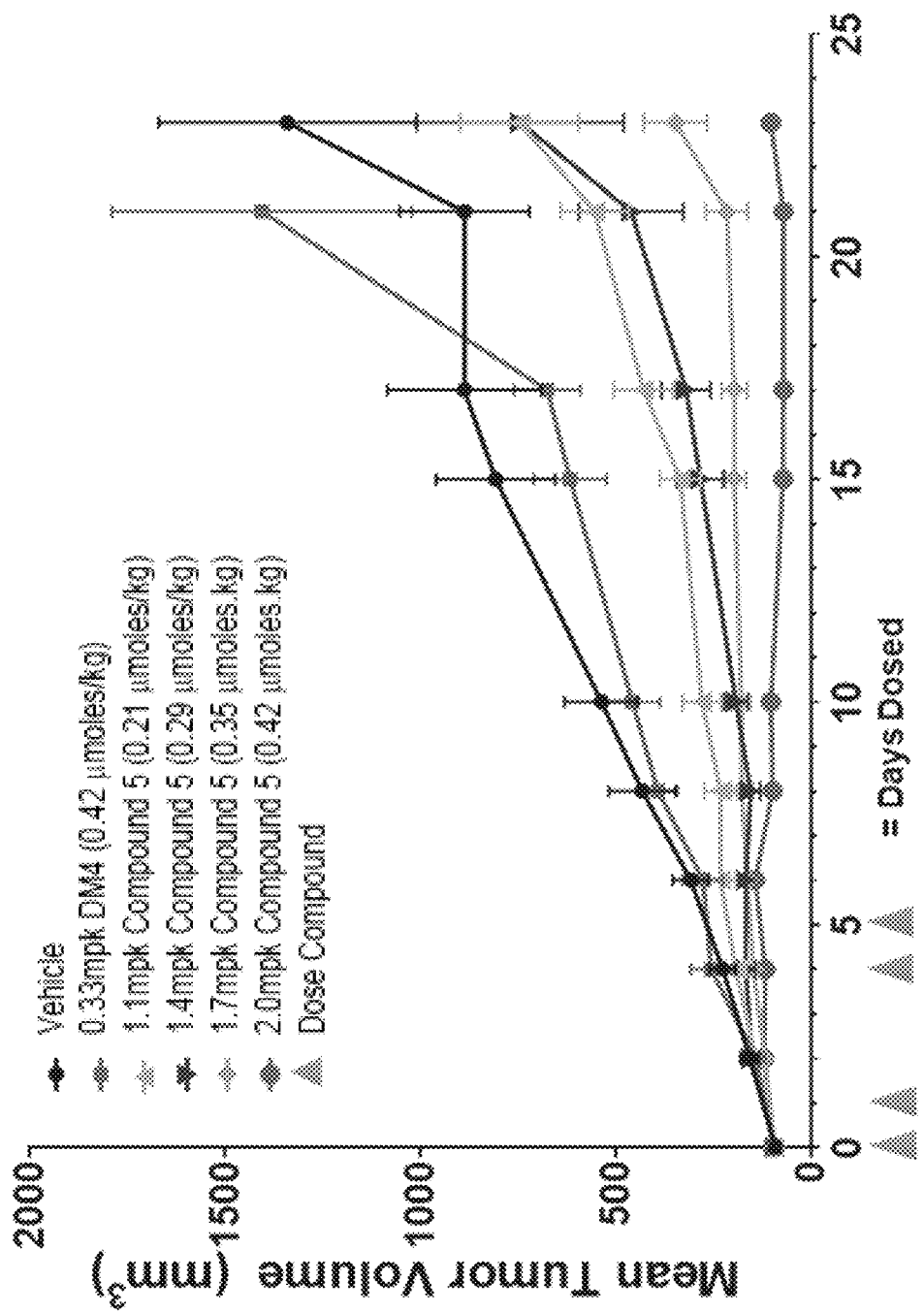
FIG. 3A shows a plot of the mean tumor volume in nude mice bearing HCT116 colorectal flank tumors dosed with DM4 or Compound 5.

FIG. 3A shows a plot of the mean tumor volume in nude mice bearing HCT116 colorectal flank tumors dosed with DM4 or Compound 5.

Figure 3B:
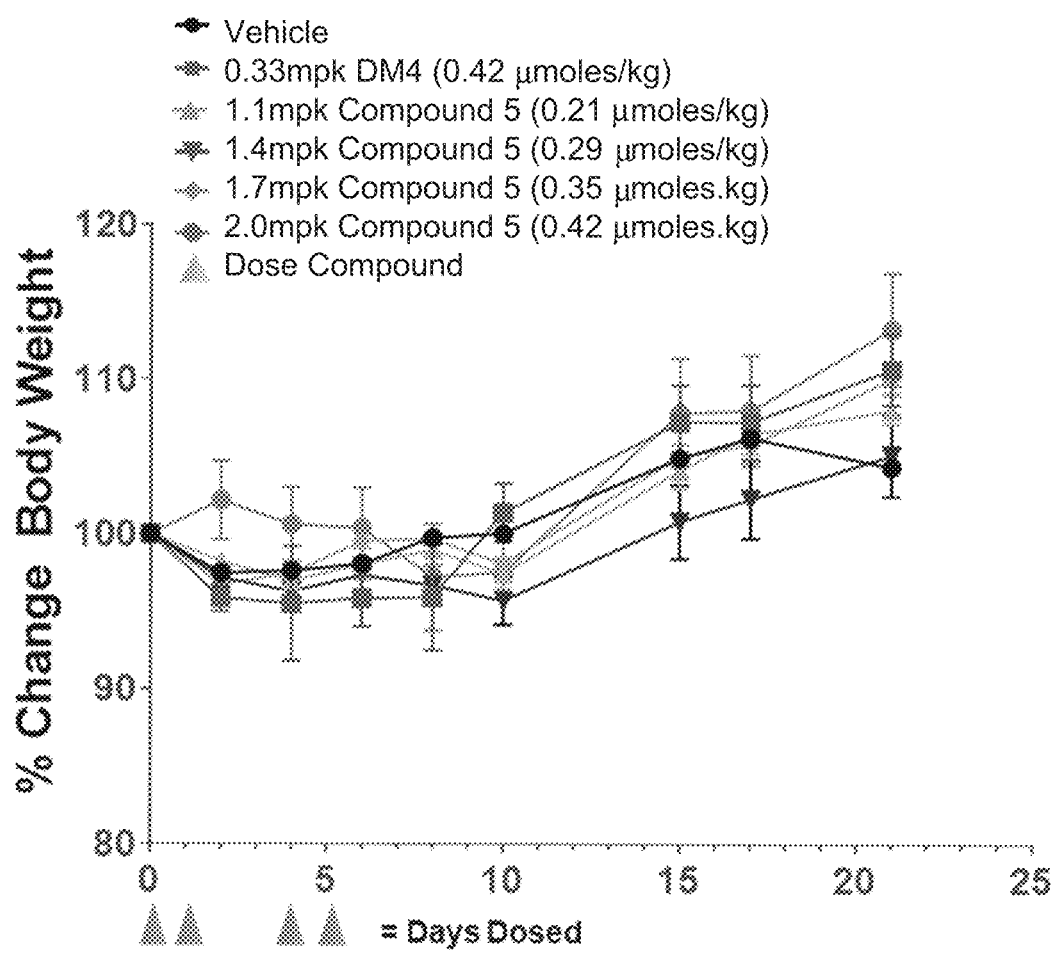
FIG. 3B shows the percent change in body weight of nude mice bearing HCT116 colorectal flank tumors dosed with DM4 or Compound 5 relative to day 0.

FIG. 3B shows the percent change in body weight of nude mice bearing HCT116 colorectal flank tumors dosed with DM4 or Compound 5 relative to day 0.

Figure 4:
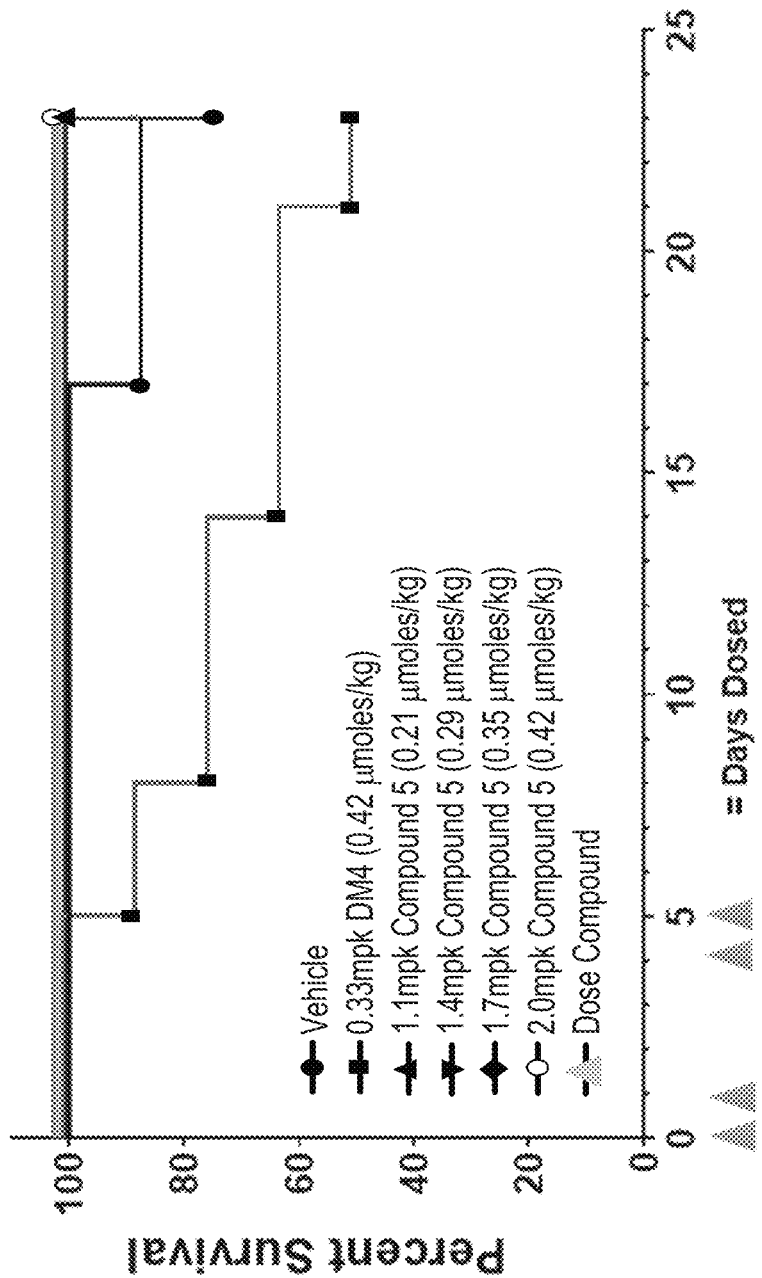
FIG. 4 depicts a Kaplan-Meier plot of nude mice bearing HCT116 colorectal flank tumors dosed with DM4 or Compound 5.

FIG. 4 depicts a Kaplan-Meier plot of nude mice bearing HCT116 colorectal flank tumors dosed with DM4 or Compound 5. Animals were removed from the study due to either death, tumor size exceeding 2000 mm$^3$ or due to loss of greater than 20% body weight. Free DM4 induced the spontaneous death of half of the DM4 group of animals during the post-dosing period. As shown in FIG. 4, Compound 5 safely delivers amounts of DM4 in vivo that otherwise result in systemic toxicity and death when dosed as free DM4.

Example E: Effect of Compound 6 on Lung Metastases in a Mouse Lung Cancer Model

Mouse 4T1-iRFP cancer cells derived from mouse mammary carcinoma and transfected with near infrared fluorescent protein (iRFP) were cultured as a monolayer at 37° C. in a humidified atmosphere with 5% CO$_2$. Cells were passaged between one and three days prior to implantation and media was replaced every 2-3 days as needed to maintain cell viability. Cells were not allowed to exceed 80% confluency. On the day of implantation, cells were trypsinized, washed with complete media and pelleted by centrifugation at 1200 rpm for 5 minutes. The supernatant was decanted, and cells were washed three times with sterile PBS and pelleted by centrifugation. During the final centrifugation, viability was determined using trypan blue exclusion. Cells were resuspended in sterile PBS a final concentration of 5×10$^5$ cells/100 µL. Cells were drawn into sterile 1 cc tuberculin syringes with a 27-gauge needle. Air bubbles were removed, and excess cell mixture was expelled back into the conical tube leaving an injection volume of 100 µL in each syringe. The 100 µL of cells were injected directly into the medial tail vein of six-week-old female athymic nude Foxn$^{nu}$ mice (Taconic Labs Cat #NCRNU-F).

Three days after cell injection, mice were administered intraperitoneal doses of vehicle or 2.5 mg/kg Compound 6 once daily for 2 days followed by 2 days of no treatment, followed by a single dose of Compound 6, for a total of three total doses of Compound 6. Eleven days after injection, mice were euthanized, and the lungs were removed for imaging using the LI-COR PEARL Trilogy small animal imager to visualize and quantitate lung metastasis and evaluate compound effect on tumor growth.

Figure 5A:
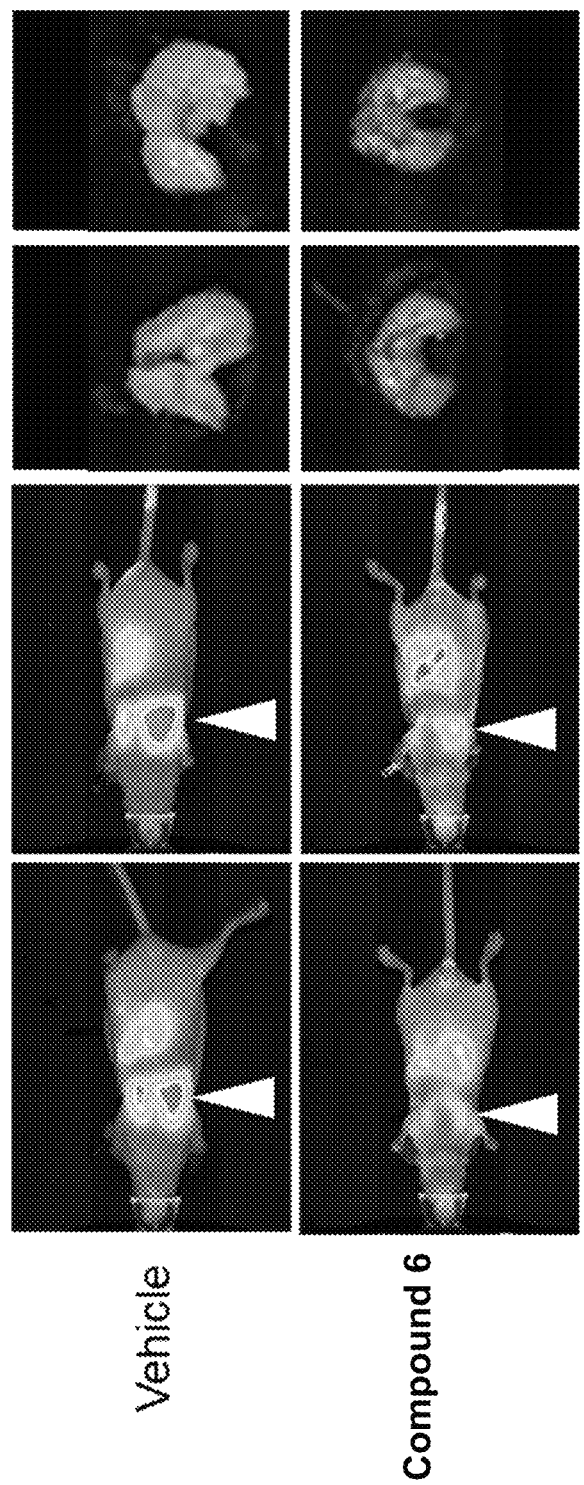
FIG. 5A depicts the ventral view and extracted lungs of nude mice inoculated with 4T1-RFP fluorescent cells via tail vein injection and imaged 11 days after inoculation and after 3 doses of vehicle or Compound 6.

FIG. 5A depicts the ventral view and extracted lungs of nude mice inoculated with 4T1-RFP fluorescent cells via tail vein injection and imaged 11 days after inoculation and after 3 doses of vehicle or Compound 6.

Figure 5B:
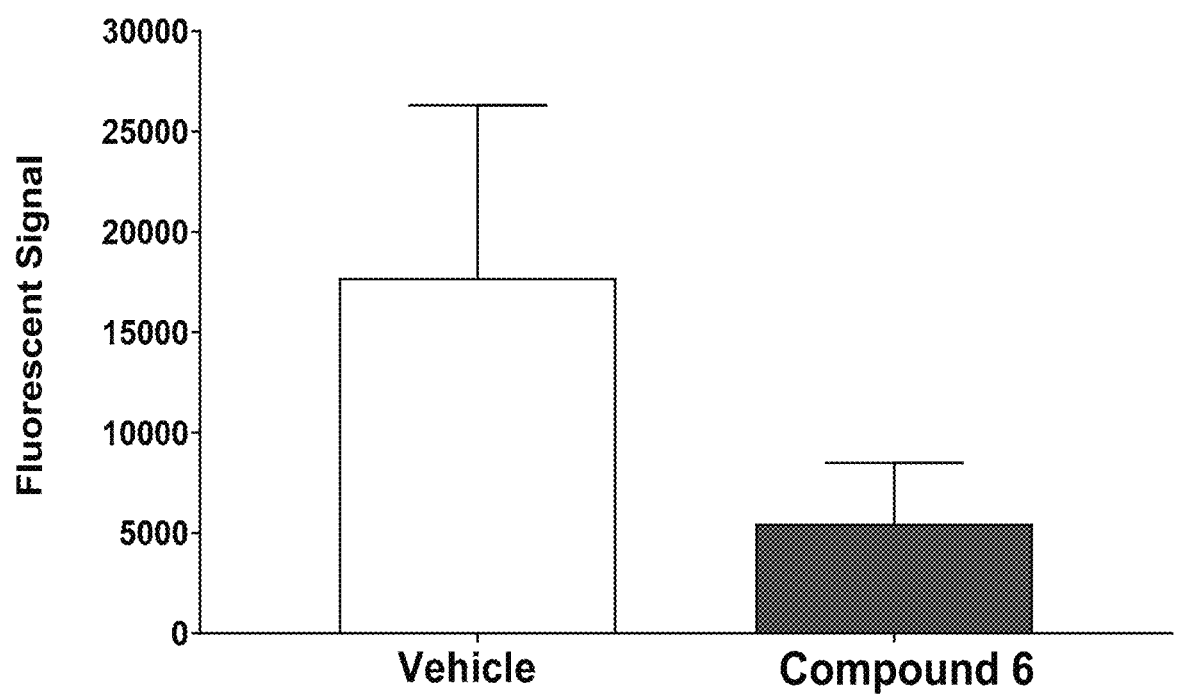
FIG. 5B depicts a graph of the fluorescent signal from extracted lungs of 4T1-RFP inoculated mice after 3 doses of vehicle or Compound 6.

FIG. 5B depicts a graph of the fluorescent signal from extracted lungs of 4T1-RFP inoculated mice after 3 doses of vehicle or Compound 6.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of treating cancer in a patient in need thereof comprising administering to the patient a therapeutically effective amount of a compound of Formula (I):

R²-L-R¹ (I)

or a pharmaceutically acceptable salt thereof, wherein:

R¹ is a peptide capable of selectively delivering R²L- across a cell membrane having an acidic or hypoxic mantle;

R² is selected from the group consisting of:

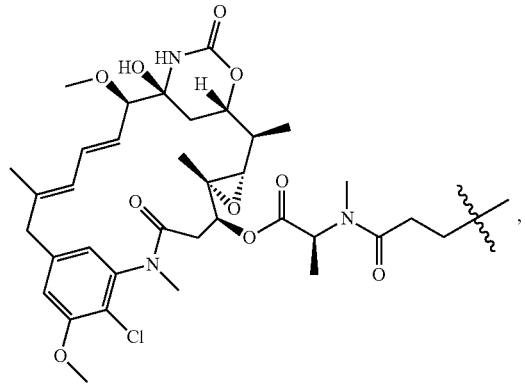

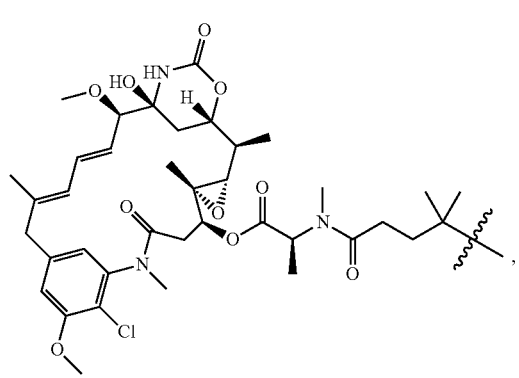

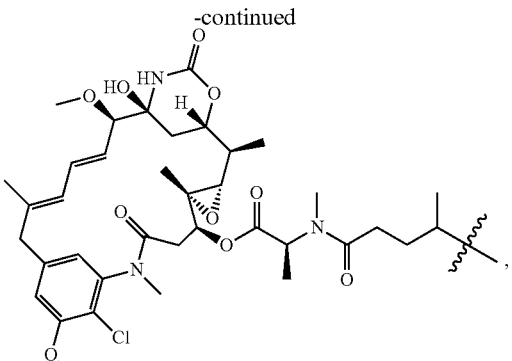

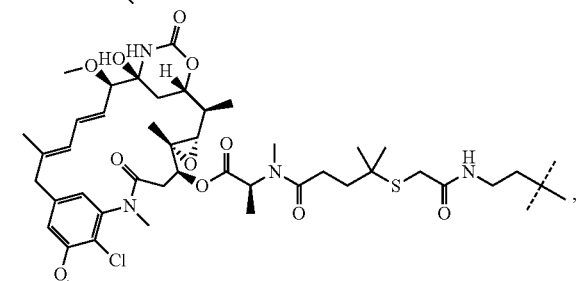

and

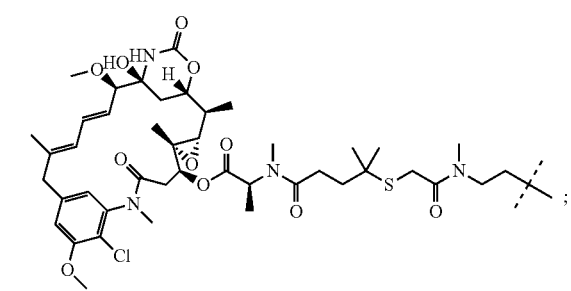

L is the following group:

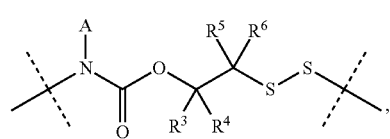

wherein

R³, R⁴, R⁵, and R⁶ are each independently selected from H, $C_{1-4}$ alkyl, $C_{1-4}$ alkenyl, $C_{6-10}$ aryl, $C_{3-10}$ cycloalkyl, 5-10 membered heteroaryl, 4-10 membered heterocycloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl, $C_{1-4}$ alkenyl, $C_{6-10}$ aryl, and 5-10 membered heteroaryl are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{e1}C(O)OR^{a1}$, and $NR^{c1}C(O)NR^{c1}R^{d1}$;

or R³ and R⁴ together with the carbon atom to which they are attached form a $C_{3-14}$ cycloalkyl group or 4-14 membered heterocycloalkyl group, each optionally substituted with 1,2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{e1}C(O)R^{b1}$, $NR^{c1}C(O)OR^{a1}$, and $NR^{c1}C(O)NR^{c1}R^{d1}$;

or R³ and R⁵ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$ $NR^{e1}C(O)R^{b1}$, $NR^{c1}C(O)OR^{a1}$, and $NR^{c1}C(O)NR^{c1}R^{d1}$;

or R⁴ and R⁶ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{e1}C(O)R^{b1}$, $NR^{c1}C(O)OR^{a1}$, and $NR^{c1}C(O)NR^{c1}R^{d1}$;

or R⁵ and R⁶ together with the carbon atom to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$ $NR^{e1}C(O)R^{b1}$, $NR^{c1}C(O)OR^{a1}$, and $NR^{c1}C(O)NR^{c1}R^{d1}$;

A is H or $C_{1-4}$ alkyl; and $R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH$.

2. The method of claim 1, wherein the cancer is selected from bladder cancer, bone cancer, glioma, breast cancer, cervical cancer, colon cancer, colorectal cancer, endometrial cancer, epithelial cancer, esophageal cancer, Ewing's sarcoma, pancreatic cancer, gallbladder cancer, gastric cancer, gastrointestinal tumors, head and neck cancer, intestinal cancers, Kaposi's sarcoma, kidney cancer, laryngeal cancer, liver cancer, lung cancer, melanoma, prostate cancer, rectal cancer, renal clear cell carcinoma, skin cancer, stomach cancer, testicular cancer, thyroid cancer, and uterine cancer.

3. The method of claim 1, wherein the cancer is selected from lung cancer, colorectal cancer, and gastric cancer.

4. The method of claim 1, wherein $R^1$ is a peptide capable of selectively delivering $R^2$L-across a cell membrane having an acidic or hypoxic mantle having a pH less than about 6.0.

5. The method of claim 1, wherein $R^1$ is a peptide comprising at least one of the following sequences:

```
                                    (SEQ ID NO. 1; Pv1)
ADDQNPWRAYLDLLFPTDTLLLDLLWCG, (SEQ ID NO. 2; Pv2)
AEQNPIYWARYADWLFTTPLLLLDLALLVDADECG,
and (SEQ ID NO. 3; Pv3)
ADDQNPWRAYLDLLFPTDTLLLDLLWDADECG;
and (SEQ ID No. 6; Pv6)
AAEQNPIYWWARYADWLFTTPLLLLDLALLVDADEGTCG;
``` wherein $R^1$ is attached to L through a cysteine residue of $R^1$.

6. The method of claim 1, wherein $R^1$ is a peptide comprising at least the following sequence:

```
                                    (SEQ ID NO. 1; Pv1)
ADDQNPWRAYLDLLFPTDTLLLDLLWCG.
```

7. The method of claim 1, wherein $R^1$ is a peptide comprising at least the following sequence:

```
                                    (SEQ ID NO. 2; Pv2)
AEQNPIYWARYADWLFTTPLLLLDLALLVDADECG.
```

8. The method of claim 1, wherein $R^1$ is a peptide comprising at least the following sequence:

```
                                    (SEQ ID NO. 3; Pv3)
ADDQNPWRAYLDLLFPTDTLLLDLLWDADECG.
```

9. The method of claim 1, wherein $R^1$ is a peptide comprising at least the following sequence:

```
                                    (SEQ ID NO. 6; Pv6)
AAEQNPIYWWARYADWLFTTPLLLLDLALLVDADEGTCG.
```

10. The method of claim 1, wherein $R^2$ is:

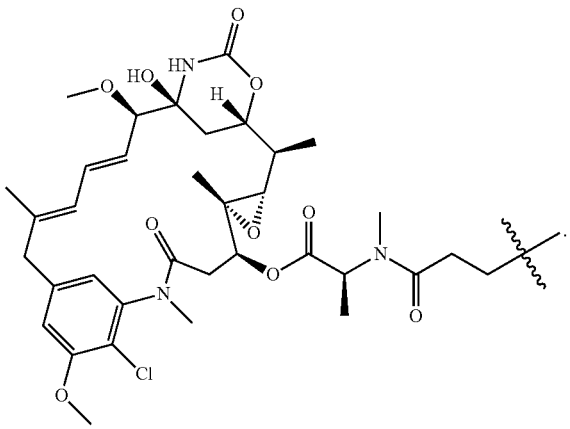

11. The method of claim 1, wherein $R^2$ is:

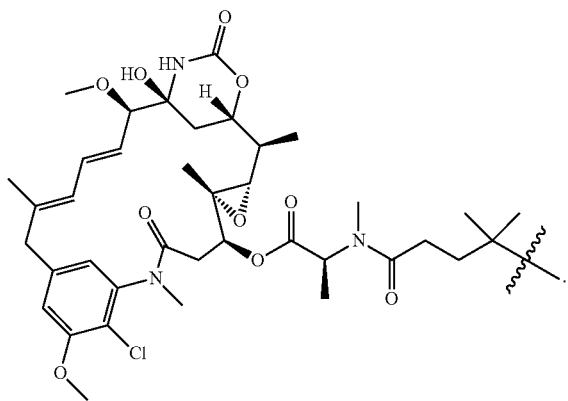

12. The method of claim 1, wherein $R^2$ is:

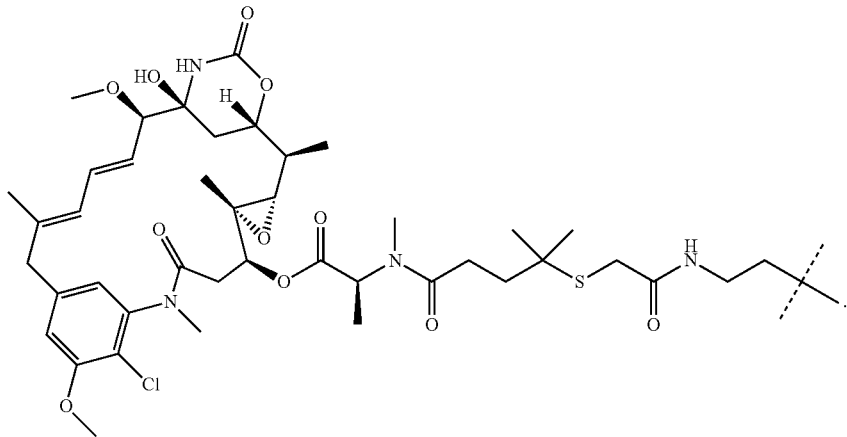

13. The method of claim 1, wherein $R^2$ is:

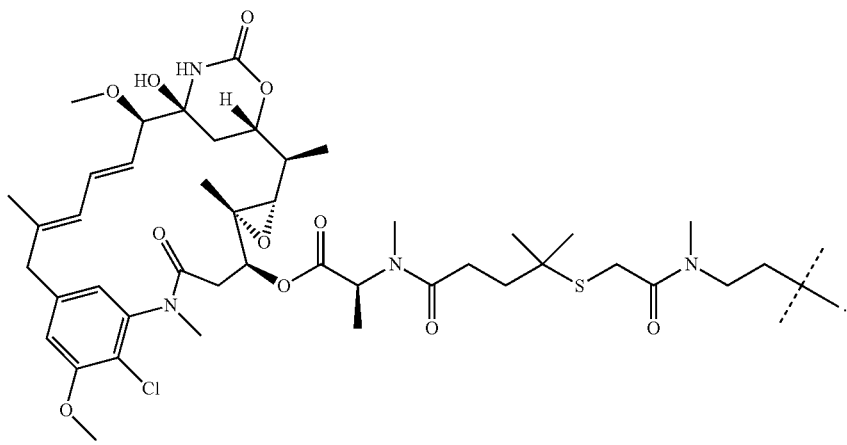

14. The method of claim 1, wherein L is:

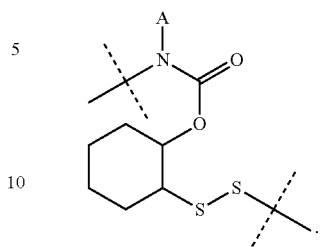

15. The method of claim 1, wherein $R^3$, $R^4$, $R^5$, and $R^6$ are each independently selected from H and $C_{1-4}$ alkyl.

16. The method of claim 1, wherein $R^3$, $R^4$, $R^5$, and $R^6$ are each H.

17. The method of claim 1, wherein A is H.

18. The method of claim 1, wherein A is $CH_3$.

19. The method of claim 1, wherein the compound is selected from:

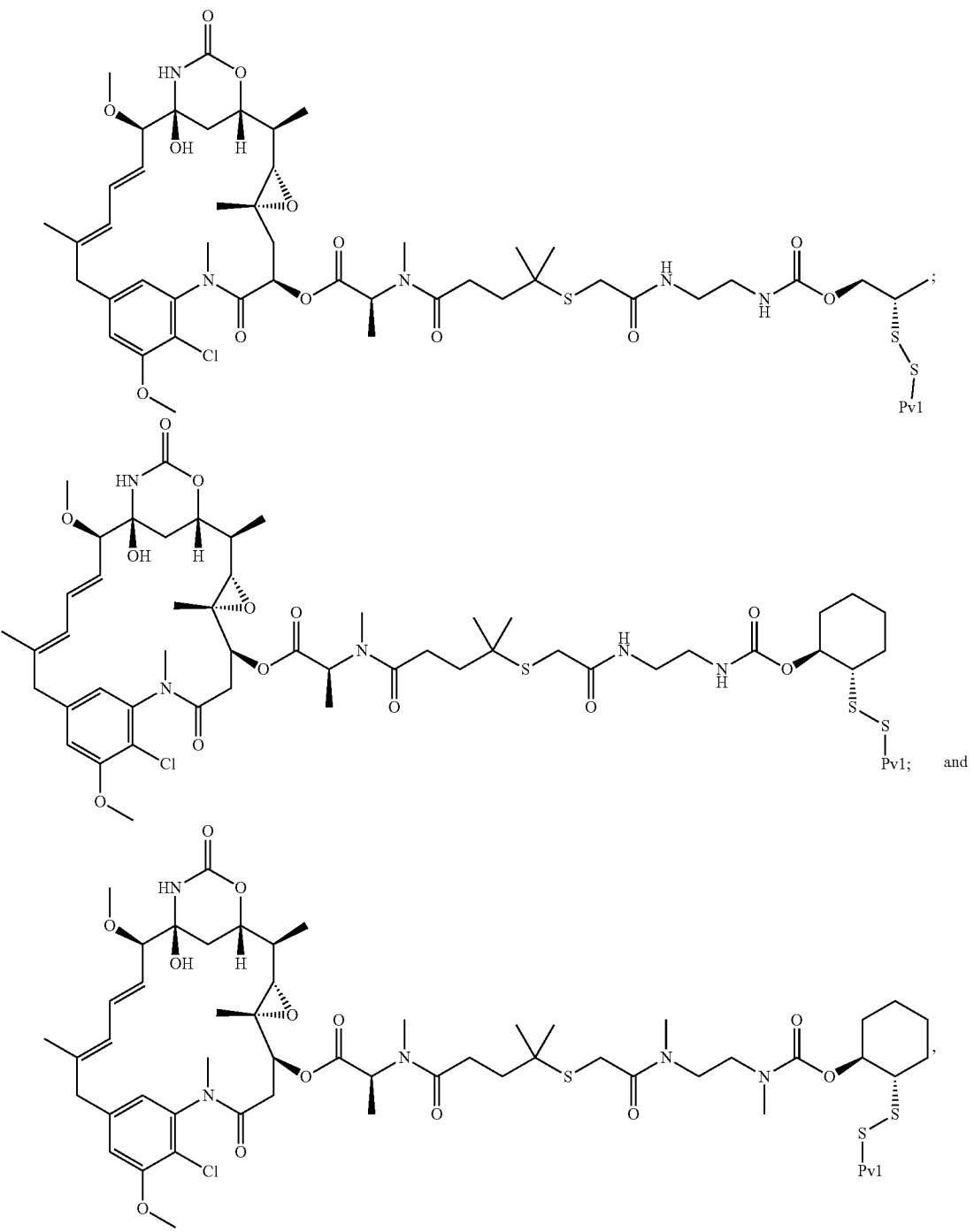
or a pharmaceutically acceptable salt of any of the aforementioned,
wherein Pv1 is a peptide comprising at least the following sequence:
(SEQ ID NO. 1)
ADDQNPWRAYLDLLFPTDTLLLDLLWCG.

20. The method of claim 1, wherein the compound is:

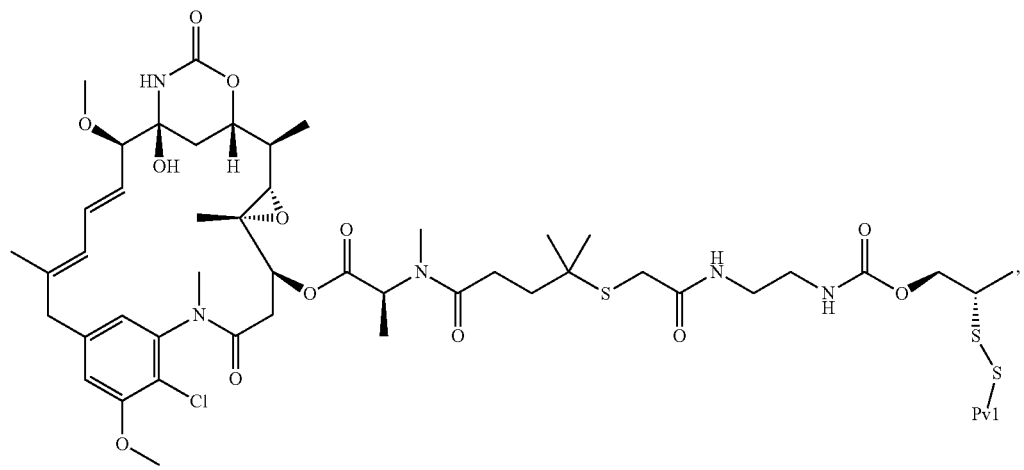

or a pharmaceutically acceptable salt thereof, wherein Pv1 is a peptide comprising at least the following sequence:

ADDQNPWRAYLDLLFPTDTLLLDLLWCG. (SEQ ID NO. 1)

21. The method of claim 1, wherein the compound is:

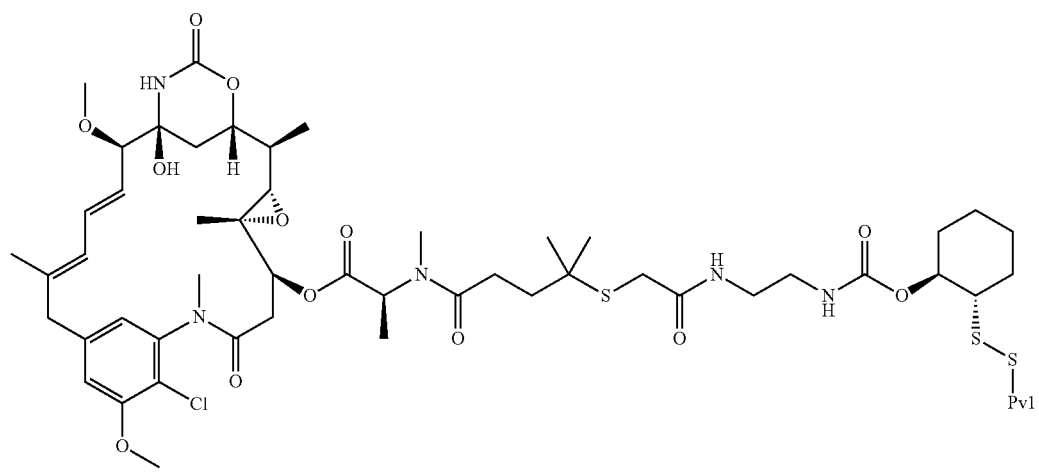

or a pharmaceutically acceptable salt thereof, wherein Pv1 is a peptide comprising at least the following sequence:

ADDQNPWRAYLDLLFPTDTLLLDLLWCG. (SEQ ID NO. 1)

22. The method of claim 1, wherein the compound is:
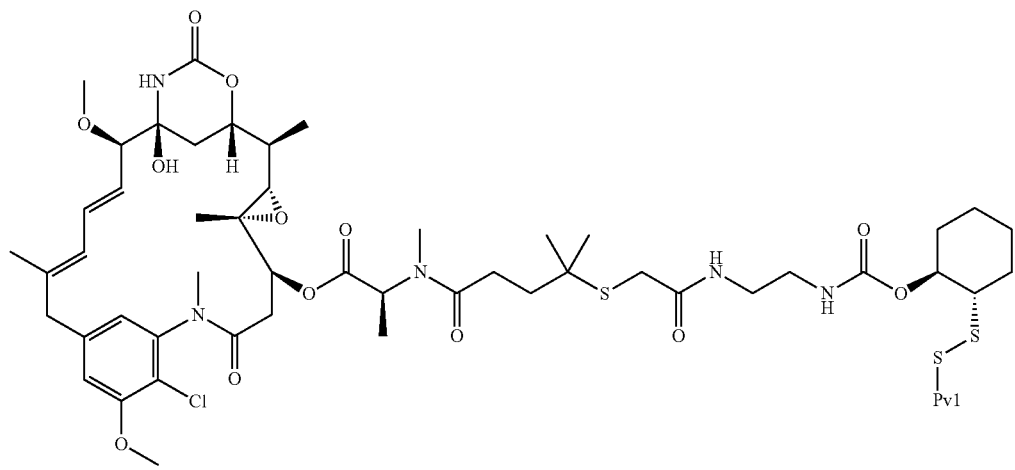
or a pharmaceutically acceptable salt thereof, wherein Pv1 is a peptide comprising at least the following sequence:
```
                                    (SEQ ID NO. 1)
ADDQNPWRAYLDLLFPTDTLLLDLLWCG.
```
\* \* \* \* \*

```
                            SEQUENCE LISTING

Sequence total quantity: 311
SEQ ID NO: 1            moltype = AA  length = 28
FEATURE                 Location/Qualifiers
REGION                  1..28
                        note = synthetic peptide
source                  1..28
                        mol_type = protein
                        organism = synthetic construct
SEQUENCE: 1
ADDQNPWRAY LDLLFPTDTL LLDLLWCG                                           28

SEQ ID NO: 2            moltype = AA  length = 35
FEATURE                 Location/Qualifiers
REGION                  1..35
                        note = synthetic peptide
source                  1..35
                        mol_type = protein
                        organism = synthetic construct
SEQUENCE: 2
AEQNPIYWAR YADWLFTTPL LLLDLALLVD ADECG                                   35

SEQ ID NO: 3            moltype = AA  length = 32
FEATURE                 Location/Qualifiers
REGION                  1..32
                        note = synthetic peptide
source                  1..32
                        mol_type = protein
                        organism = synthetic construct
SEQUENCE: 3
ADDQNPWRAY LDLLFPTDTL LLDLLWDADE CG                                      32

SEQ ID NO: 4            moltype = AA  length = 39
FEATURE                 Location/Qualifiers
REGION                  1..39
                        note = synthetic peptide
SITE                    1
                        note = MISC_FEATURE - acetylated
source                  1..39
                        mol_type = protein
                        organism = synthetic construct
SEQUENCE: 4
AAEQNPIYWA RYADWLFTTP LLLLDLALLV DADEGTKCG                               39

SEQ ID NO: 5            moltype = AA  length = 37
FEATURE                 Location/Qualifiers
REGION                  1..37
                        note = synthetic peptide
source                  1..37
                        mol_type = protein
                        organism = synthetic construct
SEQUENCE: 5
AAEQNPIYWA RYADWLFTTP LLLLDLALLV DADEGTC                                 37

SEQ ID NO: 6            moltype = AA  length = 39
FEATURE                 Location/Qualifiers
REGION                  1..39
                        note = Description of Unknown: pH-sensitive membrane
                         polypeptide
source                  1..39
                        mol_type = protein
                        organism = unidentified
SEQUENCE: 6
AAEQNPIYWW ARYADWLFTT PLLLLDLALL VDADEGTCG                               39

SEQ ID NO: 7            moltype = AA  length = 35
FEATURE                 Location/Qualifiers
REGION                  1..35
                        note = Description of Unknown: Wild-type pH-sensitive
                          membrane polypeptide
```

```
source                  1..35
                        mol_type = protein
                        organism = unidentified
SEQUENCE: 7
AEQNPIYWAR YADWLFTTPL LLLDLALLVD ADEGT                                    35

SEQ ID NO: 8            moltype = AA  length = 36
FEATURE                 Location/Qualifiers
REGION                  1..36
                        note = Description of Unknown: Wild-type pH-sensitive
                         membrane polypeptide
source                  1..36
                        mol_type = protein
                        organism = unidentified
SEQUENCE: 8
GGEQNPIYWA RYADWLFTTP LLLLDLALLV DADEGT                                   36

SEQ ID NO: 9            moltype = AA  length = 35
FEATURE                 Location/Qualifiers
REGION                  1..35
                        note = Description of Unknown: Wild-type pH-sensitive
                         membrane polypeptide
source                  1..35
                        mol_type = protein
                        organism = unidentified
SEQUENCE: 9
AEQNPIYWAR YADWLFTTPL LLLDLALLVD ADEGT                                    35

SEQ ID NO: 10           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 10
AAEQNPIYWA RYADWLFTTP LLLLDLALLV DADEGTCG                                 38

SEQ ID NO: 11           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 11
GGEQNPIYWA RYADWLFTTP LLLLDLALLV DADEGTCG                                 38

SEQ ID NO: 12           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 12
ACEQNPIYWA RYADWLFTTP LLLLDLALLV DADEGTG                                  37

SEQ ID NO: 13           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 13
ACEQNPIYWA RYADWLFTTP LLLLDLALLV DADEGT                                   36

SEQ ID NO: 14           moltype = AA  length = 36
FEATURE                 Location/Qualifiers
REGION                  1..36
                        note = Description of Artificial Sequence: Synthetic
                         polypeptide
source                  1..36
                        mol_type = protein
```

```
                        organism = synthetic construct
SEQUENCE: 14
AKEQNPIYWA RYADWLFTTP LLLLDLALLV DADEGT                                  36

SEQ ID NO: 15           moltype = AA  length = 39
FEATURE                 Location/Qualifiers
REGION                  1..39
                        note = Description of Artificial Sequence: Synthetic
                        polypeptide
source                  1..39
                        mol_type = protein
                        organism = synthetic construct
SEQUENCE: 15
AAEQNPIYWA RYADWLFTTP LLLLDLALLV DADEGTKCG                               39

SEQ ID NO: 16           moltype = AA  length = 36
FEATURE                 Location/Qualifiers
REGION                  1..36
                        note = Description of Artificial Sequence: Synthetic
                        polypeptide
source                  1..36
                        mol_type = protein
                        organism = synthetic construct
SEQUENCE: 16
AKEQNPIYWA RYADWLFTTP LLLLDLALLV DADECT                                  36

SEQ ID NO: 17           moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 17
ACEQNPIYWA RYANWLFTTP LLLLNLALLV DADEGTG                                 37

SEQ ID NO: 18           moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 18
ACEQNPIYWA RYAKWLFTTP LLLLKLALLV DADEGTG                                 37

SEQ ID NO: 19           moltype = AA  length = 36
FEATURE                 Location/Qualifiers
REGION                  1..36
                        note = Description of Artificial Sequence: Synthetic
                        polypeptide
source                  1..36
                        mol_type = protein
                        organism = synthetic construct
SEQUENCE: 19
GGEQNPIYWA RYADWLFTTP LLLLDLALLV NANQGT                                  36

SEQ ID NO: 20           moltype = AA  length = 36
FEATURE                 Location/Qualifiers
REGION                  1..36
                        note = Description of Artificial Sequence: Synthetic
                        polypeptide
source                  1..36
                        mol_type = protein
                        organism = synthetic construct
SEQUENCE: 20
AAEQNPIYWA RYADWLFTTP LLLLALALLV DADEGT                                  36

SEQ ID NO: 21           moltype = AA  length = 36
FEATURE                 Location/Qualifiers
REGION                  1..36
                        note = Description of Artificial Sequence: Synthetic
                        polypeptide
source                  1..36
                        mol_type = protein
                        organism = synthetic construct
SEQUENCE: 21
```

```
AAEQNPIYWA RYAAWLFTTP LLLLDLALLV DADEGT                                      36

SEQ ID NO: 22           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 22
AAEQNPIYWA RYADWLFTTA LLLLDLALLV DADEGT                                      36

SEQ ID NO: 23           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 23
AAEQNPIYWA RYADWLFTTP LLLLELALLV DADEGT                                      36

SEQ ID NO: 24           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 24
AAEQNPIYWA RYAEWLFTTP LLLLDLALLV DADEGT                                      36

SEQ ID NO: 25           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 25
AAEQNPIIYW ARYADWLFTD LPLLLLDLLA LLVDADEGT                                   39

SEQ ID NO: 26           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 26
GEQNPIYWAQ YADWLFTTPL LLLDLALLVD ADEGTCG                                     37

SEQ ID NO: 27           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 27
GGEQNPIYWA RYADWLFTTP LLLDLLALLV DADEGTCG                                    38

SEQ ID NO: 28           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 28
GGEQNPIYWA RYADWLFTTP LLLLLDALLV DADEGTCG                                    38
```

```
SEQ ID NO: 29              moltype = AA  length = 38
FEATURE                    Location/Qualifiers
REGION                     1..38
                           note = Description of Artificial Sequence: Synthetic
                            polypeptide
source                     1..38
                           mol_type = protein
                           organism = synthetic construct
SEQUENCE: 29
GGEQNPIYWA RYDAWLFTTP LLLLDLALLV DADEGTCG                           38

SEQ ID NO: 30              moltype = AA  length = 38
FEATURE                    Location/Qualifiers
REGION                     1..38
                           note = Description of Artificial Sequence: Synthetic
                            polypeptide
source                     1..38
                           mol_type = protein
                           organism = synthetic construct
SEQUENCE: 30
GGEQNPIYWA RYAWDLFTTP LLLLDLALLV DADEGTCG                           38

SEQ ID NO: 31              moltype = AA  length = 36
FEATURE                    Location/Qualifiers
REGION                     1..36
                           note = Description of Artificial Sequence: Synthetic
                            polypeptide
source                     1..36
                           mol_type = protein
                           organism = synthetic construct
SEQUENCE: 31
AAEQNPIYWA RYADWLFTTG LLLLDLALLV DADEGT                             36

SEQ ID NO: 32              moltype = AA  length = 37
FEATURE                    Location/Qualifiers
REGION                     1..37
                           note = Description of Artificial Sequence: Synthetic
                            polypeptide
source                     1..37
                           mol_type = protein
                           organism = synthetic construct
SEQUENCE: 32
DDDEDNPIYW ARYADWLFTT PLLLLHGALL VDADECT                            37

SEQ ID NO: 33              moltype = AA  length = 38
FEATURE                    Location/Qualifiers
REGION                     1..38
                           note = Description of Artificial Sequence: Synthetic
                            polypeptide
source                     1..38
                           mol_type = protein
                           organism = synthetic construct
SEQUENCE: 33
DDDEDNPIYW ARYAHWLFTT PLLLLHGALL VDADEGCT                           38

SEQ ID NO: 34              moltype = AA  length = 37
FEATURE                    Location/Qualifiers
REGION                     1..37
                           note = Description of Artificial Sequence: Synthetic
                            polypeptide
source                     1..37
                           mol_type = protein
                           organism = synthetic construct
SEQUENCE: 34
DDDEDNPIYW ARYAHWLFTT PLLLLHGALL VNADECT                            37

SEQ ID NO: 35              moltype = AA  length = 37
FEATURE                    Location/Qualifiers
REGION                     1..37
                           note = Description of Artificial Sequence: Synthetic
                            polypeptide
source                     1..37
                           mol_type = protein
                           organism = synthetic construct
SEQUENCE: 35
DDDEDNPIYW ARYAHWLFTT PLLLLHGALL VNANECT                            37

SEQ ID NO: 36              moltype = AA  length = 34
FEATURE                    Location/Qualifiers
```

```
REGION                        1..34
                              note = Description of Artificial Sequence: Synthetic
                               polypeptide
source                        1..34
                              mol_type = protein
                              organism = synthetic construct
SEQUENCE: 36
AEQNPIYWAR YADFLFTTPL LLLDLALLVD ADET                                          34

SEQ ID NO: 37                 moltype = AA  length = 35
FEATURE                       Location/Qualifiers
REGION                        1..35
                              note = Description of Artificial Sequence: Synthetic
                               polypeptide
source                        1..35
                              mol_type = protein
                              organism = synthetic construct
SEQUENCE: 37
AEQNPIYFAR YADWLFTTPL LLLDLALLVD ADEGT                                         35

SEQ ID NO: 38                 moltype = AA  length = 34
FEATURE                       Location/Qualifiers
REGION                        1..34
                              note = Description of Artificial Sequence: Synthetic
                               polypeptide
source                        1..34
                              mol_type = protein
                              organism = synthetic construct
SEQUENCE: 38
AEQNPIYFAR YADFLFTTPL LLLDLALLWD ADET                                          34

SEQ ID NO: 39                 moltype = AA  length = 32
FEATURE                       Location/Qualifiers
REGION                        1..32
                              note = Description of Artificial Sequence: Synthetic
                               polypeptide
source                        1..32
                              mol_type = protein
                              organism = synthetic construct
SEQUENCE: 39
AKEDQNPYWA RYADWLFTTP LLLLDLALLV DG                                            32

SEQ ID NO: 40                 moltype = AA  length = 32
FEATURE                       Location/Qualifiers
REGION                        1..32
                              note = Description of Artificial Sequence: Synthetic
                               polypeptide
source                        1..32
                              mol_type = protein
                              organism = synthetic construct
SEQUENCE: 40
ACEDQNPYWA RYADWLFTTP LLLLDLALLV DG                                            32

SEQ ID NO: 41                 moltype = AA  length = 32
FEATURE                       Location/Qualifiers
REGION                        1..32
                              note = Description of Artificial Sequence: Synthetic
                               polypeptide
source                        1..32
                              mol_type = protein
                              organism = synthetic construct
SEQUENCE: 41
AEDQNPYWAR YADWLFTTPL LLLDLALLVD CG                                            32

SEQ ID NO: 42                 moltype = AA  length = 32
FEATURE                       Location/Qualifiers
REGION                        1..32
                              note = Description of Artificial Sequence: Synthetic
                               polypeptide
source                        1..32
                              mol_type = protein
                              organism = synthetic construct
SEQUENCE: 42
AEDQNPYWAR YADWLFTTPL LLLELALLVE CG                                            32

SEQ ID NO: 43                 moltype = AA  length = 30
FEATURE                       Location/Qualifiers
REGION                        1..30
                              note = Description of Artificial Sequence: Synthetic
```

```
                            polypeptide
source                      1..30
                            mol_type = protein
                            organism = synthetic construct
SEQUENCE: 43
AKEDQNPYWR AYADLFTPLT LLDLLALWDG                                              30

SEQ ID NO: 44               moltype = AA  length = 30
FEATURE                     Location/Qualifiers
REGION                      1..30
                            note = Description of Artificial Sequence: Synthetic
                             polypeptide
source                      1..30
                            mol_type = protein
                            organism = synthetic construct
SEQUENCE: 44
ACEDQNPYWR AYADLFTPLT LLDLLALWDG                                              30

SEQ ID NO: 45               moltype = AA  length = 27
FEATURE                     Location/Qualifiers
REGION                      1..27
                            note = Description of Artificial Sequence: Synthetic peptide
source                      1..27
                            mol_type = protein
                            organism = synthetic construct
SEQUENCE: 45
ACDDQNPWRA YLDLLFPTDT LLLDLLW                                                 27

SEQ ID NO: 46               moltype = AA  length = 34
FEATURE                     Location/Qualifiers
REGION                      1..34
                            note = Description of Artificial Sequence: Synthetic
                             polypeptide
source                      1..34
                            mol_type = protein
                            organism = synthetic construct
SEQUENCE: 46
TEDADVLLAL DLLLLPTTFL WDAYRAWYPN QECA                                         34

SEQ ID NO: 47               moltype = AA  length = 20
FEATURE                     Location/Qualifiers
REGION                      1..20
                            note = Description of Artificial Sequence: Synthetic peptide
source                      1..20
                            mol_type = protein
                            organism = synthetic construct
SEQUENCE: 47
AEQNPIYWAR YADWLFTTPL                                                         20

SEQ ID NO: 48               moltype = AA  length = 21
FEATURE                     Location/Qualifiers
REGION                      1..21
                            note = Description of Artificial Sequence: Synthetic peptide
source                      1..21
                            mol_type = protein
                            organism = synthetic construct
SEQUENCE: 48
AEQNPIYWAR YADWLFTTPC L                                                       21

SEQ ID NO: 49               moltype = AA  length = 21
FEATURE                     Location/Qualifiers
REGION                      1..21
                            note = Description of Artificial Sequence: Synthetic peptide
source                      1..21
                            mol_type = protein
                            organism = synthetic construct
SEQUENCE: 49
ACEQNPIYWA RYADWLFTTP L                                                       21

SEQ ID NO: 50               moltype = AA  length = 20
FEATURE                     Location/Qualifiers
REGION                      1..20
                            note = Description of Artificial Sequence: Synthetic peptide
source                      1..20
                            mol_type = protein
                            organism = synthetic construct
SEQUENCE: 50
AEQNPIYFAR YADWLFTTPL                                                         20
```

```
SEQ ID NO: 51         moltype = AA  length = 21
FEATURE               Location/Qualifiers
REGION                1..21
                      note = Description of Artificial Sequence: Synthetic peptide
source                1..21
                      mol_type = protein
                      organism = synthetic construct
SEQUENCE: 51
KEDQNPWARY ADLLFPTTLA W                                                   21

SEQ ID NO: 52         moltype = AA  length = 22
FEATURE               Location/Qualifiers
REGION                1..22
                      note = Description of Artificial Sequence: Synthetic peptide
source                1..22
                      mol_type = protein
                      organism = synthetic construct
SEQUENCE: 52
ACEDQNPWAR YADLLFPTTL AW                                                  22

SEQ ID NO: 53         moltype = AA  length = 24
FEATURE               Location/Qualifiers
REGION                1..24
                      note = Description of Artificial Sequence: Synthetic peptide
source                1..24
                      mol_type = protein
                      organism = synthetic construct
SEQUENCE: 53
ACEDQNPWAR YADWLFPTTL LLLD                                                24

SEQ ID NO: 54         moltype = AA  length = 22
FEATURE               Location/Qualifiers
REGION                1..22
                      note = Description of Artificial Sequence: Synthetic peptide
source                1..22
                      mol_type = protein
                      organism = synthetic construct
SEQUENCE: 54
ACEEQNPWAR YAELLFPTTL AW                                                  22

SEQ ID NO: 55         moltype = AA  length = 24
FEATURE               Location/Qualifiers
REGION                1..24
                      note = Description of Artificial Sequence: Synthetic peptide
source                1..24
                      mol_type = protein
                      organism = synthetic construct
SEQUENCE: 55
ACEEQNPWAR YAEWLFPTTL LLLE                                                24

SEQ ID NO: 56         moltype = AA  length = 25
FEATURE               Location/Qualifiers
REGION                1..25
                      note = Description of Artificial Sequence: Synthetic peptide
source                1..25
                      mol_type = protein
                      organism = synthetic construct
SEQUENCE: 56
ACEEQNPWAR YLEWLFPTET LLLEL                                               25

SEQ ID NO: 57         moltype = AA  length = 36
FEATURE               Location/Qualifiers
REGION                1..36
                      note = Description of Artificial Sequence: Synthetic
                       polypeptide
source                1..36
                      mol_type = protein
                      organism = synthetic construct
SEQUENCE: 57
GGEQNPIYWA RYADWLFTTP LLLLDLALLV DADEGT                                   36

SEQ ID NO: 58         moltype = AA  length = 35
FEATURE               Location/Qualifiers
REGION                1..35
                      note = Description of Artificial Sequence: Synthetic
                       polypeptide
source                1..35
                      mol_type = protein
                      organism = synthetic construct
```

```
SEQUENCE: 58
ACEQNPIYWA RYADWLFTTP LLLLDLALLV DADET                                  35

SEQ ID NO: 59           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 59
AAEQNPIYWA RYADWLFTTP LLLLDLALLV DADEGTCG                               38

SEQ ID NO: 60           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 60
AEQNPIYWAR YADWLFTTPL LLLDLALLVD ADEGCT                                 36

SEQ ID NO: 61           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 61
GGEQNPIYWA RYADWLFTTP LLLLDLALLV DADEGTCG                               38

SEQ ID NO: 62           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 62
ACEQNPIYWA RYADWLFTTP LLLLDLALLV DADEGT                                 36

SEQ ID NO: 63           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 63
AKEQNPIYWA RYADWLFTTP LLLLDLALLV DADEGT                                 36

SEQ ID NO: 64           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 64
AKEQNPIYWA RYADWLFTTP LLLLDLALLV DADECT                                 36

SEQ ID NO: 65           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 65
AAEQNPIYWA RYADWLFTTA LLLLDLALLV DADEGT                                 36
```

```
SEQ ID NO: 66          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 66
ACAEQNPIYW ARYADWLFTT GLLLLDLALL VDADEGT                                   37

SEQ ID NO: 67          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 67
AEQNPIYWAR YADFLFTTPL LLLDLALLVD ADET                                      34

SEQ ID NO: 68          moltype = AA  length = 35
FEATURE                Location/Qualifiers
REGION                 1..35
                       note = Description of Artificial Sequence: Synthetic
                        polypeptide
source                 1..35
                       mol_type = protein
                       organism = synthetic construct
SEQUENCE: 68
AEQNPIYFAR YADWLFTTPL LLLDLALLVD ADEGT                                     35

SEQ ID NO: 69          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 69
AEQNPIYFAR YADFLFTTPL LLLDLALLWD ADET                                      34

SEQ ID NO: 70          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 70
AKEDQNPYWA RYADWLFTTP LLLLDLALLV DG                                        32

SEQ ID NO: 71          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 71
ACEDQNPYWA RYADWLFTTP LLLLDLALLV DG                                        32

SEQ ID NO: 72          moltype = AA  length = 31
FEATURE                Location/Qualifiers
REGION                 1..31
                       note = Description of Artificial Sequence: Synthetic
                        polypeptide
source                 1..31
                       mol_type = protein
                       organism = synthetic construct
SEQUENCE: 72
AEDQNPYWAR YADWLFTTPL LLLDLALLVD G                                         31

SEQ ID NO: 73          moltype = AA  length = 32
```

| | |
|---|---|
| FEATURE | Location/Qualifiers |
| REGION | 1..32 |
| | note = Description of Artificial Sequence: Synthetic polypeptide |
| source | 1..32 |
| | mol_type = protein |
| | organism = synthetic construct |

SEQUENCE: 73
AEDQNPYWAR YADWLFTTPL LLLELALLVE CG                                          32

| | |
|---|---|
| SEQ ID NO: 74 | moltype = AA  length = 30 |
| FEATURE | Location/Qualifiers |
| REGION | 1..30 |
| | note = Description of Artificial Sequence: Synthetic polypeptide |
| source | 1..30 |
| | mol_type = protein |
| | organism = synthetic construct |

SEQUENCE: 74
AKEDQNPYWR AYADLFTPLT LLDLLALWDG                                             30

| | |
|---|---|
| SEQ ID NO: 75 | moltype = AA  length = 30 |
| FEATURE | Location/Qualifiers |
| REGION | 1..30 |
| | note = Description of Artificial Sequence: Synthetic polypeptide |
| source | 1..30 |
| | mol_type = protein |
| | organism = synthetic construct |

SEQUENCE: 75
ACEDQNPYWR AYADLFTPLT LLDLLALWDG                                             30

| | |
|---|---|
| SEQ ID NO: 76 | moltype = AA  length = 32 |
| FEATURE | Location/Qualifiers |
| REGION | 1..32 |
| | note = Description of Artificial Sequence: Synthetic polypeptide |
| source | 1..32 |
| | mol_type = protein |
| | organism = synthetic construct |

SEQUENCE: 76
AKEDQNDPYW ARYADWLFTT PLLLLDLALL VG                                          32

| | |
|---|---|
| SEQ ID NO: 77 | moltype = AA  length = 34 |
| FEATURE | Location/Qualifiers |
| REGION | 1..34 |
| | note = Description of Artificial Sequence: Synthetic polypeptide |
| source | 1..34 |
| | mol_type = protein |
| | organism = synthetic construct |

SEQUENCE: 77
TEDADVLLAL DLLLLPTTFL WDAYRAWYPN QECA                                        34

| | |
|---|---|
| SEQ ID NO: 78 | moltype = AA  length = 36 |
| FEATURE | Location/Qualifiers |
| REGION | 1..36 |
| | note = Description of Unknown: Wild-type pH-sensitive membrane polypeptide |
| source | 1..36 |
| | mol_type = protein |
| | organism = unidentified |

SEQUENCE: 78
GGEQNPIYWA RYADWLFTTP LLLLDLALLV DADEGT                                      36

| | |
|---|---|
| SEQ ID NO: 79 | moltype = AA  length = 20 |
| FEATURE | Location/Qualifiers |
| REGION | 1..20 |
| | note = Description of Artificial Sequence: Synthetic peptide |
| source | 1..20 |
| | mol_type = protein |
| | organism = synthetic construct |

SEQUENCE: 79
AEQNPIYWAR YADWLFTTPL                                                        20

| | |
|---|---|
| SEQ ID NO: 80 | moltype = AA  length = 21 |
| FEATURE | Location/Qualifiers |
| REGION | 1..21 |
| | note = Description of Artificial Sequence: Synthetic peptide |

```
source                    1..21
                          mol_type = protein
                          organism = synthetic construct
SEQUENCE: 80
AEQNPIYWAR YADWLFTTPC L                                              21

SEQ ID NO: 81             moltype = AA  length = 21
FEATURE                   Location/Qualifiers
REGION                    1..21
                          note = Description of Artificial Sequence: Synthetic peptide
source                    1..21
                          mol_type = protein
                          organism = synthetic construct
SEQUENCE: 81
ACEQNPIYWA RYADWLFTTP L                                              21

SEQ ID NO: 82             moltype = AA  length = 21
FEATURE                   Location/Qualifiers
REGION                    1..21
                          note = Description of Artificial Sequence: Synthetic peptide
source                    1..21
                          mol_type = protein
                          organism = synthetic construct
SEQUENCE: 82
ACEQNPIYFA RYADWLFTTP L                                              21

SEQ ID NO: 83             moltype = AA  length = 27
FEATURE                   Location/Qualifiers
REGION                    1..27
                          note = Description of Artificial Sequence: Synthetic peptide
source                    1..27
                          mol_type = protein
                          organism = synthetic construct
SEQUENCE: 83
ACDDQNPWRA YLDLLFPTDT LLLDLLW                                        27

SEQ ID NO: 84             moltype = AA  length = 27
FEATURE                   Location/Qualifiers
REGION                    1..27
                          note = Description of Artificial Sequence: Synthetic peptide
source                    1..27
                          mol_type = protein
                          organism = synthetic construct
SEQUENCE: 84
ACEEQNPWRA YLELLFPTET LLLELLW                                        27

SEQ ID NO: 85             moltype = AA  length = 25
FEATURE                   Location/Qualifiers
REGION                    1..25
                          note = Description of Artificial Sequence: Synthetic peptide
source                    1..25
                          mol_type = protein
                          organism = synthetic construct
SEQUENCE: 85
ACDDQNPWAR YLDWLFPTDT LLLDL                                          25

SEQ ID NO: 86             moltype = AA  length = 24
FEATURE                   Location/Qualifiers
REGION                    1..24
                          note = Description of Artificial Sequence: Synthetic peptide
source                    1..24
                          mol_type = protein
                          organism = synthetic construct
SEQUENCE: 86
CDNNNPWRAY LDLLFPTDTL LLDW                                           24

SEQ ID NO: 87             moltype = AA  length = 25
FEATURE                   Location/Qualifiers
REGION                    1..25
                          note = Description of Artificial Sequence: Synthetic peptide
source                    1..25
                          mol_type = protein
                          organism = synthetic construct
SEQUENCE: 87
ACEEQNPWAR YLEWLFPTET LLLEL                                          25

SEQ ID NO: 88             moltype = AA  length = 24
FEATURE                   Location/Qualifiers
REGION                    1..24
```

```
                               -continued note = Description of Artificial Sequence: Synthetic peptide
source                  1..24
                        mol_type = protein
                        organism = synthetic construct
SEQUENCE: 88
ACEDQNPWAR YADWLFPTTL LLLD                                                24

SEQ ID NO: 89           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 89
ACEEQNPWAR YAEWLFPTTL LLLE                                                24

SEQ ID NO: 90           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 90
ACEDQNPWAR YADLLFPTTL AW                                                  22

SEQ ID NO: 91           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 91
ACEDQNPWAR YAELLFPTTL W                                                   21

SEQ ID NO: 92           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 92
KEDQNPWARY ADLLFPTTLW                                                     20

SEQ ID NO: 93           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 93
DDDEDNPIYW ARYAHWLFTT PLLLLHGALL VDADECT                                  37

SEQ ID NO: 94           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 94
DDDEDNPIYW ARYAHWLFTT PLLLLDGALL VDADECT                                  37

SEQ ID NO: 95           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 95
DDDEDNPIYW ARYAHWLFTT PLLLLHGALL VNADECT                                  37
```

```
SEQ ID NO: 96            moltype = AA   length = 37
FEATURE                  Location/Qualifiers
REGION                   1..37
                         note = Description of Artificial Sequence: Synthetic
                          polypeptide
source                   1..37
                         mol_type = protein
                         organism = synthetic construct
SEQUENCE: 96
DDDEDNPIYW ARYAHWLFTT PLLLLHGALL VNANECT                                   37

SEQ ID NO: 97            moltype = AA   length = 37
FEATURE                  Location/Qualifiers
REGION                   1..37
                         note = Description of Artificial Sequence: Synthetic
                          polypeptide
source                   1..37
                         mol_type = protein
                         organism = synthetic construct
SEQUENCE: 97
DDDEDNPIYW ARYADWLFTT PLLLLHGALL VDADECT                                   37

SEQ ID NO: 98            moltype = AA   length = 37
FEATURE                  Location/Qualifiers
REGION                   1..37
                         note = Description of Artificial Sequence: Synthetic
                          polypeptide
source                   1..37
                         mol_type = protein
                         organism = synthetic construct
SEQUENCE: 98
ACEQNPIYWA RYADWLFTTP LLLLDLALLV DADEGTG                                   37

SEQ ID NO: 99            moltype = AA   length = 35
FEATURE                  Location/Qualifiers
REGION                   1..35
                         note = Description of Artificial Sequence: Synthetic
                          polypeptide
source                   1..35
                         mol_type = protein
                         organism = synthetic construct
SEQUENCE: 99
ACEQNPIYWA RYADWLFTTP LLLLDLALLV DADET                                     35

SEQ ID NO: 100           moltype = AA   length = 36
FEATURE                  Location/Qualifiers
REGION                   1..36
                         note = Description of Artificial Sequence: Synthetic
                          polypeptide
source                   1..36
                         mol_type = protein
                         organism = synthetic construct
SEQUENCE: 100
ACEQNPIYWA RYADWLFTTP LLLLDLALLV DADEGT                                    36

SEQ ID NO: 101           moltype = AA   length = 38
FEATURE                  Location/Qualifiers
REGION                   1..38
                         note = Description of Artificial Sequence: Synthetic
                          polypeptide
source                   1..38
                         mol_type = protein
                         organism = synthetic construct
SEQUENCE: 101
GGEQNPIYWA RYADWLFTTP LLLDLLALLV DADEGTCG                                  38

SEQ ID NO: 102           moltype = AA   length = 38
FEATURE                  Location/Qualifiers
REGION                   1..38
                         note = Description of Artificial Sequence: Synthetic
                          polypeptide
source                   1..38
                         mol_type = protein
                         organism = synthetic construct
SEQUENCE: 102
GGEQNPIYWA RYADWLFTTP LLLLLDALLV DADEGTCG                                  38

SEQ ID NO: 103           moltype = AA   length = 38
```

```
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 103
GGEQNPIYWA RYAWDLFTTP LLLLDLALLV DADEGTCG                                38

SEQ ID NO: 104          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 104
AAEQNPIYWA RYAEWLFTTP LLLLDLALLV DADEGTCG                                38

SEQ ID NO: 105          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 105
AAEQNPIYWA RYAEWLFTTP LLLLELALLV DADEGTCG                                38

SEQ ID NO: 106          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 106
GGEQNPIYWA RYDAWLFTTP LLLLDLALLV DADEGTCG                                38

SEQ ID NO: 107          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 107
GGEQNPIYWA QYDAWLFTTP LLLLDLALLV DADEGTCG                                38

SEQ ID NO: 108          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 108
GGEQNPIYWA QDYAWLFTTP LLLLDLALLV DADEGTCG                                38

SEQ ID NO: 109          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 109
AAEQNPIYWA RYAAWLFTTP LLLLDLALLV DADEGTCG                                38

SEQ ID NO: 110          moltype = AA  length = 37
FEATURE                 Location/Qualifiers
REGION                  1..37
```

```
                    note = Description of Artificial Sequence: Synthetic
                      polypeptide
source              1..37
                    mol_type = protein
                    organism = synthetic construct
SEQUENCE: 110
ACEQNPIYWA RYANWLFTTP LLLLNLALLV DADEGTG                              37

SEQ ID NO: 111      moltype = AA  length = 37
FEATURE             Location/Qualifiers
REGION              1..37
                    note = Description of Artificial Sequence: Synthetic
                      polypeptide
source              1..37
                    mol_type = protein
                    organism = synthetic construct
SEQUENCE: 111
DDDEDNPIYW ARYAHWLFTT PLLLLHGALL VNANECT                              37

SEQ ID NO: 112      moltype = AA  length = 37
FEATURE             Location/Qualifiers
REGION              1..37
                    note = Description of Artificial Sequence: Synthetic
                      polypeptide
source              1..37
                    mol_type = protein
                    organism = synthetic construct
SEQUENCE: 112
DDDEDNPIYW ARYAHWLFTT PLLLLHGALL VNADECT                              37

SEQ ID NO: 113      moltype = AA  length = 37
FEATURE             Location/Qualifiers
REGION              1..37
                    note = Description of Artificial Sequence: Synthetic
                      polypeptide
source              1..37
                    mol_type = protein
                    organism = synthetic construct
SEQUENCE: 113
DDDEDNPIYW ARYADWLFTT PLLLLHGALL VDADECT                              37

SEQ ID NO: 114      moltype = AA  length = 37
FEATURE             Location/Qualifiers
REGION              1..37
                    note = Description of Artificial Sequence: Synthetic
                      polypeptide
source              1..37
                    mol_type = protein
                    organism = synthetic construct
SEQUENCE: 114
DDDEDNPIYW ARYAHWLFTT PLLLLHGALL VDADECT                              37

SEQ ID NO: 115      moltype = AA  length = 37
FEATURE             Location/Qualifiers
REGION              1..37
                    note = Description of Artificial Sequence: Synthetic
                      polypeptide
source              1..37
                    mol_type = protein
                    organism = synthetic construct
SEQUENCE: 115
DDDEDNPIYW ARYAHWLFTT PLLLLDGALL VDADECT                              37

SEQ ID NO: 116      moltype = AA  length = 36
FEATURE             Location/Qualifiers
REGION              1..36
                    note = Description of Artificial Sequence: Synthetic
                      polypeptide
source              1..36
                    mol_type = protein
                    organism = synthetic construct
SEQUENCE: 116
GGEQNPIYWA RYADWLFTTP LLLLDLALLV NANQGT                               36

SEQ ID NO: 117      moltype = AA  length = 38
FEATURE             Location/Qualifiers
REGION              1..38
                    note = Description of Artificial Sequence: Synthetic
                      polypeptide
```

```
source                  1..38
                        mol_type = protein
                        organism = synthetic construct
SEQUENCE: 117
AAEQNPIYWA RYADWLFTTP LLLLELALLV DADEGTCG                                 38

SEQ ID NO: 118          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 118
AAEQNPIYWA RYAEWLFTTP LLLLELALLV DADEGTCG                                 38

SEQ ID NO: 119          moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 119
AAEQNPIYWA RYADWLFTTP LLLLELALLV DADEGTKCG                                39

SEQ ID NO: 120          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 120
GGEQNPIYWA QYADWLFTTP LLLLDLALLV DADEGTCG                                 38

SEQ ID NO: 121          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 121
GGEQNPIYWA QYDAWLFTTP LLLLDLALLV DADEGTCG                                 38

SEQ ID NO: 122          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 122
GGEQNPIYWA QDYAWLFTTP LLLLDLALLV DADEGTCG                                 38

SEQ ID NO: 123          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 123
GGEQNPIYWA RYADWLFTTP LLLLDLALLV NANQGT                                   36

SEQ ID NO: 124          moltype = AA  length = 37
FEATURE                 Location/Qualifiers
REGION                  1..37
                        note = Description of Artificial Sequence: Synthetic
                         polypeptide
source                  1..37
                        mol_type = protein
```

```
                        organism = synthetic construct
SEQUENCE: 124
DDDEDNPIYW ARYAHWLFTT PLLLLHGALL VNADECT                               37

SEQ ID NO: 125          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 125
DDDEDNPIYW ARYAHWLFTT PLLLLHGALL VNANECT                               37

SEQ ID NO: 126          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 126
ACEQNPIYWA RYAKWLFTTP LLLLKLALLV DADEGTG                               37

SEQ ID NO: 127          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 127
GGEQNPIYWA QDYAWLFTTP LLLLDLALLV DADEGTCG                              38

SEQ ID NO: 128          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 128
GGEQNPIYWA QYDAWLFTTP LLLLDLALLV DADEGTCG                              38

SEQ ID NO: 129          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 129
GGEQNPIYWA QYADWLFTTP LLLLDLALLV DADEGTCG                              38

SEQ ID NO: 130          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 130
AAEQNPIYWA RYAAWLFTTP LLLLDLALLV DADEGTCG                              38

SEQ ID NO: 131          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 131
```

```
AAEQNPIYWA RYADWLFTDL PLLLLDLLAL LVDADEGT                              38

SEQ ID NO: 132          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 132
GGEQNPIYWA RYADWLFTTP LLLLLDALLV DADEGTCG                              38

SEQ ID NO: 133          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 133
GGEQNPIYWA RYADWLFTTP LLLDLLALLV DADEGTCG                              38

SEQ ID NO: 134          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 134
AAEQNPIYWA RYADWLFTTG LLLLDLALLV DADEGT                                36

SEQ ID NO: 135          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 135
AAEQNPIYWA RYAAWLFTTP LLLLDLALLV DADEGTCG                              38

SEQ ID NO: 136          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 136
GGEQNPIYWA QYDAWLFTTP LLLLDLALLV DADEGTCG                              38

SEQ ID NO: 137          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 137
GGEQNPIYWA QDYAWLFTTP LLLLDLALLV DADEGTCG                              38

SEQ ID NO: 138          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 138
GGEQNPIYWA RYDAWLFTTP LLLLDLALLV DADEGTCG                              38
```

```
-continued

SEQ ID NO: 139          moltype = AA   length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 139
AAEQNPIYWA RYADWLFTTP LLLLALALLV DADEGTCG                                38

SEQ ID NO: 140          moltype = AA   length = 39
FEATURE                 Location/Qualifiers
REGION                  1..39
                        note = Description of Artificial Sequence: Synthetic
                         polypeptide
REGION                  37
                        note = Lys(rhodamine)
REGION                  38
                        note = Cys(phalloidin)
source                  1..39
                        mol_type = protein
                        organism = synthetic construct
SEQUENCE: 140
AAEQNPIYWA RYADWLFTTP LLLLDLALLV DADEGTKCG                               39

SEQ ID NO: 141          moltype = AA   length = 39
FEATURE                 Location/Qualifiers
SITE                    37
                        note = Lys (rhodamine)
SITE                    38
                        note = Cys (phalloidin)
source                  1..39
                        mol_type = protein
                        organism = synthetic construct
SEQUENCE: 141
AAEQNPIYWA RYADWLFTTP LLLLELALLV DADEGTKCG                               39

SEQ ID NO: 142          moltype = AA   length = 38
FEATURE                 Location/Qualifiers
SITE                    37
                        note = Cys (phalloidin)
source                  1..38
                        mol_type = protein
                        organism = synthetic construct
SEQUENCE: 142
AAEQNPIYWA RYADWLFTTP LLLLDLALLV DADEGTCG                                38

SEQ ID NO: 143          moltype = AA   length = 38
FEATURE                 Location/Qualifiers
SITE                    37
                        note = Cys (phalloidin)
source                  1..38
                        mol_type = protein
                        organism = synthetic construct
SEQUENCE: 143
AAEQNPIYWA RYADWLFTTP LLLLDLALLV DADEGTCG                                38

SEQ ID NO: 144          moltype = AA   length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 144
GGEQNPIYWA RYADWLFTTP LLLLDLALLV DADEGTCG                                38

SEQ ID NO: 145          moltype = AA   length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 145
ACEQNPIYWA RYADWLFTTP LLLLDLALLV DADET                                   35
```

```
SEQ ID NO: 146         moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 146
ACEQNPIYWA RYADWLFTTP LLLLDLALLV DADEGTG                                  37

SEQ ID NO: 147         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 147
ACEQNPIYWA RYADWLFTTP LLLLDLALLV DADEGT                                   36

SEQ ID NO: 148         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 148
GGEQNPIYWA RYADWLFTTP LLLLDLALLV NANQGT                                   36

SEQ ID NO: 149         moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 149
DDDEDNPIYW ARYAHWLFTT PLLLLHGALL VNADECT                                  37

SEQ ID NO: 150         moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 150
DDDEDNPIYW ARYAHWLFTT PLLLLHGALL VNANECT                                  37

SEQ ID NO: 151         moltype = AA  length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 151
GGEQNPIYWA RYADWLFTTP LLLLDLALLV DADEGTCG                                 38

SEQ ID NO: 152         moltype = AA  length = 38
FEATURE                Location/Qualifiers
SITE                   37
                       note = Cys (phalloidin)
source                 1..38
                       mol_type = protein
                       organism = synthetic construct
SEQUENCE: 152
AAEQNPIYWA RYADWLFTTP LLLLDLALLV DADEGTCG                                 38

SEQ ID NO: 153         moltype = AA  length = 39
FEATURE                Location/Qualifiers
```

```
                        -continued source                  1..39
                        mol_type = protein
                        organism = synthetic construct
VARIANT                 37
                        note = Lys (rhodamine)
VARIANT                 38
                        note = Cys (phalloidin)
SEQUENCE: 153
AAEQNPIYWA RYADWLFTTP LLLLELALLV DADEGTKCG                              39

SEQ ID NO: 154          moltype = AA  length = 39
FEATURE                 Location/Qualifiers
SITE                    37
                        note = Lys (rhodamine)
SITE                    38
                        note = Cys (phalloidin)
source                  1..39
                        mol_type = protein
                        organism = synthetic construct
SEQUENCE: 154
AAEQNPIYWA RYADWLFTTP LLLLDLALLV DADEGTKCG                              39

SEQ ID NO: 155          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 155
DDDEDNPIYW ARYAHWLFTT PLLLLHGALL VDADECT                                37

SEQ ID NO: 156          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 156
DDDEDNPIYW ARYAHWLFTT PLLLLDGALL VDADECT                                37

SEQ ID NO: 157          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 157
DDDEDNPIYW ARYAHWLFTT PLLLLHGALL VNADECT                                37

SEQ ID NO: 158          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 158
DDDEDNPIYW ARYAHWLFTT PLLLLHGALL VNANECT                                37

SEQ ID NO: 159          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 159
DDDEDNPIYW ARYADWLFTT PLLLLHGALL VDADECT                                37

SEQ ID NO: 160          moltype = AA  length = 37
FEATURE                 Location/Qualifiers
```

```
REGION                  1..37
                        note = Description of Artificial Sequence: Synthetic
                         polypeptide
source                  1..37
                        mol_type = protein
                        organism = synthetic construct
SEQUENCE: 160
DDDEDNPIYW ARYADWLFTT PLLLLHGALL VDADECT                              37

SEQ ID NO: 161          moltype = AA   length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 161
DDDEDNPIYW ARYAHWLFTT PLLLLDGALL VDADECT                              37

SEQ ID NO: 162          moltype = AA   length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 162
DDDEDNPIYW ARYAHWLFTT PLLLLHGALL VDADECT                              37

SEQ ID NO: 163          moltype = AA   length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 163
DDDEDNPIYW ARYAHWLFTT PLLLLHGALL VNADECT                              37

SEQ ID NO: 164          moltype = AA   length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 164
DDDEDNPIYW ARYAHWLFTT PLLLLHGALL VNANECT                              37

SEQ ID NO: 165          moltype = AA   length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 165
DDDEDNPIYW ARYAHWLFTT PLLLLHGALL VNANECT                              37

SEQ ID NO: 166          moltype = AA   length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 166
DDDEDNPIYW ARYAHWLFTT PLLLLHGALL VNADECT                              37

SEQ ID NO: 167          moltype = AA   length = 37
FEATURE                 Location/Qualifiers
REGION                  1..37
                        note = Description of Artificial Sequence: Synthetic
```

```
                        polypeptide
source                  1..37
                        mol_type = protein
                        organism = synthetic construct
SEQUENCE: 167
DDDEDNPIYW ARYADWLFTT PLLLLHGALL VDADECT                              37

SEQ ID NO: 168          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 168
DDDEDNPIYW ARYAHWLFTT PLLLLHGALL VDADECT                              37

SEQ ID NO: 169          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 169
DDDEDNPIYW ARYAHWLFTT PLLLLDGALL VDADECT                              37

SEQ ID NO: 170          moltype = AA  length = 36
FEATURE                 Location/Qualifiers
REGION                  1..36
                        note = Description of Artificial Sequence: Synthetic
                        polypeptide
source                  1..36
                        mol_type = protein
                        organism = synthetic construct
SEQUENCE: 170
GGEQNPIYWA RYADWLFTTP LLLLDLALLV NANQGT                               36

SEQ ID NO: 171          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 171
DDDEDNPIYW ARYAHWLFTT PLLLLHGALL VNADECT                              37

SEQ ID NO: 172          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 172
DDDEDNPIYW ARYADWLFTT PLLLLHGALL VDADECT                              37

SEQ ID NO: 173          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 173
DDDEDNPIYW ARYAHWLFTT PLLLLHGALL VDADECT                              37

SEQ ID NO: 174          moltype = AA  length = 37
FEATURE                 Location/Qualifiers
REGION                  1..37
                        note = Description of Artificial Sequence: Synthetic
                        polypeptide
source                  1..37
```

```
                            mol_type = protein
                            organism = synthetic construct
SEQUENCE: 174
DDDEDNPIYW ARYAHWLFTT PLLLLDGALL VDADECT                                37

SEQ ID NO: 175              moltype = AA   length = 37
FEATURE                     Location/Qualifiers
REGION                      1..37
                            note = Description of Artificial Sequence: Synthetic
                             polypeptide
source                      1..37
                            mol_type = protein
                            organism = synthetic construct
SEQUENCE: 175
DDDEDNPIYW ARYAHWLFTT PLLLLHGALL VNANECT                                37

SEQ ID NO: 176              moltype = AA   length = 37
FEATURE                     Location/Qualifiers
REGION                      1..37
                            note = Description of Artificial Sequence: Synthetic
                             polypeptide
source                      1..37
                            mol_type = protein
                            organism = synthetic construct
SEQUENCE: 176
DDDEDNPIYW ARYAHWLFTT PLLLLDGALL VDADECT                                37

SEQ ID NO: 177              moltype = AA   length = 37
FEATURE                     Location/Qualifiers
REGION                      1..37
                            note = Description of Artificial Sequence: Synthetic
                             polypeptide
source                      1..37
                            mol_type = protein
                            organism = synthetic construct
SEQUENCE: 177
DDDEDNPIYW ARYADWLFTT PLLLLHGALL VDADECT                                37

SEQ ID NO: 178              moltype = AA   length = 37
FEATURE                     Location/Qualifiers
REGION                      1..37
                            note = Description of Artificial Sequence: Synthetic
                             polypeptide
source                      1..37
                            mol_type = protein
                            organism = synthetic construct
SEQUENCE: 178
DDDEDNPIYW ARYAHWLFTT PLLLLHGALL VDADECT                                37

SEQ ID NO: 179              moltype = AA   length = 37
FEATURE                     Location/Qualifiers
REGION                      1..37
                            note = Description of Artificial Sequence: Synthetic
                             polypeptide
source                      1..37
                            mol_type = protein
                            organism = synthetic construct
SEQUENCE: 179
DDDEDNPIYW ARYAHWLFTT PLLLLHGALL VNADECT                                37

SEQ ID NO: 180              moltype = AA   length = 37
FEATURE                     Location/Qualifiers
REGION                      1..37
                            note = Description of Artificial Sequence: Synthetic
                             polypeptide
source                      1..37
                            mol_type = protein
                            organism = synthetic construct
SEQUENCE: 180
DDDEDNPIYW ARYAHWLFTT PLLLLHGALL VNANECT                                37

SEQ ID NO: 181              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
```

```
SEQUENCE: 181
AAEQNPIYWA RYADWLFTTG LLLLDLALLV DADEGT                                36

SEQ ID NO: 182          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 182
GGEQNPIYWA RYAWDLFTTP LLLLDLALLV DADEGTCG                              38

SEQ ID NO: 183          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 183
GGEQNPIYWA RYDAWLFTTP LLLLDLALLV DADEGTCG                              38

SEQ ID NO: 184          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 184
GGEQNPIYWA QYDAWLFTTP LLLLDLALLV DADEGTCG                              38

SEQ ID NO: 185          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 185
GGEQNPIYWA QDYAWLFTTP LLLLDLALLV DADEGTCG                              38

SEQ ID NO: 186          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 186
AAEQNPIYWA RYAAWLFTTP LLLLDLALLV DADEGTCG                              38

SEQ ID NO: 187          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 187
GGEQNPIYWA RYADWLFTTP LLLLLDALLV DADEGTCG                              38

SEQ ID NO: 188          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 188
GGEQNPIYWA RYADWLFTTP LLLDLLALLV DADEGTCG                              38
```

```
SEQ ID NO: 189         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 189
GGEQNPIYWA RYADWLFTTP LLLDLLALLV DADEGTCG                              38

SEQ ID NO: 190         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 190
GGEQNPIYWA RYADWLFTTP LLLLLDALLV DADEGTCG                              38

SEQ ID NO: 191         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 191
GGEQNPIYWA QYADWLFTTP LLLLDLALLV DADEGTCG                              38

SEQ ID NO: 192         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 192
GGEQNPIYWA QYDAWLFTTP LLLLDLALLV DADEGTCG                              38

SEQ ID NO: 193         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 193
GGEQNPIYWA QDYAWLFTTP LLLLDLALLV DADEGTCG                              38

SEQ ID NO: 194         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 194
GGEQNPIYWA QYDAWLFTTP LLLLDLALLV DADEGTCG                              38

SEQ ID NO: 195         moltype = AA   length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 195
GGEQNPIYWA QDYAWLFTTP LLLLDLALLV DADEGTCG                              38

SEQ ID NO: 196         moltype = AA   length = 38
```

```
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 196
GGEQNPIYWA QYADWLFTTP LLLLDLALLV DADEGTCG                                    38

SEQ ID NO: 197          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 197
AAEQNPIYWA RYAAWLFTTP LLLLDLALLV DADEGTCG                                    38

SEQ ID NO: 198          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 198
GGEQNPIYWA QDYAWLFTTP LLLLDLALLV DADEGTCG                                    38

SEQ ID NO: 199          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 199
GGEQNPIYWA QYDAWLFTTP LLLLDLALLV DADEGTCG                                    38

SEQ ID NO: 200          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 200
GGEQNPIYWA QYADWLFTTP LLLLDLALLV DADEGTCG                                    38

SEQ ID NO: 201          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 201
AAEQNPIYWA RYAAWLFTTP LLLLDLALLV DADEGTCG                                    38

SEQ ID NO: 202          moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 202
AAEQNPIYWA RYADWLFTTP LLLLELALLV DADEGTKCG                                   39

SEQ ID NO: 203          moltype = AA  length = 6
FEATURE                 Location/Qualifiers
SITE                    4
```

```
                        note = Lys (rhodamine)
SITE                    5
                        note = Cys (phalloidin)
source                  1..6
                        mol_type = protein
                        organism = synthetic construct
SEQUENCE: 203
EGTKCG                                                                  6

SEQ ID NO: 204          moltype = AA  length = 39
FEATURE                 Location/Qualifiers
source                  1..39
                        mol_type = protein
                        organism = synthetic construct
VARIANT                 37
                        note = Lys (rhodamine)
VARIANT                 38
                        note = Cys (phalloidin)
SEQUENCE: 204
AAEQNPIYWA RYADWLFTTP LLLLDLALLV DADEGTKCG                              39

SEQ ID NO: 205          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 205
ACEQNPIYWA RYADWLFTTP LLLLDLALLV DADEGTG                                37

SEQ ID NO: 206          moltype = AA  length = 38
FEATURE                 Location/Qualifiers
SITE                    37
                        note = Cys (phalloidin)
source                  1..38
                        mol_type = protein
                        organism = synthetic construct
SEQUENCE: 206
AAEQNPIYWA RYADWLFTTP LLLLDLALLV DADEGTCG                               38

SEQ ID NO: 207          moltype = AA  length = 39
FEATURE                 Location/Qualifiers
SITE                    37
                        note = Lys (rhodamine)
SITE                    38
                        note = Cys (phalloidin)
source                  1..39
                        mol_type = protein
                        organism = synthetic construct
SEQUENCE: 207
AAEQNPIYWA RYADWLFTTP LLLLDLALLV DADEGTKCG                              39

SEQ ID NO: 208          moltype = AA  length = 39
FEATURE                 Location/Qualifiers
source                  1..39
                        mol_type = protein
                        organism = synthetic construct
VARIANT                 37
                        note = Lys (rhodamine)
VARIANT                 38
                        note = Cys (phalloidin)
SEQUENCE: 208
AAEQNPIYWA RYADWLFTTP LLLLELALLV DADEGTKCG                              39

SEQ ID NO: 209          moltype = AA  length = 38
FEATURE                 Location/Qualifiers
REGION                  1..38
                        note = Description of Artificial Sequence: Synthetic
                        polypeptide
source                  1..38
                        mol_type = protein
                        organism = synthetic construct
SEQUENCE: 209
AAEQNPIYWA RYADWLFTDL PLLLLDLLAL LVDADEGT                               38

SEQ ID NO: 210          moltype = AA  length = 38
FEATURE                 Location/Qualifiers
```

```
REGION                  1..38
                        note = Description of Artificial Sequence: Synthetic
                         polypeptide
source                  1..38
                        mol_type = protein
                        organism = synthetic construct
SEQUENCE: 210
AAEQNPIYWA RYAAWLFTTP LLLLDLALLV DADEGTCG                                  38

SEQ ID NO: 211          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 211
GGEQNPIYWA QYDAWLFTTP LLLLDLALLV DADEGTCG                                  38

SEQ ID NO: 212          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 212
GGEQNPIYWA QDYAWLFTTP LLLLDLALLV DADEGTCG                                  38

SEQ ID NO: 213          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 213
GGEQNPIYWA RYDAWLFTTP LLLLDLALLV DADEGTCG                                  38

SEQ ID NO: 214          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 214
AAEQNPIYWA RYAEWLFTTP LLLLDLALLV DADEGTCG                                  38

SEQ ID NO: 215          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 215
AAEQNPIYWA RYAEWLFTTP LLLLELALLV DADEGTCG                                  38

SEQ ID NO: 216          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 216
AAEQNPIYWA RYADWLFTTP LLLLALALLV DADEGTCG                                  38

SEQ ID NO: 217          moltype = AA  length = 38
FEATURE                 Location/Qualifiers
REGION                  1..38
                        note = Description of Artificial Sequence: Synthetic
```

```
                        polypeptide
source                  1..38
                        mol_type = protein
                        organism = synthetic construct
SEQUENCE: 217
AAEQNPIYWA RYADWLFTTP LLLLELALLV DADEGTCG                                38

SEQ ID NO: 218          moltype = AA  length = 38
FEATURE                 Location/Qualifiers
REGION                  1..38
                        note = Description of Artificial Sequence: Synthetic
                        polypeptide
source                  1..38
                        mol_type = protein
                        organism = synthetic construct
SEQUENCE: 218
AAEQNPIYWA RYAEWLFTTP LLLLELALLV DADEGTCG                                38

SEQ ID NO: 219          moltype = AA  length = 39
FEATURE                 Location/Qualifiers
SITE                    37
                        note = Lys (rhodamine)
SITE                    38
                        note = Cys (phalloidin)
source                  1..39
                        mol_type = protein
                        organism = synthetic construct
SEQUENCE: 219
AAEQNPIYWA RYADWLFTTP LLLLELALLV DADEGTKCG                               39

SEQ ID NO: 220          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 220
ACEQNPIYWA RYAKWLFTTP LLLLKLALLV DADEGTG                                 37

SEQ ID NO: 221          moltype = AA  length = 37
FEATURE                 Location/Qualifiers
REGION                  1..37
                        note = Description of Artificial Sequence: Synthetic
                        polypeptide
source                  1..37
                        mol_type = protein
                        organism = synthetic construct
SEQUENCE: 221
ACEQNPIYWA RYANWLFTTP LLLLNLALLV DADEGTG                                 37

SEQ ID NO: 222          moltype = AA  length = 36
FEATURE                 Location/Qualifiers
REGION                  1..36
                        note = Description of Artificial Sequence: Synthetic
                        polypeptide
source                  1..36
                        mol_type = protein
                        organism = synthetic construct
SEQUENCE: 222
AAEQNPIYWA RYADWLFTTA LLLLDLALLV DADEGT                                  36

SEQ ID NO: 223          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 223
AEQNPIYFAR YADLLFPTTL AW                                                 22

SEQ ID NO: 224          moltype = AA  length = 22
FEATURE                 Location/Qualifiers
REGION                  1..22
                        note = Description of Artificial Sequence: Synthetic peptide
source                  1..22
                        mol_type = protein
```

```
                           organism = synthetic construct
SEQUENCE: 224
AEQNPIYWAR YADLLFPTTL AF                                               22

SEQ ID NO: 225          moltype = AA   length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 225
AEQNPIYWAR YADLLFPTTL AW                                               22

SEQ ID NO: 226          moltype = AA   length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 226
ACEQNPIYWA RYADWLFTTP LLLLDLALLV DADET                                 35

SEQ ID NO: 227          moltype = AA   length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 227
GGEQNPIYWA RYADWLFTTP LLLLDLALLV DADEGT                                36

SEQ ID NO: 228          moltype = AA   length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 228
AAEQNPIYWA RYADWLFTTP LLLLDLALLV DADEGTCG                              38

SEQ ID NO: 229          moltype = AA   length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 229
AAEQNPIYWA RYADWLFTTP LLLLDLALLV DADEGTKCG                             39

SEQ ID NO: 230          moltype = AA   length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 230
AKEQNPIYWA RYADWLFTTP LLLLDLALLV DADECT                                36

SEQ ID NO: 231          moltype = DNA   length = 18
FEATURE                 Location/Qualifiers
source                  1..18
                        mol_type = other DNA
                        organism = synthetic construct
SEQUENCE: 231
cctcttacct cagttaca                                                    18

SEQ ID NO: 232          moltype = DNA   length = 18
FEATURE                 Location/Qualifiers
```

```
SEQ ID NO: 232              moltype = DNA   length = 18
FEATURE                     Location/Qualifiers
source                      1..18
                            mol_type = other DNA
                            organism = synthetic construct
SEQUENCE: 232
cctcttacct cagttaca                                                 18

SEQ ID NO: 233              moltype = DNA   length = 18
FEATURE                     Location/Qualifiers
source                      1..18
                            mol_type = other DNA
                            organism = synthetic construct
SEQUENCE: 233
cctcttacct cagttaca                                                 18

SEQ ID NO: 234              moltype = DNA   length = 18
FEATURE                     Location/Qualifiers
source                      1..18
                            mol_type = other DNA
                            organism = synthetic construct
SEQUENCE: 234
cctcttacct cagttaca                                                 18

SEQ ID NO: 235              moltype = DNA   length = 18
FEATURE                     Location/Qualifiers
source                      1..18
                            mol_type = other DNA
                            organism = synthetic construct
SEQUENCE: 235
cctctgacct catttaca                                                 18

SEQ ID NO: 236              moltype = DNA   length = 18
FEATURE                     Location/Qualifiers
source                      1..18
                            mol_type = other DNA
                            organism = synthetic construct
SEQUENCE: 236
cctcttacct cagttaca                                                 18

SEQ ID NO: 237              moltype = DNA   length = 18
FEATURE                     Location/Qualifiers
source                      1..18
                            mol_type = other DNA
                            organism = synthetic construct
SEQUENCE: 237
cctctgacct catttaca                                                 18

SEQ ID NO: 238              moltype = DNA   length = 18
FEATURE                     Location/Qualifiers
source                      1..18
                            mol_type = other DNA
                            organism = synthetic construct
SEQUENCE: 238
cctcttacct cagttaca                                                 18

SEQ ID NO: 239              moltype = AA    length = 38
FEATURE                     Location/Qualifiers
REGION                      1..38
                            note = Description of Unknown: pH-sensitive membrane
                             polypeptide
source                      1..38
                            mol_type = protein
                            organism = unidentified
SEQUENCE: 239
AAEQNPIYWA RYADWLFTTP LLLLDLALLV DADEGTCG                            38

SEQ ID NO: 240              moltype = AA    length = 31
FEATURE                     Location/Qualifiers
REGION                      1..31
                            note = Description of Artificial Sequence: Synthetic
                             polypeptide
source                      1..31
                            mol_type = protein
                            organism = synthetic construct
SEQUENCE: 240
AEDQNPYWAR YDWLFTTPLL LLDLALLVDC G                                   31

SEQ ID NO: 241              moltype = AA    length = 32
FEATURE                     Location/Qualifiers
REGION                      1..32
```

```
                        note = Description of Artificial Sequence: Synthetic
                         polypeptide
source                  1..32
                        mol_type = protein
                        organism = synthetic construct
SEQUENCE: 241
AEDQNPYWAR YADWLFTTPL LLLELALLVE CG                                       32

SEQ ID NO: 242          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 242
AEQNPIYWAR YADWLFTTPL LLLDLALLVD ADEGCT                                   36

SEQ ID NO: 243          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 243
ACEQNPIYWA RYADWLFTTP LLLLDLALLV DADET                                    35

SEQ ID NO: 244          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 244
AEQNPIYWAR YADWLFTTPL LLLDLALLVD ADEGT                                    35

SEQ ID NO: 245          moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 245
AEDQNPYWAR YADWLFTTPL LLLDLALLVD G                                        31

SEQ ID NO: 246          moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 246
AEDQNDPYWA RYADWLFTTP LLLLDLALLV G                                        31

SEQ ID NO: 247          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 247
AEQNPIYWAR YADFLFTTPL LLLDLALLVD ADET                                     34

SEQ ID NO: 248          moltype = AA  length = 34
FEATURE                 Location/Qualifiers
REGION                  1..34
                        note = Description of Artificial Sequence: Synthetic
                         polypeptide
```

```
                         -continued source              1..34
                    mol_type = protein
                    organism = synthetic construct
SEQUENCE: 248
AEQNPIYFAR YADWLFTTPL LLLDLALLVD ADET                                34

SEQ ID NO: 249      moltype = AA  length = 34
FEATURE             Location/Qualifiers
REGION              1..34
                    note = Description of Artificial Sequence: Synthetic
                     polypeptide
source              1..34
                    mol_type = protein
                    organism = synthetic construct
SEQUENCE: 249
AEQNPIYFAR YADFLFTTPL LLLDLALLWD ADET                                34

SEQ ID NO: 250      moltype = AA  length = 36
FEATURE             Location/Qualifiers
REGION              1..36
                    note = Description of Artificial Sequence: Synthetic
                     polypeptide
source              1..36
                    mol_type = protein
                    organism = synthetic construct
SEQUENCE: 250
AEQNPIYWAR YADWLFTTPL LLLDLALLVD ADEGCT                              36

SEQ ID NO: 251      moltype = AA  length = 34
FEATURE             Location/Qualifiers
REGION              1..34
                    note = Description of Artificial Sequence: Synthetic
                     polypeptide
source              1..34
                    mol_type = protein
                    organism = synthetic construct
SEQUENCE: 251
AEDQNPIYWA RYADWLFTTP LLLLDLALLV DCGT                                34

SEQ ID NO: 252      moltype = AA  length = 35
FEATURE             Location/Qualifiers
REGION              1..35
                    note = Description of Artificial Sequence: Synthetic
                     polypeptide
source              1..35
                    mol_type = protein
                    organism = synthetic construct
SEQUENCE: 252
AEDQNDPIYW ARYADWLFTT PLLLLELALL VECGT                               35

SEQ ID NO: 253      moltype = AA  length = 25
FEATURE             Location/Qualifiers
REGION              1..25
                    note = Description of Artificial Sequence: Synthetic peptide
source              1..25
                    mol_type = protein
                    organism = synthetic construct
SEQUENCE: 253
ACEEQNPWAR YLEWLFPTET LLLEL                                          25

SEQ ID NO: 254      moltype = AA  length = 35
FEATURE             Location/Qualifiers
REGION              1..35
                    note = Description of Artificial Sequence: Synthetic
                     polypeptide
source              1..35
                    mol_type = protein
                    organism = synthetic construct
SEQUENCE: 254
AEQNPIYWAR YADWLFTTPL LLLDLALLVD ADEGT                               35

SEQ ID NO: 255      moltype = AA  length = 32
FEATURE             Location/Qualifiers
REGION              1..32
                    note = Description of Artificial Sequence: Synthetic
                     polypeptide
source              1..32
                    mol_type = protein
                    organism = synthetic construct
```

```
SEQUENCE: 255
AKEDQNPYWA RYADWLFTTP LLLLDLALLV DG                                    32

SEQ ID NO: 256          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 256
AKEDQNDPYW ARYADWLFTT PLLLLDLALL VG                                    32

SEQ ID NO: 257          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 257
AEQNPIYWAR YADWLFTTPL LLLDLALLVD ADEGC                                 35

SEQ ID NO: 258          moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 258
AEDQNPYWAR YADWLFTTPL LLLDLALLVD C                                     31

SEQ ID NO: 259          moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 259
AEDQNPYWAR YADWLFTTPL LLLELALLVE C                                     31

SEQ ID NO: 260          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 260
ACEQNPIYWA RYADWLFTTP LLLLDLALLV DADEGT                                36

SEQ ID NO: 261          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 261
ACEDQNPYWA RYADWLFTTP LLLLDLALLV DG                                    32

SEQ ID NO: 262          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 262
ACEDQNPYWR AYADLFTPLT LLDLLALWDG                                       30
```

-continued

```
SEQ ID NO: 263          moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 263
ACDDQNPWRA YLDLLFPTDT LLLDLLW                                              27

SEQ ID NO: 264          moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 264
ACEEQNPWRA YLELLFPTET LLLELLW                                              27

SEQ ID NO: 265          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 265
ACDDQNPWAR YLDWLFPTDT LLLDL                                                25

SEQ ID NO: 266          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 266
CDNNNPWRAY LDLLFPTDTL LLDW                                                 24

SEQ ID NO: 267          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 267
ACEEQNPWAR YLEWLFPTET LLLEL                                                25

SEQ ID NO: 268          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 268
CEEQQPWAQY LELLFPTETL LLEW                                                 24

SEQ ID NO: 269          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 269
CEEQQPWRAY LELLFPTETL LLEW                                                 24

SEQ ID NO: 270          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 270
```

```
ACEDQNPWAR YADWLFPTTL LLLD                                                  24

SEQ ID NO: 271          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 271
ACEEQNPWAR YAEWLFPTTL LLLE                                                  24

SEQ ID NO: 272          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 272
ACEDQNPWAR YADLLFPTTL AW                                                    22

SEQ ID NO: 273          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 273
ACEEQNPWAR YAELLFPTTL AW                                                    22

SEQ ID NO: 274          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 274
TEDADVLLAL DLLLLPTTFL WDAYRAWYPN QECA                                       34

SEQ ID NO: 275          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 275
CDDDDDNPNY WARYANWLFT TPLLLLNGAL LVEAEET                                    37

SEQ ID NO: 276          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 276
CDDDDDNPNY WARYAPWLFT TPLLLLPGAL LVEAEET                                    37

SEQ ID NO: 277          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 277
AEQNPIYWAR YADWLFTTPL LLLDLALLVD ADEGCT                                     36

SEQ ID NO: 278          moltype = AA  length = 37
FEATURE                 Location/Qualifiers
REGION                  1..37
```

```
                    note = Description of Artificial Sequence: Synthetic
                     polypeptide
source              1..37
                    mol_type = protein
                    organism = synthetic construct
SEQUENCE: 278
AKEQNPIYWA RYADWLFTTP LLLLDLALLV DADEGTG                            37

SEQ ID NO: 279      moltype = AA   length = 36
FEATURE             Location/Qualifiers
REGION              1..36
                    note = Description of Artificial Sequence: Synthetic
                     polypeptide
source              1..36
                    mol_type = protein
                    organism = synthetic construct
SEQUENCE: 279
ACEQNPIYWA RYANWLFTTP LLLLNLALLV DADEGT                             36

SEQ ID NO: 280      moltype = AA   length = 36
FEATURE             Location/Qualifiers
REGION              1..36
                    note = Description of Artificial Sequence: Synthetic
                     polypeptide
source              1..36
                    mol_type = protein
                    organism = synthetic construct
SEQUENCE: 280
DDDEDNPIYW ARYADWLFTT PLLLLHGALL VDADET                             36

SEQ ID NO: 281      moltype = AA   length = 36
FEATURE             Location/Qualifiers
REGION              1..36
                    note = Description of Artificial Sequence: Synthetic
                     polypeptide
source              1..36
                    mol_type = protein
                    organism = synthetic construct
SEQUENCE: 281
DDDEDNPIYW ARYADWLFTT PLLLLHGALL VDADET                             36

SEQ ID NO: 282      moltype = AA   length = 37
FEATURE             Location/Qualifiers
REGION              1..37
                    note = Description of Artificial Sequence: Synthetic
                     polypeptide
source              1..37
                    mol_type = protein
                    organism = synthetic construct
SEQUENCE: 282
CDDDEDNPIY WARYAHWLFT TPLLLLHGAL LVDADET                            37

SEQ ID NO: 283      moltype = AA   length = 37
FEATURE             Location/Qualifiers
REGION              1..37
                    note = Description of Artificial Sequence: Synthetic
                     polypeptide
source              1..37
                    mol_type = protein
                    organism = synthetic construct
SEQUENCE: 283
DDDEDNPIYW ARYAHWLFTT PLLLLHGALL VDADEGT                            37

SEQ ID NO: 284      moltype = AA   length = 37
FEATURE             Location/Qualifiers
REGION              1..37
                    note = Description of Artificial Sequence: Synthetic
                     polypeptide
source              1..37
                    mol_type = protein
                    organism = synthetic construct
SEQUENCE: 284
DDDEDNPIYW ARYAHWLFTT PLLLLHGALL VNADEGT                            37

SEQ ID NO: 285      moltype = AA   length = 37
FEATURE             Location/Qualifiers
REGION              1..37
                    note = Description of Artificial Sequence: Synthetic
                     polypeptide
```

```
source                   1..37
                         mol_type = protein
                         organism = synthetic construct
SEQUENCE: 285
DDDEDNPIYW ARYAHWLFTT PLLLLHGALL VNANEGT                              37

SEQ ID NO: 286           moltype = AA  length = 32
FEATURE                  Location/Qualifiers
REGION                   1..32
                         note = Description of Artificial Sequence: Synthetic
                          polypeptide
source                   1..32
                         mol_type = protein
                         organism = synthetic construct
SEQUENCE: 286
AKEDQNDPYW ARYADWLFTT PLLLLDLALL VG                                   32

SEQ ID NO: 287           moltype = AA  length = 31
FEATURE                  Location/Qualifiers
REGION                   1..31
                         note = Description of Artificial Sequence: Synthetic
                          polypeptide
source                   1..31
                         mol_type = protein
                         organism = synthetic construct
SEQUENCE: 287
AEDQNPYWAR YADWLFTTPL LLELALLVC G                                     31

SEQ ID NO: 288           moltype = AA  length = 28
FEATURE                  Location/Qualifiers
REGION                   1..28
                         note = Description of Artificial Sequence: Synthetic peptide
source                   1..28
                         mol_type = protein
                         organism = synthetic construct
SEQUENCE: 288
AKDDQNPWRA YLDLLFPTDT LLLDLLWC                                        28

SEQ ID NO: 289           moltype = AA  length = 27
FEATURE                  Location/Qualifiers
REGION                   1..27
                         note = Description of Artificial Sequence: Synthetic peptide
source                   1..27
                         mol_type = protein
                         organism = synthetic construct
SEQUENCE: 289
ACEEQNPWRA YLELLFPTET LLLELLW                                         27

SEQ ID NO: 290           moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 290
ACDDQNPWAR YLDWLFPTDT LLLDL                                           25

SEQ ID NO: 291           moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 291
CDNNNPWRAY LDLLFPTDTL LLDW                                            24

SEQ ID NO: 292           moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 292
CEEQQPWAQY LELLFPTETL LLEW                                            24

SEQ ID NO: 293           moltype = AA  length = 24
```

```
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 293
CEEQQPWRAY LELLFPTETL LLEW                                              24

SEQ ID NO: 294          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 294
CDDDDDNPNY WARYANWLFT TPLLLLNGAL LVEAEET                                37

SEQ ID NO: 295          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 295
CDDDDDNPNY WARYAPWLFT TPLLLLPGAL LVEAEE                                 36

SEQ ID NO: 296          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 296
AEQNPIYFAR YADLLFPTTL AW                                                22

SEQ ID NO: 297          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 297
AEQNPIYWAR YADLLFPTTL AF                                                22

SEQ ID NO: 298          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 298
AEQNPIYWAR YADLLFPTTL AW                                                22

SEQ ID NO: 299          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 299
KEDQNPWARY ADLLFPTTLW                                                   20

SEQ ID NO: 300          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 300
```

```
ACEEQNPQAE YAEWLFPTTL LLLE                                                    24

SEQ ID NO: 301           moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 301
AAEEQNPWAR YLEWLFPTET LLLEL                                                   25

SEQ ID NO: 302           moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 302
AKEEQNPWAR YLEWLFPTET LLLEL                                                   25

SEQ ID NO: 303           moltype = AA  length = 38
FEATURE                  Location/Qualifiers
REGION                   1..38
                         note = Description of Unknown: Wild-type pH-sensitive
                          membrane polypeptide
source                   1..38
                         mol_type = protein
                         organism = unidentified
SEQUENCE: 303
AAEQNPIYWA RYADWLFTTP LLLLDLALLV DADEGTGG                                     38

SEQ ID NO: 304           moltype = AA  length = 38
FEATURE                  Location/Qualifiers
source                   1..38
                         mol_type = protein
                         organism = synthetic construct
VARIANT                  1
                         note = Ala or Asp
VARIANT                  2
                         note = Ala, Asp or Cys
VARIANT                  4
                         note = Gln or Asp
VARIANT                  11
                         note = Arg or Gln
VARIANT                  12
                         note = Tyr or Asp
VARIANT                  13
                         note = Ala, Asp or Tyr
VARIANT                  14
                         note = Asp, Asn, Flu, His, Lys, Ala or Trp
VARIANT                  15
                         note = Trp or Asp
VARIANT                  19
                         note = Thr or Asp
VARIANT                  20
                         note = Pro, Gly or Ala
VARIANT                  24
                         note = Leu or Asp
VARIANT                  25
                         note = Asp, Leu, Asn, Glu, His, Lys or Ala
VARIANT                  26
                         note = Leu, Asp or Gly
VARIANT                  31
                         note = Asp or Asn
VARIANT                  33
                         note = Asp or Asn
VARIANT                  34
                         note = Glu or Gln
VARIANT                  35
                         note = Gly or Cys
VARIANT                  37
                         note = Gly or Cys
SEQUENCE: 304
XXEXNPIYWA XXXXXLFTXX LLLXXXALLV XAXXXTXG                                     38

SEQ ID NO: 305           moltype = AA  length = 42
FEATURE                  Location/Qualifiers
```

```
SITE               1
                   note = May or may not be present
SITE               21
                   note = May or may not be present
SITE               29
                   note = May or may not be present
SITE               40
                   note = May or may not be present
source             1..42
                   mol_type = protein
                   organism = synthetic construct
SEQUENCE: 305
DAAEQNPIYW ARYADWLFTT LPLLLLDLLA LLVDADEGTK GG                               42

SEQ ID NO: 306         moltype = AA  length = 38
FEATURE                Location/Qualifiers
REGION                 1..38
                       note = Description of Unknown: Wild-type pH-sensitive
                        membrane polypeptide
source                 1..38
                       mol_type = protein
                       organism = unidentified
SEQUENCE: 306
GGEQNPIYWA RYADWLFTTP LLLLDLALLV DADEGTGG                                   38

SEQ ID NO: 307         moltype = AA  length = 38
FEATURE                Location/Qualifiers
source                 1..38
                       mol_type = protein
                       organism = synthetic construct
SEQUENCE: 307
XXEXNPIYWA XXXXXLFTXX LLLXXXALLV XAXXXXTGG                                  38

SEQ ID NO: 308         moltype = AA  length = 44
FEATURE                Location/Qualifiers
SITE                   1
                       note = May or may not be present
SITE                   7
                       note = May or may not be present
SITE                   22
                       note = May or may not be present
SITE                   30
                       note = May or may not be present
SITE                   40
                       note = May or may not be present
SITE                   42
                       note = Lys, Cys or absent
source                 1..44
                       mol_type = protein
                       organism = synthetic construct
SEQUENCE: 308
DGGEQNDPIY WARYADWLFT TLPLLLLDLL ALLVDADEGC TXGG                            44

SEQ ID NO: 309         moltype = AA  length = 38
FEATURE                Location/Qualifiers
MOD_RES                37
                       note = S-S linker attached to the nitrogen of
                        amino-phalloidin
source                 1..38
                       mol_type = protein
                       organism = synthetic construct
SEQUENCE: 309
AAEQNPIYWA RYADWLFTTP LLLLDLALLV DADEGTCG                                   38

SEQ ID NO: 310         moltype = AA  length = 31
FEATURE                Location/Qualifiers
source                 1..31
                       mol_type = protein
                       organism = synthetic construct
```

```
MOD_RES          1
                 note = S-S linker attached to 2-amino phalloidin
MOD_RES          29
                 note = Lys residue 29 modified with an alkyl linker
                   attached to rhodamine
MOD_RES          30
                 note = Alanine residue 1 modified with a COCH3 group
SEQUENCE: 310
AEDQNPYWAR YDWLFTTPLL LLDLALLVDC G                               31

SEQ ID NO: 311       moltype = AA  length = 34
FEATURE              Location/Qualifiers
source               1..34
                     mol_type = protein
                     organism = synthetic construct
SEQUENCE: 311
GLAGLAGLLG LEGLLGLPLG LLEGLWLGLE LEGN                            34
```